United States Patent
Risk et al.

(10) Patent No.: US 10,203,311 B2
(45) Date of Patent: Feb. 12, 2019

(54) GAS EMISSION DETECTION DEVICE, SYSTEM AND METHOD

(71) Applicant: St. Francis Xavier University, Antigonish (CA)

(72) Inventors: David Andrew Risk, Heatherton (CA); Bjorn-Gustaf James Brooks, Greenback, TN (US); Martin Lavoie, Orford (CA)

(73) Assignee: St. Francis Xavier University, Antigonish, Nova Scotia (CA)

( * ) Notice: Subject to any disclaimer, the term of this patent is extended or adjusted under 35 U.S.C. 154(b) by 249 days.

(21) Appl. No.: 14/955,835

(22) Filed: Dec. 1, 2015

(65) Prior Publication Data

US 2016/0161456 A1    Jun. 9, 2016

(30) Foreign Application Priority Data

Dec. 1, 2014  (CA) ..................... 2872783

(51) Int. Cl.
*G01N 33/00* (2006.01)
*G01P 5/06* (2006.01)
*G01P 13/02* (2006.01)

(52) U.S. Cl.
CPC ............ *G01N 33/0009* (2013.01); *G01P 5/06* (2013.01); *G01P 13/02* (2013.01)

(58) Field of Classification Search
CPC ................................................. G01N 33/0009
See application file for complete search history.

(56) References Cited

U.S. PATENT DOCUMENTS

| | | | |
|---|---|---|---|
| 6,645,769 B2 | 11/2003 | Tayebi et al. | |
| 8,781,755 B2 | 7/2014 | Wong | |
| 8,822,922 B1 | 9/2014 | Scanlon et al. | |
| 2014/0026641 A1 | 1/2014 | Rella | |

OTHER PUBLICATIONS

Beaubien, S.E. et al., Monitoring of near-surface gas geochemistry at the Weyburn, Canada, CO2-EOR site, 2001-2011, Int. J. Greenh. Gas Control 16, 2013, pp. S236-S262.
Bellante, G.J. et al., Aerial detection of a simulated CO2 leak from a geologic sequestration site using hyperspectral imagery, Int. J. Greenh. Gas Control 13, 2013, pp. 124-137.
Bowden, A.R. et al., Geosphere risk assessment conducted for the IEAGHG Weybum-Midale CO2 Monitoring and Storage Project, Int. J. Greenh. Gas Control 16, 2013, pp. S276-S290.

(Continued)

*Primary Examiner* — Manuel A Rivera Vargas
(74) *Attorney, Agent, or Firm* — Bereskin & Parr LLP

(57) ABSTRACT

An emission monitoring system includes at least one gas analyzer for measuring a concentration of a first gas and a concentration of a second gas, a positioning system for determining the location of the at least one gas analyzer when the concentration of the first gas is measured. A method for monitoring emissions at an industrial site and a computer-implemented event detection system applies the steps of detecting the presence of a gas emission event based on a first detection ratio calculated from the measured concentration of the first gas, the measured concentration of the second gas, a background concentration of the first gas and a background concentration of the second gas.

26 Claims, 26 Drawing Sheets

(56) References Cited

OTHER PUBLICATIONS

Busch, K.W. and Busch, M.A., Cavity ring-down spectroscopy: an ultratrace-absorption measurement technique, ACS Symposium Series 720, Oxford, UK, 199; 1997, 269 pages.

US EPA, 2014. Emission Factors for Greenhouse Gas Inventories. U.S. En-vironmental Protection Agency Washington, last Modified: Apr. 4, 2014. http://www.epa.gov/climateleadership/documents/emission-factors.pdf.

US EPA, 2013. Inventory of U.S. Greenhouse Gas Emissions and Sinks: 1990 Ð 2011. U.S. Environmental Protection Agency Washington. http://www.epa.gov/climatechange/ghgemissions/.

Farrell, P. et al., Transcontinental methane measurements: Part 1. A mobile surface platform for source investigations, Atm. Environ. 74, 2013, pp. 422-431.

Forster, P. et al., Changes in Atmospheric Constituents and in Radiative Forcing. In: Climate Change 2007: The Physical Science Basis . Contribution of Working Group I to the Fourth Assessment Report of the Intergovernmental Panel on Climate Change [Solomon, S., D. Qin, M. Manning, Z. Chen, M. Marquis, K.B. Averyt, M. Tignor and H.L. Miller (eds.)] Cambridge University Press, Cambridge, United Kingdom and New York, NY, USA, 2007.

Hitchon, B., Best practices for validating $CO_2$ geological storage: observations and guidance from the IEAGHG Weyburn-Midale $CO_2$ storage project, Geoscience Publishing Sherwood Park, Canada, 2012, 353 pages.

Jones, D.G. et al., Near surface gas monitoring at the Weyburn unit in 2011. British Geological Survey Commissioned Report, CR/12/014, 2011, 91 pages.

Jones, D.G. et al., Monitoring of near surface gas seep-age from a shallow injection experiment at the $CO_2$ Field Lab, Norway, Int. J. Greenh. Gas Control 28, 2014, pp. 300-317.

Karion, A. et al., Methane emissions estimate from airbone measurements over a western United States natural gas field, Geophy. Res. Lett. 40, 2013, pp. 4393-4397.

Govindan, R. et al., Comparative assessment of the performance of airbone and spaceborn spectral data for monitoring surface $CO_2$ leakages, Energy Procedia 4, 2011, pp. 3421-3427.

Leifer, I. et al., Transcontinental methane measurements: Part 2. Mobile surface investigation of fossil fuel industrial fugitive emissions, Atm. Environ. 74, 2013, pp. 432-441.

Mayer, B. et al., Tracing the movement and the fate of injected $CO_2$ at the IEA GHG Weyburn-Midale $CO_2$ monitoring and storage project (Saskatchewan, Canada) using carbon isotope ratios, Int. J. Greenh. Gas Control 16S, 2013, pp. S177-S184.

Monteil, G. et al., Interpreting methane variations in the past two decades using measurements of $CH_4$ mixing ratio and isotopic composition, Atm. Chem. Phys. 11, 2011, pp. 9141-9153.

Neumann, P.P. et al., Monitoring of CCS areas using micro unmanned aerial vehicles (MUAVs), Energy Procedia 37, 2013, pp. 4182-4190.

Nickerson, N. and Risk, D., Using subsurface $CO_2$ concentrations and isotopologues to identify $CO_2$ seepage from CCS/CO2-EOR sites: A signal-to-noise based analysis, Int. J. Greenh. Gas Control 14, 2013, pp. 239-246.

Pétron, G. et al., Hydrocarbon emissions characterization in the Colorado Front,Range, J. Geophy. Res-Atm. 117, 2012, DOI:10.1029/2011JD016360.

Phillips, N.G. et al., Mapping urban pipeline leaks: Methane leaks across Boston, Environ. Pollut. 173, 2013, pp. 1-4.

Pumpanen, J. et al., Comparison of different chamber techniques for measuring soil $CO_2$ efflux, Agri. For. Met. 123, 2004, pp. 159-176.

Quay, P. et al., The isotopic composition of atmospheric methane, Global Bio-geochem. Cy. 13: 1999. doi: 10.1029/1998GB900006.

Riding, J.B. and Rochette, C.A., The IEA Weyburn $CO_2$ monitoring and storage project. Final report of the European research team, British Geological Survey Research Report. RR/05/03. 2005, 54 pages.

Risk, D. et al., Bulk and isotopic characterization of biogenic $CO_2$ sources and variability in the Weyburn injection area, Int. I Greenh. Gas Control 16, 2013, pp. S263-S275.

Risk, D. et al., Using the Kerr investigations at Weyburn to screen geochemical tracers for near-surface detection and attribution of leakage at CCS/EOR Sites, Int. J. Greenh. Gas Control 35, 2015, pp. 13-17.

Romanak, K.D. et al., Process-based approach to $CO_2$ seepage detection by vadose zone gas monitoring at geologic $CO_2$ storage sites, Geophys. Res. Lett., 2012, doi:10.1029/2012GL052426.

Sherk, G. W., et al. The Kerr investigation: findings of the investigation into the impact of $CO_2$ on the Kerr property; IPAC Research Inc., final report prepared for property owners Cameron and Jean Kerr, 2011. Formerly available from the International Performance Assessment Centre for $CO_2$ Storage, now in files residing with the Saskatchewan Ministry of Energy and Resources, 2010.

Shevalier, M. et al., Brine geochemistry changes induced by $CO_2$ injection observed over a 10 year period in the Weybum oil field, Int. J. Greenh. Gas Control 16S, 2013, pp. S160-S176.

Trium, Site Assessment (SW-30-05-13-W2 M), Near Weyburn, Saskatchewan; Trium Environmental Inc. and Chemistry Matters, 2011.

Umezawa, T. et al., Contributions of natural and anthropogenic sources to atmospheric methane variations over western Siberia estimated from its carbon and hydrogen isotopes, Global Biogeochem. Cy. 26, 2012, DOI: 10.1029/2011GB004232.

Picarro Surveyor for Natural Gas Leaks.

Fig. 22
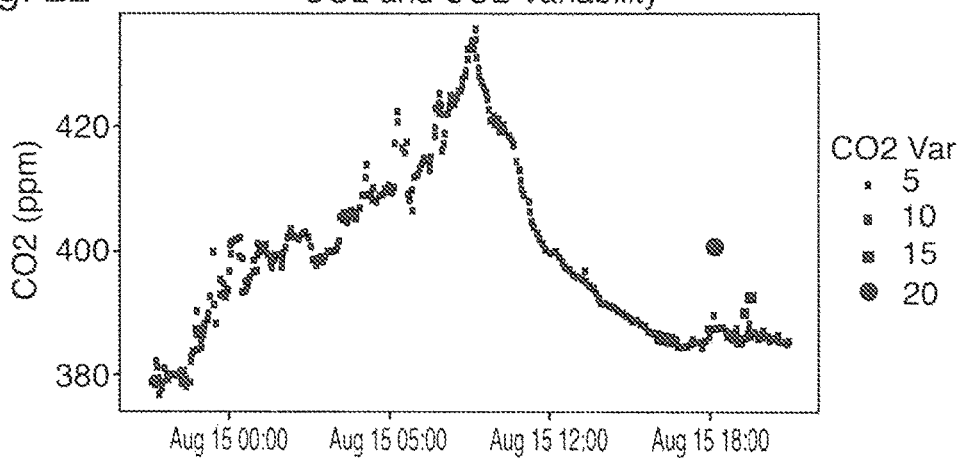
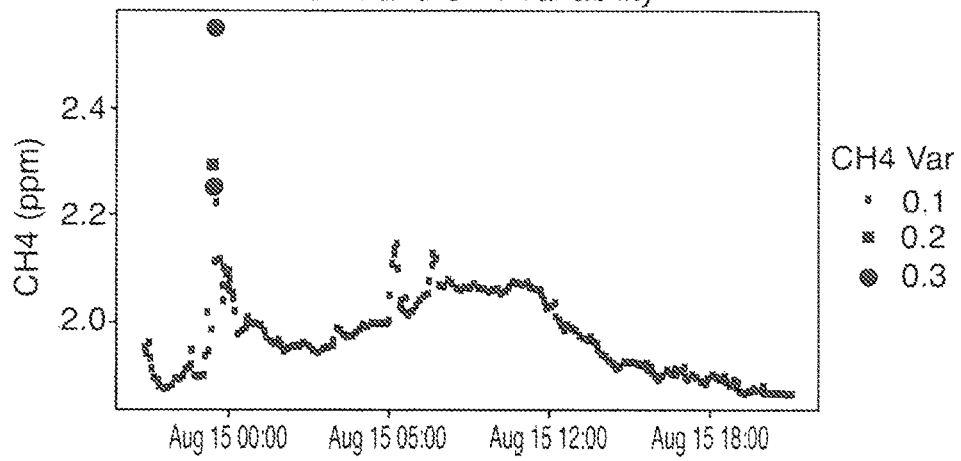
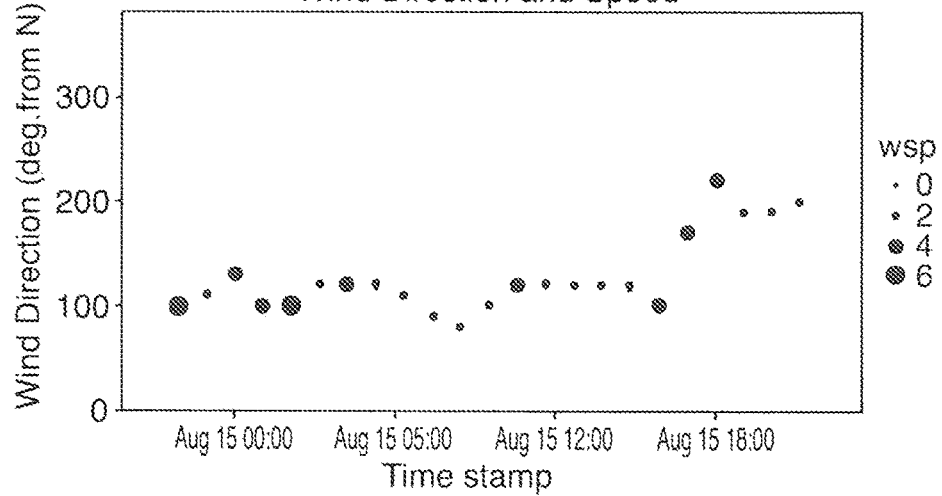

GAS EMISSION DETECTION DEVICE, SYSTEM AND METHOD

FIELD

The present subject-matter relates to a system, device and method for detecting gas emissions, and more particularly to a system, device and method for detecting gas emission events based on ratios of at least two gas species.

INTRODUCTION

The detection of gases in many industrial sites, such as energy development sites, is of interest. For example, detection of escaped gases can provide early warning indicators about the integrity of infrastructure and geologic reservoirs. Gases may be emitted from infrastructure elements, equipment or, subsurface reservoirs. Such escaped gases may represent losses to production and require monitoring in order to quantify such losses and to comply with applicable environmental regulations.

In such industrial sites, monitoring of gases may have to be carried out over a large work area. For example, the scale and spacing of pipelines, wells and other infrastructure typically used to develop energy sources such as oil and gas requires monitoring over many kilometers. Moreover, an industrial site may have multiple elements that transport or contain pressurized liquids and gases that could potentially contribute escaped gases to the atmosphere.

U.S. Pat. No. 7,669,469 to Shammai et al. discloses an apparatus and method for continuously monitoring the Integrity of a pressurized well bore fluid sample collected downhole in an earth boring or well bore. The CDR continuous by measures the temperature and pressure for the down hole sample. Near infrared, mid infrared and visible light analysis is also performed on the small amount of sample to provide an on site analysis of sample properties and contamination level. The onsite analysis comprises determination of gas oil ratio, API gravity and various other parameters which can be estimated by a trained neural network or chemometric equation a flexural mechanical resonator is also provided to measure fluid density and viscosity from which additional parameters can be estimated by a trained neural network or chemometric equation. The sample tank is overpressured or supercharged to obviate adverse pressure drop or other effects of diverting a small sample to the CDR.

U.S. Pat. No. 6,927,066 to De Angelis describes a process, and also the system for its embodiment, for the determination of pollution by MTBE in the soil and in the overlying atmosphere. An example is described relating to the monitoring of underground fuel tanks for autotraction containing an oxygenated additive.

U.S. Pat. No. 4,904,603 to Jones et al. describes a method of testing drilling mud in use which comprises periodically sampling the circulating mud and analyzing its aqueous filtrate at the rig site by ion chromatography for selected positive and negative ions; one or more other parameters of the sampled mud and/or mud filtrate (e.g. pH, temperature) may also be measured; preferably the composition of the mud filtrate thus monitored is interpreted to indicate downhole interactions, with the composition of the mud supplied to the hole being adjusted to or towards the optimum as drilling proceeds. Also disclosed is a method in which the solids of the periodically sampled mud are analyzed at the rig site, e.g. for sorbed ions and/or for cation exchange capacity; the values so obtained are preferably combined with those for the mud filtrate analysis and used in the diagnosis of downhole conditions for adjustment of the composition of freshly supplied mud. Further disclosed is a method of analyzing drilled shale solids in drilling mud in use which comprises drying and separating these solids from the mud, extracting ions from the separated solids into solution, and analyzing the resulting solution by ion chromatography for selected positive and negative ions; these operations are conducted at the rig site, and the resultant data, usually along with analyses of the circulating mud composition, are preferably used to indicate appropriate adjustment of the composition of the mud supply to or towards the optimum as drilling proceeds.

U.S. Pat. No. 7,588,943 to Prinzhofer et al. discloses a method for quantitative monitoring of a gas injected into a reservoir and likely to react chemically with the injection medium includes injecting into a reservoir a mixture of the potentially reactive gas to be quantified with a low proportion of a tracer gas whose chemical inertness is total, and in determining the variation with time of the initial proportion of reactive gas that may have disappeared through conversion, by measuring the concentration variation of the tracer gas in the mixture. The tracer gas is preferably selected from the rare gas family and from isotopes thereof, unlikely to be contaminated by contact of the mixture with the injection medium, and which have physical properties such as solubility in water or diffusion coefficients as close as possible to the gas injected. The method is applicable to monitoring of the evolution and conversion of a reactive gas such as carbon dioxide or methane, injected into an underground reservoir for example.

U.S. Pat. No. 6,645,769 to Tayebi et al. discloses a method for monitoring hydrocarbon and water production from different production zones/sections in a hydrocarbon reservoir and/or injection wells and detection of different phenomena such as e.g. local variations in pH, salinity, hydrocarbon composition, temperature, pressure, microorganisms, and the difference between production of formation and/or injection water from various zones/sections. The method includes dividing regions around wells in the reservoir into a number of zones/sections, and injecting or placing specific tracers with unique characteristics for each zone/section into the formation in these regions such that tracers are placed as integrated parts of the well completion or placed and immobilized in these regions through injection, squeeze or by other techniques. The tracers can also be immobilized or placed on a filter, a casing or other constructions surrounding the well in each zone/section. The tracers are specific or introduced to give specific information from each zone/section. The method further includes chemically immobilizing or integrating the tracers in the formation or constructions or filters around the wells, the tracers (tracer carriers) being chemically intelligent and released as a function of specific events, and detecting the tracers downstream providing information about the various zones/sections. The method may be used in a local alarm system for water breakthrough or for improved oil and gas recovery (IOR) in horizontal production and injection wells.

U.S. Pat. No. 8,232,104 to Frazier discloses a detection system including a chemical taggant and a detector. The chemical taggant may be a chemical not substantially present in an untagged target exhaust plume and able to be disposed in the exhaust system of a target and to enter the exhaust plume of the exhaust system in detectable quantities. The chemical taggant may have one or more distinct energy signatures, such as optical energy signatures, that allow its detection. The detector may be able to detect at least one of these one or more energy signatures of the chemical taggant in the exhaust plume. Another embodiment relates to a method of detecting a target by disposing a chemical taggant in the exhaust system of the target and then detecting the chemical taggant.

U.S. Pat. No. 5,319,966 to Jackson et al. discloses a method for locating non-aqueous phase liquid in an aquifer. An aqueous solution having the capacity to solubilize the contaminating liquid to concentrations greater than the solubility of the contaminant in water is injected and produced through a well. Chemical concentrations in produced fluid samples are interpreted to locate the contaminating liquid. Produced fluid samples are chemically analyzed to determine composition of the contaminant.

U.S. Pat. No. 5,264,368 to Clarke et al. discloses a method and apparatus for detecting and/or monitoring the presence of hydrocarbons in a fluid medium at a remote location, by sensing the presence of hydrocarbon-based fluid in the fluid medium in the remote location, generating a signal indicative of the sensed fluid, and transmitting the signal to monitoring means for indication of hydrocarbon contamination. The apparatus has multiple sensors at different vertical levels for sensing the fluid medium at a plurality of levels within the fluid

SUMMARY

The embodiments described herein provide in one aspect an emission monitoring system comprising at least one gas analyzer for measuring the concentration of a first gas and the concentration of a second gas, a positioning system for determining the location of the at least one gas analyzer when the concentration of the first gas is measured, a computer-implemented event detection system having a memory unit and a processor coupled to the memory unit, the processor configured for detecting presence of a gas emission event based on a first detection ratio calculated from the measured concentration of the first gas, the measured concentration of the second gas, a background concentration of the first gas, and a background concentration of the second gas.

The embodiments described herein provide in another aspect a gas emission event detection system comprising a memory unit, a processor coupled to the memory unit, the processor configured for receiving a measurement of concentration of a first gas, receiving a measurement of concentration of a second gas at substantially the same location, determining a background concentration value for the first gas, determining a background concentration value for the second gas, and detecting the presence of a gas emission event based on a first detection ratio calculated from the measured concentration of the first gas, the measured concentration of the second gas, the background concentration of the first gas, and the background concentration of the second gas.

The embodiments described herein provide in another aspect a method for monitoring emissions at a work site, the method comprising measuring the concentration of a first gas, measuring the concentration of a second gas at substantially the same location, determining a background concentration value for the first gas, determining a background concentration value for the second gas, and detecting the presence of a gas emission event based on a first detection ratio calculated from the measured concentration of the first gas, the measured concentration of the second gas, a background concentration of the first gas, and a background concentration of the second gas.

The embodiments described herein provide in another aspect a mobile gas surveying device comprising a temperature-controlled and moisture controlled enclosure having at least one inlet for receiving ambient air surrounding the enclosure, at least one gas analyzer disposed within the enclosure, the gas analyzer operable to measure concentration of at least one gas, a plurality of dampeners for reducing shock to the at least one gas analyzer.

DRAWINGS

For a better understanding of the embodiments described herein and to show more clearly how they may be carried into effect, reference will now be made, by way of example only, to the accompanying drawings which show at least one exemplary embodiment, and in which:

FIG. 22 illustrates plots of concentration and variability recorded at a stationary survey device within a test survey:

DESCRIPTION OF VARIOUS EMBODIMENTS

Figure 1:
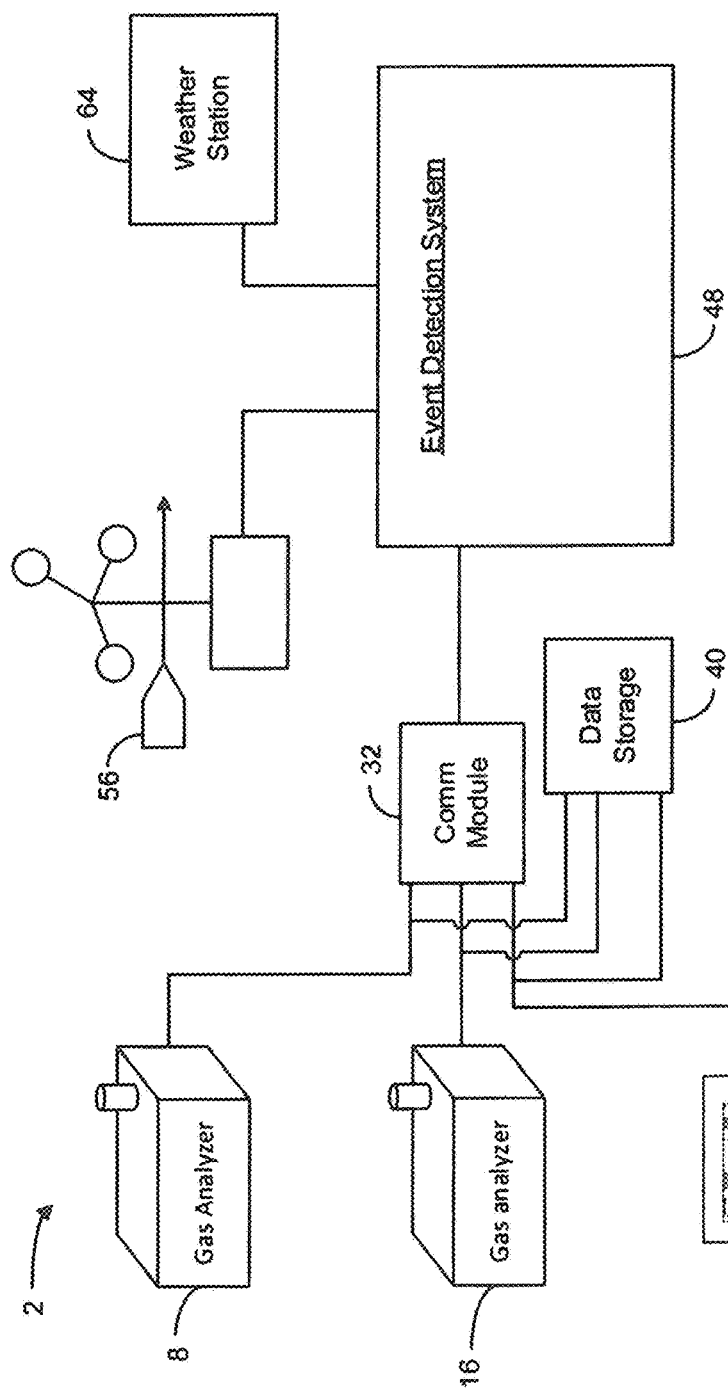
FIG. 1 is a schematic diagram of an emission monitoring system according to one exemplary embodiment.

It will be appreciated that, for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the claimed subject matter in any way but rather as merely describing the implementation of the various embodiments described herein.

"Concentration of a gas" as used herein refers to a quantifiable amount of a specific molecule, compound, or isotope in the atmosphere. For example, concentration of a gas may be as expressed in the parts-per notation (e.g. ppm, ppb).

"Gas emission event" as used herein refers to a presence of one or more gases at an industrial site reaching levels that require intervention from a site operator. Intervention can include further investigation by the site operator, identification of one or more potential emission sources of the gas emission event, or controlling of one or more potential emission sources.

"Industrial site" herein refers to a geographically bounded region in which a plurality of gas emission sources are located and in which emission of gases in the air are to be monitored.

"Gas emission source" as used herein refers to any element located on the industrial site that can emit gas at a level that, alone or in conjunction with another emission source, can cause a gas emission event.

For example, according to emission monitoring systems and gas emission event detection systems disclosed herein, detecting the presence of the gas emission event comprises: determining a first difference between the measured concentration of the first gas and the background concentration of the first gas; determining a second difference between the measured concentration of the second gas and the background concentration of the second gas; and calculating the first detection ratio by computing the ratio of the first difference to the second difference.

For example, according to emission monitoring systems and gas emission event detection systems disclosed herein, detecting the presence of the gas emission event based on the first ratio comprises comparing the first detection ratio with at least one predetermined threshold ratio value.

For example, according to emission monitoring systems and gas emission event detection systems disclosed herein, the system further comprises a wind measurement device for measuring the wind direction in proximity of the location of the at least one gas analyzer when the concentration of the first gas is measured, and wherein the processor is further configured for determining the location of the gas emission event based on the measured wind direction.

For example, according to emission monitoring systems and gas emission event detection systems disclosed herein, the wind measurement device is further configured for measuring the wind velocity in proximity of the location of the at least one gas analyzer when the concentration of the first gas is measured, and wherein determining the location of the gas emission event is further based on the measured wind velocity.

For example, according to emission monitoring systems and gas emission event detection systems disclosed herein, the processor is further configured for identifying a first gas emission source as a cause of the gas emission event based on at least one characteristic of the first source.

For example, according to emission monitoring systems and gas emission event detection systems disclosed herein, the at least one characteristic of the first source comprises at least a first gas signature of the first source, the first gas signature comprising a characterizing ratio of the amount of the first gas to the amount of the second gas emitted from the first source; and identifying the first source as a cause of the gas emission event based on the at least one characteristic of the given source comprises comparing the first calculated ratio to the characterizing ratio of the first source.

For example, according to emission monitoring systems and gas emission event detection systems disclosed herein, the at least one characteristic of the first source further comprises the location of the first source.

For example, according to emission monitoring systems and gas emission event detection systems disclosed herein, wherein identifying the first source as the cause of the gas emission event is further based on the topology of the geographic area surrounding the location of the at least one gas analyzer when the concentration of the first gas is measured.

For example, according to emission monitoring systems and gas emission event detection systems disclosed herein, the at least one analyzer is operable for measuring a concentration of a third gas; and wherein the processor of the computer-implemented event detection system is further configured for: determining a third difference between the measured concentration of the third gas and a background concentration of the third gas; calculating a second detection ratio by computing the ratio of the second difference to the third difference; and identifying a second gas emission source as the cause of the gas emission event based on comparison of the second detection ratio to a second gas-signature of the second source, the second gas-signature comprising a characterizing ratio of an amount of the second gas to an amount of the third gas emitted from the second source.

For example, according to emission monitoring systems and gas emission event detection systems disclosed herein, the at least one analyzer is operable for measuring a concentration of a third gas; and wherein the processor of the computer-implemented event detection system is further configured for: determining a third difference between the measured concentration of the third gas and a background concentration of the third gas; calculating a second detection ratio by computing the ratio of the second difference to the third difference; and validating a first gas emission source as the cause of the gas emission event based on comparison of the second detection ratio to a second gas-signature of the first source, the second gas-signature comprising a characterizing ratio of an amount of the second gas to an amount of the third gas.

For example, according to emission monitoring systems and gas emission event detection systems disclosed herein, the background concentration of the first gas and the background concentration of the second gas are selected based on at least one of: time of day; time of year; location of the first gas analyzer when the concentration of the first gas is measured; and meteorological conditions.

For example, according to emission monitoring systems and gas emission event detection systems disclosed herein, the background concentration of the first gas and the background concentration of the second gas are selected based on at least one of: minimum value during sampling period, moving average, padded moving average, running minimum and padded running minimum.

For example, according to methods for monitoring emissions at an industrial site disclosed herein, detecting the presence of the gas emission event comprises: determining a first difference between the measured concentration of the first gas and the background concentration of the first gas; determining a second difference between the measured concentration of the first gas and the background concentration of the second gas; and calculating the first detection ratio by computing the ratio of the first difference to the second difference.

For example, according to methods for monitoring emissions at an industrial site disclosed herein, determining the presence of the gas emission event comprises comparing the first detection ratio with a predetermined ratio threshold.

For example, according to methods for monitoring emissions at an industrial site disclosed herein, the method further comprises measuring the wind direction; and determining the location of the gas emission event based on the measured wind direction.

For example, according to methods for monitoring emissions at an industrial site disclosed herein, the method further comprises measuring the wind speed; determining the location of the gas emission event based on the measured wind speed.

For example, according to methods for monitoring emissions at an industrial site disclosed herein, the method further comprises identifying a first source as a cause of the gas emission event based on at least one characteristic of the first source.

For example, according to methods for monitoring emissions at an industrial site disclosed herein, the at least one characteristic of the first source comprises at least a first gas-signature of the first source, the first gas-signature comprising a characterizing ratio of an amount of the first gas to an amount of the second gas emitted from the first source; and wherein identifying the first source as a cause of the gas emission event based on at least one characteristic of the given source comprises comparing the first detection ratio to the characterizing ratio of the first source.

For example, according to methods for monitoring emissions at an industrial site disclosed herein, the at least one characteristic of the first source further comprises the location of the source.

For example, according to methods for monitoring emissions at an industrial site disclosed herein, identifying the first source as the cause of the gas emission event is further based on the topology of the geographic area surrounding the location of the gas analyzer when the concentration of the first gas is measured.

For example, according to methods for monitoring emissions at an industrial site disclosed herein, the method further comprises measuring a concentration of a third gas; determining a third difference between the measured concentration of the third gas and a concentration of the third gas; calculating a second detection ratio by computing the ratio of the second difference to the third difference; and identifying a second gas emission source as the cause of the gas emission event based on comparison of the second detection ratio to a second gas-signature of the second source, the second gas-signature comprising a characterizing ratio of an amount of the second gas to an amount of the third gas emitted from the second source.

For example, according to methods for monitoring emissions at an industrial site disclosed herein, the method further comprises receiving a measurement of a concentration of a third gas; determining a third difference between the measured concentration of the third gas and a background concentration of the third gas; calculating a second detection ratio by computing the ratio of the second difference to the third difference; and validating a first gas emission source as the cause of the gas emission event based on comparison of the second detection ratio to a second gas-signature of the first source, the second gas-signature comprising a characterizing ratio of an amount of the second gas to an amount of the third gas.

For example, according to methods for monitoring emissions at an industrial site disclosed herein, the background concentration of the first gas and the background concentration of the second gas are determined based on at least one of: time of day; time of year; location of the gas analyzer when the concentration of the first gas is measured; and meteorological conditions.

For example, according to methods for monitoring emissions at an industrial site disclosed herein, the background concentration of the first gas and the background concentration of the second gas are selected based on at least one of: minimum value during sampling period, moving average, padded moving average.

For example, according to mobile gas surveying devices disclosed herein, the enclosure has at least one opening and at least one fan mounted in the opening for assisting in control of temperature within the enclosure.

For example, according to mobile gas surveying devices disclosed herein, the plurality of dampeners comprise one or more foam members disposed between an outer surface of the at least one gas analyzer and an inner surface of the enclosure.

For example, according to mobile gas surveying devices disclosed herein, the one or more foam members provide thermal insulation for assisting in control of temperature within the enclosure.

For example, according to mobile gas surveying devices disclosed herein, the plurality of dampeners comprise a cage member for securing the at least one gas analyzer and spring members providing coupling between the cage member and the inner surface of the enclosure.

For example, according to mobile gas surveying devices disclosed herein, the device further comprises a communication module in signal communication with the at least one gas analyzer for receiving measurements of the concentration of the at least one gas and transmitting the measurements to an external device.

For example, according to mobile gas surveying devices disclosed herein, the device further comprises a data storage unit in signal communication with the at least one gas analyzer for receiving measurements of the concentration of the at least one gas and storing the measurements thereon.

For example, according to mobile gas surveying devices disclosed herein, the devices further comprises a mounting coupled to the enclosure for mounting the enclosure to at least one of a road vehicle, an all-terrain vehicle, snowmobile, and an aerial vehicle.

Referring now to FIG. 1, therein illustrated is a schematic diagram of a surveying system 2 according to one exemplary embodiment. The surveying system 2 includes at least one gas analyzer. As illustrated, the at least one gas analyzer includes a first gas analyzer 8 and a second gas analyzer 16. The at least one gas analyzer is operable to measure the concentration of a first type of gas and the concentration of a second type of gas.

The first gas analyzer 8 is operable to measure the concentration of a first type of gas, and the second gas analyzer 16 is operable to measure the concentration of a second type of gas that is different from the first type of gas.

In other examples, the at least one gas analyzer is operable to measure a set of three or more gases. For example, the at least one gas analyzer may include a plurality of gas analyzers each being operable to measure a subset of the three or more gases. The subsets may be overlapping. Having a plurality of gas analyzers allows selective deployment of the required analyzers for a given application based on the types of gases to be measured.

According to some exemplary embodiments, the at least one gas analyzer may be implemented as one or more multi-gas analyzer. A multi-gas analyzer herein refers to any gas analyzer that is operable to measure the concentration of more than one type of gas within a single device. It will be understood that reference to use of first gas analyzer and second gas analyzer herein includes the first gas analyzer and the second analyzer being implemented together within a multi-gas analyzer.

For example, the at least one gas analyzer may be a rare atmospheric tracer, such as Picarro G2301, G2401, G2132-I analyzers (Santa Clara, Calif., U.S.A.). Alternatively, one or more cost-effective but lower-resolution gas analyzers may be used.

According to various exemplary embodiments where the at least one gas analyzer includes a plurality of gas analyzers, such as the first gas analyzer 8 and second gas analyzer 16, all of the gas analyzers are co-located within the emission monitoring system 2 when deployed. For example, the gas analyzers 8 and 16 are considered co-located when they are positioned within a distance of one another such that the distance does not substantially affect the value of the concentrations that are measured by each analyzer 8, 16. It will be understood that both the first gas analyzer 8 and the second gas analyzer 16 may be deployed in a mobile manner (i.e. being in movement while obtaining measurements of concentrations of gases), but that the first gas analyzer 8 and the second gas analyzer 16 are co-located while being moved. For example, the first and second gas analyzers 8 and 16 could be carried together by a vehicle.

The term "vehicle" refers to a unit that is operable to move at least the first gas analyzer 8 and second gas analyzer 16 to at least two different locations within the industrial site. The vehicle may be a land-based vehicle, such as a car, truck, all-terrain vehicle, motorcycle, snowmobile, etc. The vehicle may also be an air-based vehicle, such as a plane, helicopter, drone or unmanned aerial vehicle (UAV). The vehicle may also refer to non-motorized units, such as a person or animal carrying the first gas analyzer and the second gas analyzer 16.

According to various exemplary embodiments, the emission monitoring system 2 may further include a positioning system 24 for determining the location of the at least one gas analyzer at the time the concentrations of the gases are measured. For example, the positioning system 24 could be a global position system (GPS) that is positioned near the at least one gas analyzer. When the at least one gas analyzer is in movement while making measurements of concentrations of gases, the positioning system 24 determines the location of the at least one gas analyzer at substantially the same time. Accordingly, a plurality of measurements of concentrations of gases made by the at least one gas analyzer may each be associated with the location at which the measurement of concentration was made.

The at least one gas analyzer may alternatively be placed at a stationary location within the industrial site to be monitored. Accordingly, the location of the at least one gas analyzer may be known and a positioning system 24 is not required.

The at least one gas analyzer generates first data pertaining to measurements of concentrations of the first gas type. The at least one gas analyzer further generates second data pertaining to measurements of concentrations of the second gas type. According to various exemplary embodiments where a positioning system 24 is provided, third data pertaining to determined locations are generated by the positioning system 24. Each measurement of concentration of the first gas type and the second gas type may be time stamped. For example, at least some measurements of the first gas type and at least some measurements of the second gas type correspond in time.

According to one exemplary embodiment, the first data, the second data, and the third data (where available) are received at one or more communication modules 32 for transmission to an external device.

For example, the communication module 32 may be operable to communicate with the external device via short range communication, using standards such as Wi-Fi, Bluetooth, Near Field Communication, etc. Accordingly, the communication module 32 may be used to transmit the first data pertaining to measurements of concentrations of the first gas, the second data pertaining to measurements of concentrations of the second gas, and the third data (where available) pertaining to determined locations to an external device located near the communication module 32. For example, the external device may be a portable electronic device such as a smartphone, laptop or tablet. The external device may receive data from the communication module 32 and display information pertaining to measurements of concentrations of the first gas and measurements of concentrations of the second gas to an operator. For example, in a mobile operation, the at least one gas analyzer may be placed in a storage area of a vehicle, such as the bed of a truck, while information pertaining to measurements made by the at least one gas analyzer can be viewed in substantially real-time on a display of the external device by an operator sitting in the cab of the truck.

For example, the communication module 32 may be operable to communicate with the external device using long range communication. The communication device 32 may be configured in accordance with various long range standards, such as the Global System for Mobile Communication (GSM), General Packet Radio Services (GPRS) 3GPP and 3GPP2, High-Speed Packet Access (HSPA) standards such as High-Speed Downlink Packet Access (HSDPA), 3GPP LTE, LTE, LTE Advanced, WiMax, and Flash-OFDM standards. New standards are still being defined, but it is believed that they will have similarities to the network behaviour described herein, and it will also be understood by persons skilled in the art that the various embodiments described herein should be able to be adapted to work with any other suitable standards that are developed in the future. Accordingly, the communication module 32 may be used to transmit the first data pertaining to measurements of concentrations of the first gas, the second data pertaining to measurements of concentrations of the second gas, and the third data (where available) pertaining to determined locations to an external device located remotely of the at least one gas analyzer.

According to one exemplary embodiment, the first data, the second data, and the third data (where available) are received at one or more storage devices 40. For example, the storage device 40 may be a hard drive, solid-state drive, flash drive or other suitable type of devices for storing the first data, the second data and the third data. First data pertaining to measurements of concentrations of the first gas, the second data pertaining to measurements of concentrations of the second gas, and the third data (where available) pertaining to determined locations can then be downloaded at a later time for analysis. For example, the storage device 40 may act as alternative to the communication module 32 (where the surveying is not time sensitive) or in addition to communication module 32 (ex: as a backup where some data is not successfully transmitted by the communication module 32).

According to various exemplary embodiments, the at least one gas analyzer and, if applicable, the positioning device 24 are in signal communication with an event detection system 48 such that the event detection system 48 can receive the first data, the second data, and the third data (where available). For example, at least one gas analyzer and, if applicable, the positioning device 24 may be in signal communication with the event detection system 48 via a wired connection or is integrated therewith. Alternatively, the at least one gas analyzer and, if applicable, the positioning device 24 may be in signal communication via the communication module 32. The event detection system 48 is configured to identify the presence of a gas emission event, as described herein elsewhere. For example, the event detection system 48 may be co-located with the at least one gas analyzer, such as within a same enclosure or onboard a mobile vehicle. Alternatively, the event detection system 48 may be remotely located, such as being a server computer.

Continuing with FIG. 1, the surveying system 2 may further include a wind anemometer 56 for measuring the wind direction in proximity to the location of the at least one gas analyzer. For example, the wind anemometer 56 may include a wind vane. The wind anemometer 56 is located on the industrial site or near the industrial site within a distance of at least one gas analyzer such that the wind direction measured by the wind anemometer 56 is representative of the direction of the wind at the location of the at least one gas analyzer. Data pertaining to the wind direction generated by the wind anemometer 56 may be received at the event detection system 48.

The wind anemometer 56 may also be operable to measure the speed of the wind in proximity to the location of the at least one gas analyzer. For example, the wind anemometer 56 may include an anemometer. Data pertaining to the wind speed generated by the wind anemometer 56 may be received at the event detection system 48.

The surveying system 2 may include a weather station 64 located on the industrial site or near the industrial site within a distance of the at least one gas analyzer such that meteorological conditions measured by the weather station 64 are representative of meteorological conditions at the location of the at least one gas analyzer. Data pertaining to meteorological conditions generated by the weather station 64 may be received at the event detection system 48.

Figure 2:
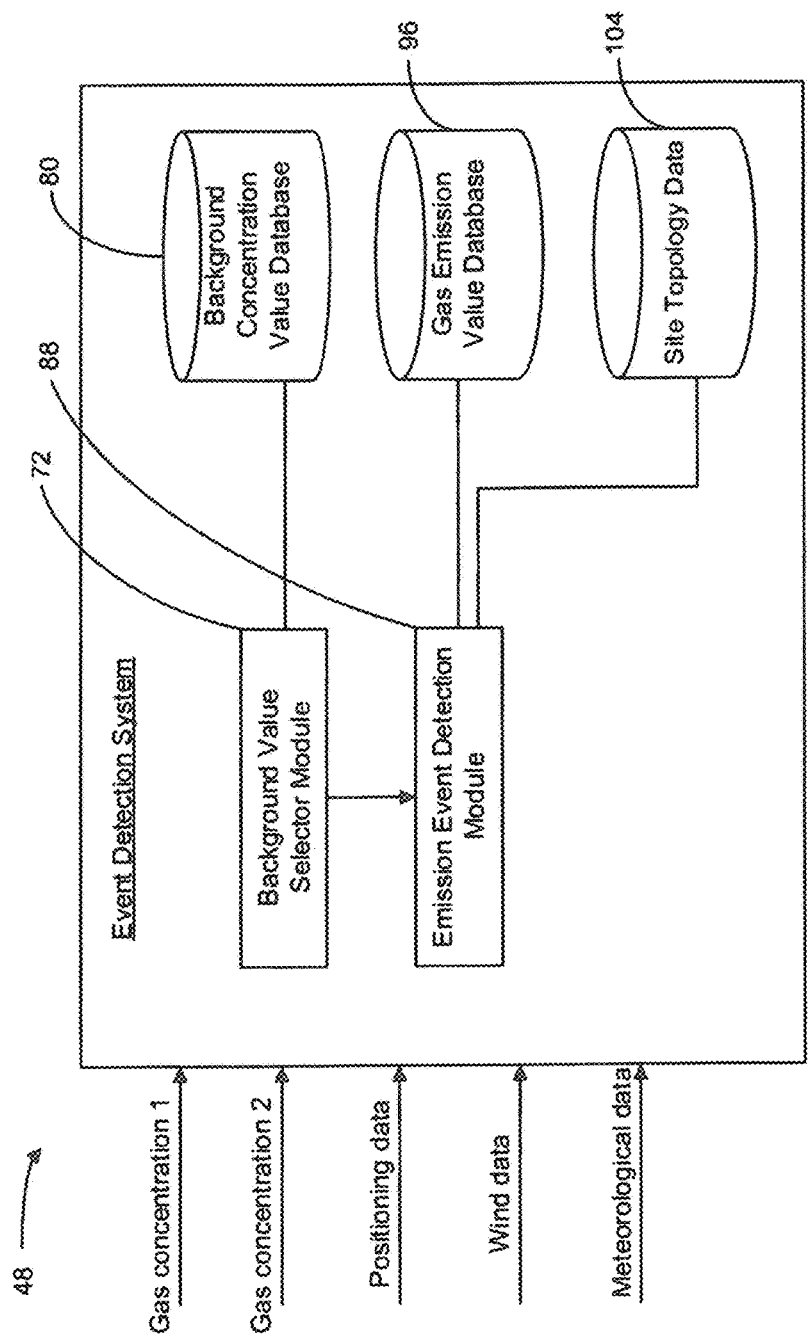
FIG. 2 is a schematic diagram of a gas emission event detection system according to one exemplary embodiment.

Referring now to FIG. 2, therein illustrated is a schematic diagram of an event detection system 48 according to certain exemplary embodiments. The event detection system 48 described herein may be implemented in computer programs executing on programmable computers, each comprising at least one microprocessor, a data storage system (including volatile and non-volatile memory and/or storage elements), at least one input device, and at least one output device. For example, and without limitation, the programmable computer may be a programmable logic unit, a mainframe computer, server, and personal computer, cloud based program or system, laptop, personal data assistance, cellular telephone, smartphone, or tablet device.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device readable by a general or special purpose programmable computer for configuring and operating the computer when the storage media or device is read by the computer to perform the procedures described herein.

The event detection system 48 receives the first data pertaining to concentrations of the first gas and the second data pertaining to concentrations of the second gas measured by the at least one gas analyzer. Where available, the event detection system 48 may further receive third data pertaining to locations measured by the positioning device 24.

The event detection system 48 includes a background value determination module 72 for determining a background concentration value for the first type of gas being measured by the at least one gas analyzer. The background value determination module 72 also determines a background concentration value for the second type of gas being measured by the at least one gas analyzer.

The background concentration value for a given gas type, such as the first gas type or second gas type, represents a concentration of the given gas type occurring naturally when a gas emission event is not present. It will be understood that the background concentration value may account for elements in the environment that naturally emit certain types of gas, such as vegetation, swamps, etc. Background concentration value may also account for man-made sources emitting types of gases within normal-operating levels, such as a manufacturing or treatment plants emitting exhaust gases.

An applicable background concentration value may be predetermined based on known characteristics of the industrial site. For example, when configuring the event detection system 48, a preliminary survey of the industrial site can be carried out to evaluate the amount of gases emitted by naturally and/or man-made gas-emitting sources present on the industrial site and to determine a background concentration value for the industrial site. For example, a plurality of background concentration values may be predetermined based on varying environmental factors that may be present.

The event detection system 48 can further include a background concentration value database 80 for storing the plurality of predetermined background concentration values. One or more predetermined background concentration values may be associated to one or more environmental factors affecting the background concentration value.

For example, within the industrial site, the background concentration values for a given type of gas may vary depending on different locations within the industrial site. For example, locations in proximity to a naturally occurring source or a man-made source may have a higher predetermined background concentration value for one or more gases being emitted from that source.

The background concentration values for a given type of gas may also vary depending on the time of day. For example, high daytime temperatures in the environment may lead to lower concentration values being measured compared to measurements made in the presence of lower night-time temperatures. The background concentration values for a given type of gas may also vary depending on the time of year. The background concentration values for a given type of gas may vary as well depending on present meteorological conditions, such as temperature, UV radiation, humidity, etc.

The background value determination module 72 determines the background concentration value for the first gas type and the background concentration value for the second gas type by querying the background concentration value database 80. The background value determination module 72 may further select a first value as a selected background concentration value for the first gas type and a second value as a selected background concentration value for the second type based on present environmental factor (ex: time of day, time of year, location, meteorological conditions). For example, a stored background concentration value may be selected if values for environmental factors associated to the stored background concentration value are closest to present environmental factors.

According to one exemplary embodiment, the background value determination module 72 adaptively updates the selected background concentration value for the first gas type and/or the selected background concentration value for the second gas type based on changes in environmental factors that are present. For example, during a mobile survey, the at least one gas analyzer may be moved between various locations, for example closer or farther away from emission sources and/or at different elevations. Accordingly, as the location of the at least one gas analyzer is moved, currently selected background concentration values for the first and second gas types may be adaptively updated.

The background value determination module 72 may determine the background concentration value for the first gas type and/or the background concentration value for the second gas type based on historical measurements of the concentrations of the first gas type and/or the second gas type, respectively. For example, where the first data pertaining to measured concentrations of the first gas type are stored, the background concentration value may be determined to be the minimum value from the measured concentrations values obtained during a survey of a work site. The minimum value may be calculated based on an average of lowest values, while removing outliers. A background concentration value for the second type of gas may be determined in an analogous manner. This way of determining the concentration values may be suitable where the topographical characteristics of the work site do not exhibit large variations, such as an area with plains.

The background value determination module 72 may determine the background concentration value for the first gas type and/or the background concentration value for the second gas type based on a moving average of past measured concentrations. For example, the background concentration value for the first type of gas may be determined to be the average of measured concentration values of the first of gas type within a most recent interval of time (ex: 5 minutes, 10 minutes etc.). The background concentration value for the second type of gas may be determined in an analogous manner. This way of determining the concentration values may be suitable where the topographical characteristics of the industrial site exhibit large variations, such as an area with many hills.

The background value determination module 72 may determine the background concentration value for the first gas type and/or the background concentration value for the second gas type based on a running minimum concentration value. For example, the background concentration value for the first type of gas may be determined to be the minimum measured concentration values of the first of gas type within a most recent interval of time (ex: 30 seconds, 1 minute, 2 minutes 5 minutes, 10 minutes etc.). The length of the time interval of time may be varied or appropriately selected based on one or more of current time of day, current weather, current season, current location, etc. Additionally, or alternatively, the length of the time interval may selected based on prior calibration results obtained from previous surveys conducted using different lengths of time interval. In various exemplary embodiments where the data are stored, the length of the time interval may be selected from plotting the number of gas emission event detected against lengths of the most recent time interval of time used. For example, the effective length of most recent time interval of time may be chosen to correspond to a break point (i.e. intersection of two regression lines) in the plot of gas emission events over time. The background concentration value for the second type of gas may be determined in an analogous manner. This way of determining the concentration values may be suitable where the topographical characteristics of the industrial site exhibit large variations, such as an area with many hills.

It was observed that varying lengths of the most recent time interval of time used for determining the minimum measured concentration value affected the number of gas emission events that were detected. According to one exemplary embodiment, the number of gas emission events detected was plotted against different lengths of the most recent time interval of time used, and the effective length of most recent time interval of time was chosen to correspond to a break point (i.e. intersection of two regression lines) in the plot of gas emission events over time.

The background value determination module 72 may determine the background concentration value for the first gas type and/or the background concentration value for the second gas type based on a running minimum concentration value with padding applied thereto. However, where the measured concentration values are stable followed by a drop in measured concentration values for some time, the running minimum concentration value will be the same as the currently measured concentration value. According to various exemplary embodiments, an amount of padding is applied to. That is, the background concentration value is determined to be the running minimum concentration value minus a value of amount corresponding to the padding. That is, the "padded" running minimum concentration value will be slightly lower than the running minimum concentration value.

According to various exemplary embodiments, the background concentration value is a mixed background value that accounts for emissions from naturally occurring sources (ex: wetlands, wooded areas, etc.) and from industrial sources within normal operating levels (i.e. when a gas emission source is not triggering an event). For example, background concentration values determined based on historical measurements or on a moving average of past measured concentrations may be a mixed background value.

The background concentration value may be a natural background value that accounts for emissions from naturally occurring sources while correcting for emissions from industrial sources. For example, measured concentrations values may be subtracted by a predetermined amount or set of amounts corresponding to emissions from industrial gas emission sources of the industrial site within normal operating levels. The predetermined amount or set of amounts may be a concentration level or set of concentrations levels that are known for each of the industrial gas emission sources. The concentration level or set of concentration levels may be known in advance (ex: manufacturing plant is known to emit A amount of first gas type and B amount of second gas type when operating normally). Alternatively, or additionally, the concentration level or set of concentration levels may be updated periodically (ex: manufacturing plant is expected to be operating at increased output for a given duration, and the expected normal emissions during this duration will be X amount of first gas type and Y amount of second gas type).

The background concentration value may also be determined based on historical concentration levels measured over an extend duration of time. For example, the extended duration of time may be a duration of at least 2 hours. The historical concentrations levels may be measured by a survey device deployed in a stationary manner that measures concentration levels on an intermittent basis (ex: every one second or several seconds). The background concentration value may be determined by removing anomalous measured concentration values that correspond to gas emission events.

According to one exemplary embodiment, the event detection system 48 further includes an emission event detection module 88 for determining whether a gas emission event is present. The emission event detection module determines the presence of a gas emission event based on a comparison of a concentration value of the first gas measured by the first gas analyzer, a concentration value of the second gas measured by the second gas analyzer, a corresponding background concentration value of the first gas and a corresponding background concentration value of the second gas. The determination of the presence of the gas emission is based on a first detection ratio calculated from the concentration value of the first gas measured by the first gas analyzer, the concentration value of the second gas measured by the second gas analyzer, the corresponding background concentration value of the first gas and the corresponding background concentration value of the second gas. A background concentration value corresponds to a given measured concentration if the environmental factors present when the measurement of the concentration was made correspond to the environmental factors used to determine the background concentration value. For example, there is correspondence where the location and time at the measuring of the concentration corresponds to the location and time values used for determining the background concentration value. This may be useful where measured concentrations are logged and stored and event detection is carried out by the event detection system based on the stored concentration measurements.

Where multiple measurements of the concentration of the first type of gas and second type of gas are made, such as during a survey of an industrial site, a determination of the presence of gas emission event may be made on each of a plurality of sets of corresponding measured concentration of the first type of gas, measured concentration of the second type of gas, the corresponding background concentration value for the first type of gas and the corresponding background concentration value for the second type of gas. A set of these values are corresponding if they share corresponding time and location characteristics. That is, the concentration of the first type of gas and the concentration of the second type of gas are measured at substantially the same time at the same location.

It has been observed that a ratio of a mixture of gases, such as a ratio of the first gas type to the second gas type provides a useful indication of anomalies, such as a gas emission event. Experiments carried out showing measuring ratios for leak detection are described in "Multi-Species leak detection for CCS and Enhanced Oil Recovery", Risk et al. 2013 American Geophysical Union AGM, December 2013, which is hereby incorporated by reference.

According to one exemplary embodiment, the emission event detection module 88 determines the presence of a gas emission event based on a differential calculation. According to this calculation, a first difference between the measured concentration of the first gas type and the current background concentration value for the first gas type is calculated. It will be appreciated that the difference may represent the contribution of the first gas type by one or more gas emitting sources above a normal emission amount represented by the background concentration value for the first gas type. The first difference represents an excess emission of the first gas type above the background concentration value.

According to the exemplary differential calculation, a second difference between the measured concentration of the second gas type and the current background concentration for the second gas type is calculated. The second difference may represent the contribution of the second gas type by one or more gas emitting sources above a normal emission amount represented by the background concentration value for second gas type. The second difference represents an excess emission of the second gas type above the background concentration value.

Figure 11B:
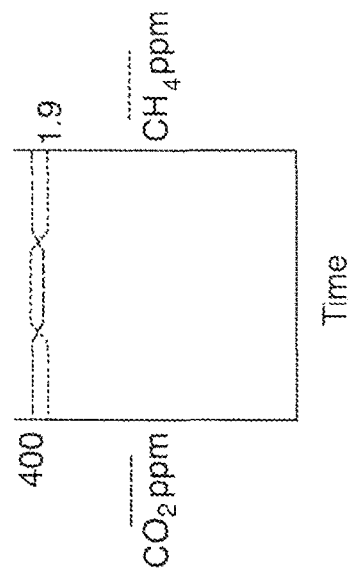
FIG. 11B illustrates a plot showing measured concentration values over time according to one example.
Figure 11C:
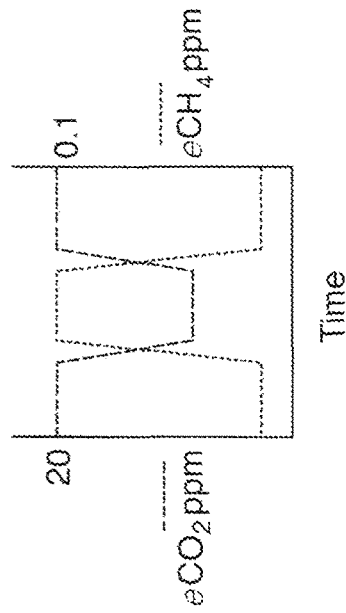
FIG. 11C illustrates a plot showing measured excess concentration values over time according to one example.
Figure 11A:
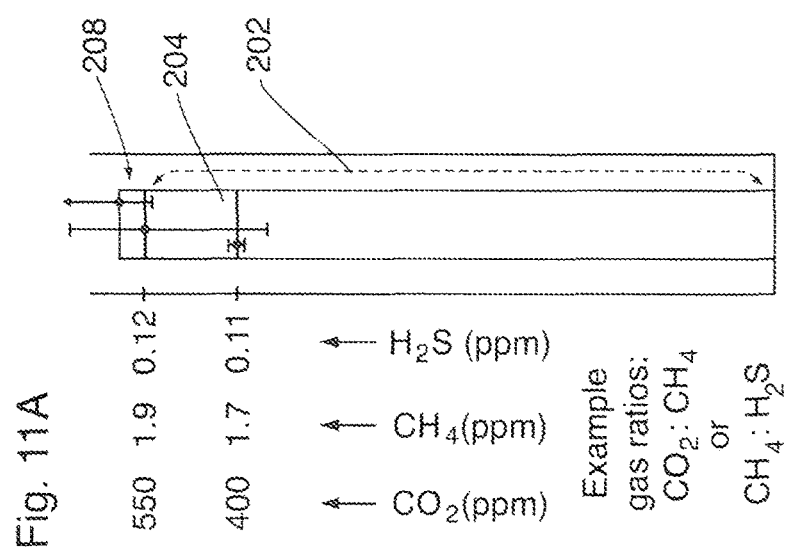
FIG. 11A illustrates a conceptual figure showing contributions to a measured concentration according to one example.

Referring now to FIG. 11A, therein illustrated is a conceptual figure showing contributions to a measured concentration. A first level 202 represents the contribution to a measured concentration provided by atmospheric or background levels. These may correspond to concentrations from large scale global patterns and/or seasonal patterns. A second level 204 represents the contribution to the measured concentration provided by biogenic sources, such as regional/local plant soil. A third level 208 represents the contribution to the measured concentration provided by industrial sources, which may be dependent on gas emission rates from emission sources at the industrial site. According to some exemplary embodiments, the background concentration value used for the differential calculation is intended to correspond to the first level contribution 200. According to some exemplary embodiments, the background concentration value used for the differential calculation is intended to correspond to the cumulative of the first level contribution 200 and the second contribution 204.

According to the exemplary differential calculation, a first detection ratio of the first difference to the second difference is calculated. The emission event detection module 88 may be further configured to determine the presence of a gas emission event based on the first detection ratio. For example, the first detection ratio is compared to a predetermined threshold ratio that is indicative of a gas emission event occurring.

It has been observed that the ratio of the first difference to the second difference may provide an improved indication of whether a gas emission event is present. For example, it has been observed that when a potential emission source causes a gas emission event, such as a leak, the potential emission source is characterized by a simultaneous emission of more than one gas.

An aggregate of multiple sources may be simultaneously emitting higher than normal levels of a given type of gas. Where at least two sources of emissions emit the given type of gas, it will be difficult to distinguish which of the two sources of emissions is causing an increased measured concentration in the given type of gas when compared to the background concentration value for the given gas type.

A single emission source may be emitting gases at critical levels, of which at least one type of gas being emitted is not easily detected or measured. Moreover, the measureable gases being emitted by the emission source may be emitted at substantially low levels compared to the natural occurring levels of these gases. Accordingly, only comparing the measured concentrations of the measureable gas types against the background concentration value may not be reveal a large change in emissions, therefore may not provide a reliable indication of the presence of a gas emission event.

In contrast, the ratio of the first difference to the second difference may provide an improved indication of the presence of a gas emission event. For example, take an exemplary first detection ratio of the background concentration value for the first gas type to the background concentration value for the second gas type. Where an emission source is emitting gases of the first gas type and the second gas type at levels that marginally contribute to the overall levels of emissions, a ratio of the measured concentration of the first gas type to the measured concentration of the second gas type may be numerically close to the exemplary first ratio. In contrast, if the emission source emits the first gas type and the second gas type at a ratio of quantities that is significantly different from the naturally occurring ratio of the two gases, the ratio of the first difference to the second difference will also be significantly different when compared to the exemplary first ratio.

Referring now to FIG. 11B, therein illustrated is a plot over time of total concentrations measured for $CO_2$ and $CH_4$ over time. It will be appreciated that the total concentration values for both gases are close to one another.

Referring now to FIG. 11C, therein illustrated is a plot over time of excess concentrations measured for $CO_2$ and $CH_4$ over time. That is, an appropriate background concentration value has been subtracted from each of the total concentration values measured for $CO_2$ and $CH_4$. It will be appreciated that the excess concentration values can be more easily distinguished.

According to one exemplary embodiment, the event detection system 72 may receive measured concentrations for more than two gas types. Accordingly, the background value determination module 72 may determine a background concentration value for each of the measured gas types. Therefore, the emission event detection module 88 may calculate for each of the two or more gas types a difference between the measured concentration and the background concentration value for that gas type to obtain a differential amount for that gas type. The emission event detection module 88 may further calculate ratios of various combinations of the differential amounts. The emission event detection module 88 may further compare the ratio for a combination of gas types against a threshold ratio corresponding to that combination to determine whether a gas emission event is present. The threshold ratio for each of a various combinations of gas types may be predetermined based on known characteristics of the industrial site, including characteristics of emission sources at the industrial site.

According to various exemplary embodiments, the emission event detection module 88 is further configured to identify a gas emission source as a cause of a gas emission event based on at least one characteristic of the given source.

A plurality of gas emission sources of an industrial site may each be characterized by a respective gas "signature". That is, a given source may be characterized by at least two types of gases emitted from that source and the ratio of the amount of the first of two types of emitted gases to the amount of the second of two types of emitted gases.

It will be understood that the amount of the first of the two types and the amount of the second of two types of gases being emitted from that source may be varying in time. For example, the amount of gases being emitted may vary substantially between a first situation where the source is not leaking (ex: emissions may be near zero) versus a second situation where the source is leaking and emitting gases. Moreover, the amount may also vary depending on the severity of the leak. However, it has been observed that for many types of gas emission sources the ratios of the amounts of different types of gases being emitted is substantially stable, which allows characterizing that gas emission source by its gas signature. For example, the gas signature characterizing a given emission source may be the ratio of amounts of the at least two types of gases being emitted by that source when the amount of emissions are sufficiently high so as to be considered as causing a gas emission event (ex: the ratios present when the source is leaking at an importantly high level).

It should be understood that the gas signature characterizing a given emission source may include a plurality of ratios of different types of gases by the gas emission source. For example, where the emission source emits three types of gases (ex: $CO_2$, $CH_4$, and $H_2S$), the gas signature of the emission source may include a first ratio of $CO_2$:$CH_4$ and a second ratio of $CH_4$:$H_2S$. Of course, a third ratio of $CO_2$:$H_2S$ may also be obtained.

According to various exemplary embodiments, the emission event detection module 88 is further configured to identify a gas emission source as a cause of a gas emission event based on the gas signature of that gas emission source. For example, a first emission source may be characterized by a first gas signature that includes a ratio of the first type of gas and the second of type of gas being measured by the at least one gas analyzer. Accordingly, the emission event detection module 88 identifies the first gas emission source as the cause of the gas emission source by comparing the first detection ratio (calculated from the concentration value of the first gas measured by the first gas analyzer, the concentration value of the second gas measured by the second gas analyzer, the corresponding background concentration value of the first gas and the corresponding background concentration value of the second gas) against the characterizing ratio of the gas signature of the first gas emission source. For example, the characterizing ratio of the gas signature may represent a threshold ratio value for the comparison. The emission event detection module 88 may determine the first gas emission source as the cause of the gas emission event if the first calculated ratio is sufficiently close (ex: within a predetermined range) of the characterizing ratio of the gas signature of the first gas emission source.

According to various exemplary embodiments, the at least one characteristic of a gas emission source may further include the location of the gas emission source. Accordingly, identifying an emission source as a cause of the gas emission event further includes comparing the location of the emission source against the location at which the concentrations of the first gas type and second gas type were measured. For example, the emission event detection module 88 may be configured to only consider gas emission sources located sufficiently near the location of the measurement as potential causes of the gas emission event.

According to various exemplary embodiments, the identifying of a gas emission source as a cause of the gas emission event may be further based on the topology of the geographic area surrounding the location at which concentrations of the first gas type and second gas type were measured. For example, a particular topological element in the vicinity of the location the gas emission source and the location of the measurement may affect whether the gas emission source should be considered as a cause of the gas emission event. For example, a high elevation element, such as a hill or mountain, between the gas emission source and the location of the measurement may block dispersion of gas emitted from that source to the location of the measurement. In such a case, that source can be removed as a potential cause of the gas emission event.

According to various exemplary embodiments, the event detection system 48 includes a gas emission source database 96 for storing information pertaining to a plurality of gas emission sources. The gas emission source database 96 may include the characteristics of each of the plurality of gas emission sources, such as one or more of gas signature and location of the gas emission sources. Information pertaining to the plurality of gas emission sources may be retrieved when the emission event detection module 48 carries out identification of a gas emission source as the cause of a gas emission event.

According to various exemplary embodiments, the event detection system 48 may receive properties of prevailing winds from the wind anemometer 56. Accordingly, the emission event detection module 88 may be further operable to determine a location of a cause of the gas emission event based on the properties of the prevailing winds.

For example, where the properties of the prevailing winds in an area of the location of the measurement of the concentrations of the first gas type and the second gas type includes the wind direction, the emission event detection module 88 may determine an approximate location of the cause of the gas emission event as being located within an area upwind of the location of the measurement of the concentrations of the first gas type and the second gas type (i.e. the measurements are being taken at a location downwind of a potential source). The emission event detection module 88 may determine an approximate location of the cause without pinpointing a specific source of the gas emission source.

Alternatively, the emission event detection module 88 may further identify the gas emission source causing the gas emission event based on the properties of prevailing winds. For example, only sources located upwind of the location of measurement could be considered as potentially causing the gas emission event.

Determining the location of the cause of the gas emission event may be further based on wind speed information received from the wind anemometer 56. For example, an approximate location of the cause of the gas emission event may be refined by limiting to a range of distances from the location of measurement based on the wind speed information.

According to various exemplary embodiments, the event detection system 48 may also receive meteorological data from the weather station 64. Identifying a cause of the gas emission may be further based on prevailing meteorological conditions.

According to some exemplary embodiments, the at least one gas analyzer is operable to measure the concentration of a third type of gas. The emission event detection module 88 may be further configured to determine the presence of the gas emission event based further on a second detection ratio calculated from the measured concentration of the third gas, a corresponding background concentration of the third gas, the measured concentration of the first (or second) type of gas, and a corresponding background concentration of the first (or second) type of gas.

The emission event detection module 88 may calculate a third difference between the measured concentration of the third type of gas and the corresponding background concentration of the third gas. The emission event detection module 88 further calculates a second detection ratio by computing the ratio of the third difference to the first difference (or the second difference). It will be appreciated that the second detection ratio corresponds to a ratio of a set of two gases that is different from the set of two gases of the first detection ratio. The emission event detection module 88 further includes identifying a second gas emission source as a cause of the gas emission event based on a comparison of the second detection ratio to a second gas signature characterizing the second emission source. For example, the second gas signature characterizes the second emission source based on a ratio of an amount of the third type of gases to the amount of either the first gas type or the second gas type emitted from the second source. It will be appreciated that the first emission source and the second emission source are characterized by respective gas signatures that have ratios for different sets of gases. This may be useful where the first and second emission sources share emissions of one or more gases of the same type but also emit other types of gases at a different ratio. For example, both the first and second emission sources may emit the first gas type and second gas type at the same ratio (ex: both first and second emission sources emit $CO_2$ and $CH_4$ at a ratio of $CO_2$:$CH_4$=200 but the first emission source emits $CH_4$ and $H_2S$ at a ratio of $CH_4$:$H_2S$=12 while the second emission source emits $CH_4$ and $H_2S$ at a ratio of $CH_4$:$H_2S$=36).

Figure 3:
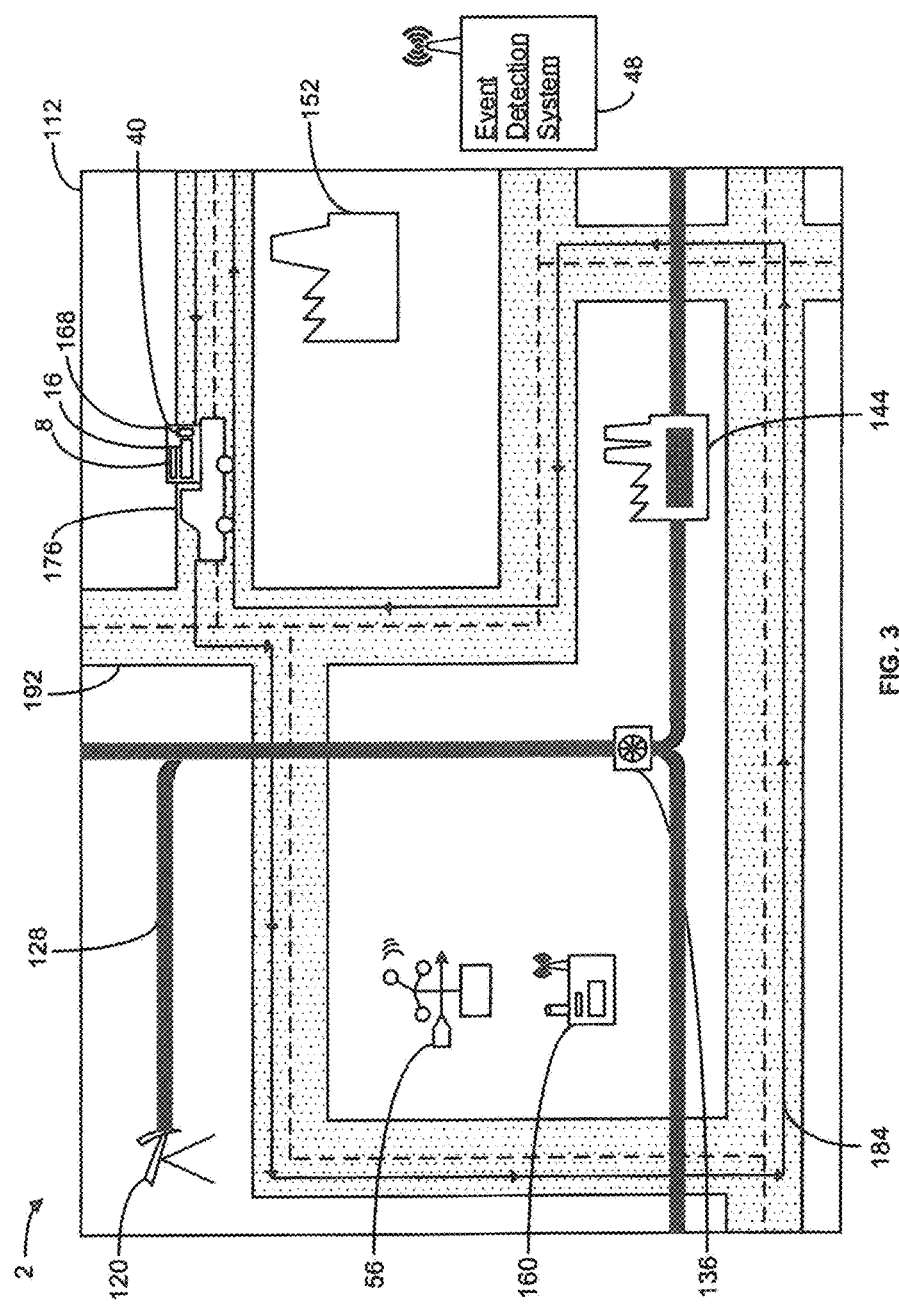
FIG. 3 is a schematic diagram of an exemplary industrial site.

Referring now to FIG. 3, therein illustrated is a plan view of an exemplary industrial site 112 in which an emission monitoring system 2 can be deployed. The exemplary industrial site 112 includes a plurality of gas emission sources such as a pumpjack pad 120, pipeline network 128, pipeline valve 136 and oil treatment plant 144 of an oil production, transportation and treatment operation. The worksite 112 may further include a manufacturing plant 152 that is unrelated to the oil production operation. The industrial site 112 further includes a wind anemometer 56 placed on the industrial site 112.

A first exemplary survey device 160 is deployed in a stationary manner to monitor the industrial site 112. The survey device 160 includes at least one gas analyzer for measuring concentrations of the first type of gas and the second type of gas. For example, since an oil production, transportation and treatment operation is being carried out, the at least one gas analyzer is selected so that the first type of gas and the second type of gas correspond to types of gases that are likely to be emitted from one or more of the pumpjack pad 120, pipeline network 128, valve 136 and treatment plant 144. The first survey device 160 further includes a long-range communication module 32 for transmitting the measured concentration of the first type of gas and the measured concentration of the second type of gas to a remotely located event detection system 48. Alternatively, the first exemplary survey device 160 may have an integrated event detection system 48. The event detection system 48 determines, based on methods and systems described herein, whether there is a presence of a gas emission event. The event detection system 48 may further identify one or more sources that may potentially be causing the gas emission event. In response to detecting the presence of a gas emission event, such as a leak, the event detection system 48 may transmit an alert providing information of the detected gas emission event.

A second exemplary survey device 168 is deployed in a mobile manner to survey the industrial site 112. For example, the survey device 168 may be mounted onto a mobile vehicle 176. The survey device 168 carries out a survey of the industrial site 112 by driving about the industrial site 112, for example, by following a defined path 184 around a road network 192 of the Industrial site 2. As the mobile vehicle 176 moves over the path 184, the at least one gas analyzer of the survey device 168 intermittently measures concentrations of at least two gases. The survey device 168 further includes a positioning device 24 for determining a location of the mobile vehicle 176 when concentrations of the at least two gases are being measured. Accordingly, for a plurality of measurements of concentrations of the at least two gases, a corresponding location at which each of these measurements occurred can be determined.

For example, data pertaining to measured concentrations and determined locations are stored on a storage device 40 of the second exemplary survey device 168. The logged data can then be received at the event detection system 48, and the presence of one or more gas emission events that were occurring during the survey can be detected.

Alternatively, the mobile vehicle 176 may also have an onboard event detection system 48 for detecting the presence of a gas emission event as the survey is ongoing.

For example, the at least two gas types being measured by the at least one gas analyzer of the second exemplary survey device 168 are different from the types of gases being measured by the first exemplary survey device 160. For example, the gas analyzer of the second exemplary survey device 168 is operative to measure a third type of gas that is not being measured by the first exemplary survey device 160. For example, the survey device 168 is configured prior to the survey by selecting an analyzer that can measure the third type of gas. This selection may be made according to expected gas emission events. For example, manufacturing plant 152 may be characterized by a gas signature that differs from the gas signatures characterizing elements of the oil production process. For example, this difference includes a third type of gas being emitted by the manufacturing plant 152 at different quantities or ratios than the elements of the oil production process. For example, if the manufacturing plant 152 is in a high period of production, a gas analyzer that measures the third type of gas is selected for improved distinction between emissions from elements of the oil production process and the manufacturing plant 152.

According to various exemplary embodiments described herein, use of gas signature allows identifying the location of the potential gas event within a spatial accuracy of tens of meters within a landscape on the scale of tens to hundreds of kilometers that includes infrastructure or geologic reservoirs.

Figure 4A:
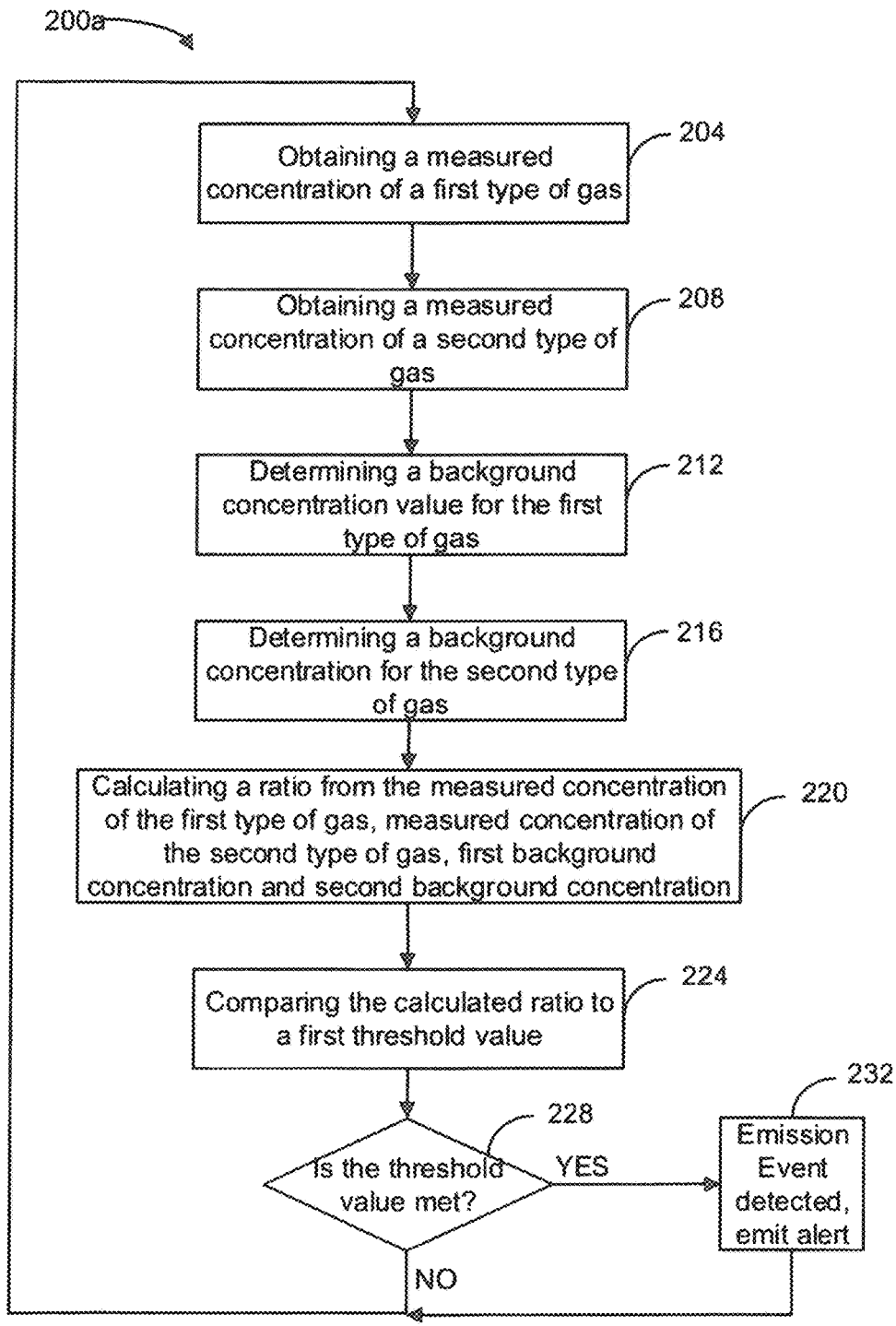
FIG. 4A is a flowchart showing the operative steps of an exemplary method for detecting a gas emission event.

Referring now to FIG. 4A, therein illustrated is a flowchart showing the operative steps of an exemplary method 200a for monitoring emissions at an industrial site. At steps 204 and 208, the measured concentration of a first type of gas and a second type of gas are obtained.

At steps 212 and 216, a background concentration value is determined for the first type of gas and another background concentration value is determined for the second type of gas.

At step 220, a detection ratio is calculated from the measured concentration of the first type of gas, the measured concentration of the second type of gas, a first background concentration value for the first type of gas, and a second background concentration value for the second type of gas. For example, the first detection ratio is calculated according to the differential calculation described herein.

At step 224, the detection ratio is compared to a first threshold value. For example, the detection ratio can be compared to a plurality of threshold values, which may correspond to characterizing ratios of different gas emission sources.

At step 228, if the detection ratio does not meet the threshold, the method returns to step 204 to begin another iteration of the method.

At step 228, if the detection ratio meets the threshold, the method proceeds to step 232 and it is detected that a gas emission event is occurring. For example, an alert notifying an operator of the gas emission event may be issued. The method then returns to step 204 to begin another iteration of the method.

It will be appreciated that an iteration of the method 200 is carried out on a corresponding set of the measured concentration of the first type of gas, the measured concentration of the second type of gas, the background concentration value for the first type of gas, and the background concentration for the second type of gas. For example, where data pertaining to measured concentrations of the first type of gas and the second type of gas are stored, an iteration may be carried out on a stored measured concentration of the first type of gas and a stored measured concentration of the second type of gas that was measured at the same time and location as the first type of gas.

For example, where the method is carried out, the concentrations of the first type of gas and the second type of gas within one iteration may be measured at substantially the same time and the remaining steps of one iteration are carried out to detect in real time if a gas emission event has occurred. A further iteration of the method 200 then corresponds to further measurements of the first type of gas and the second type of gas.

Figure 4B:
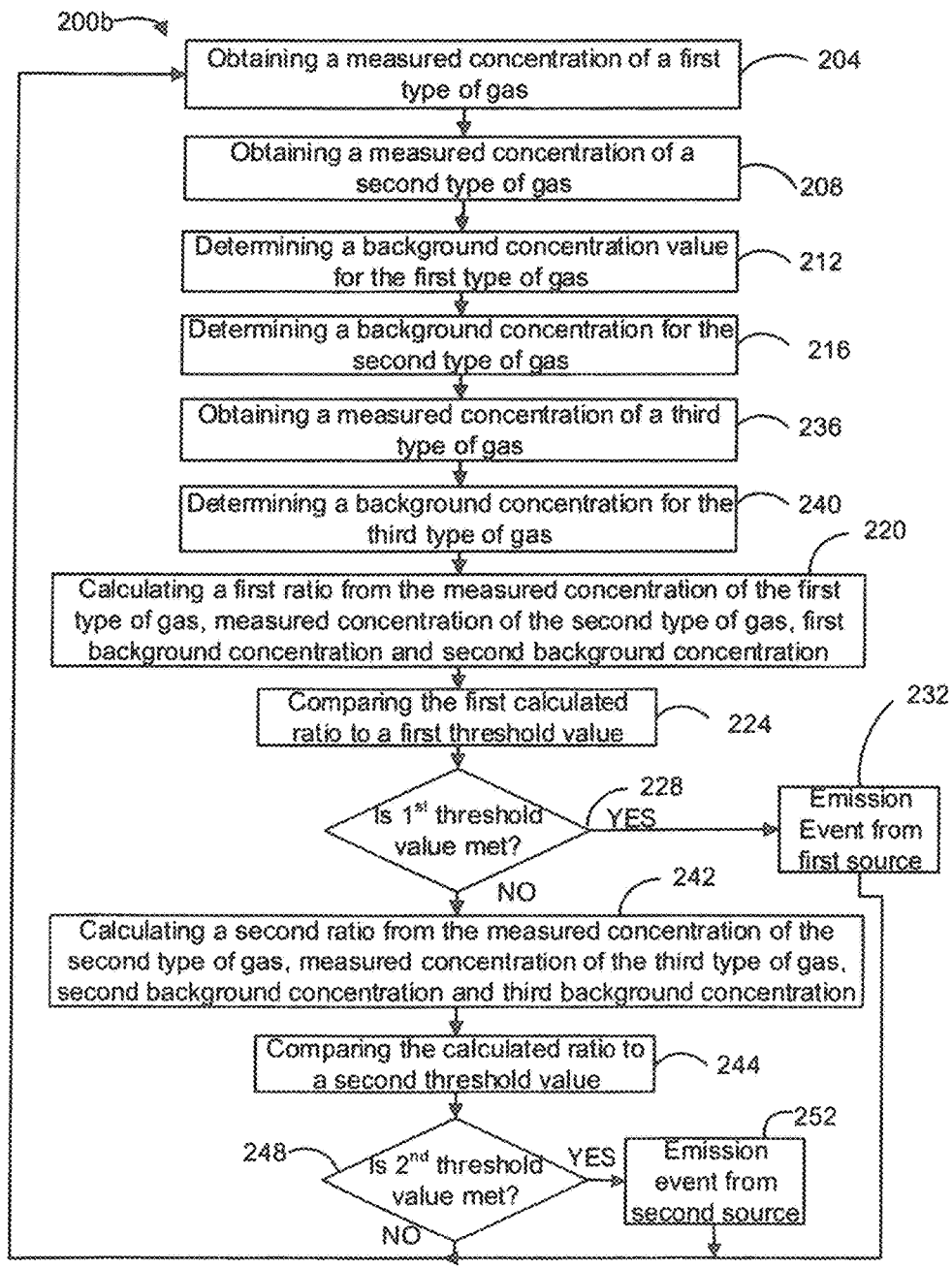
FIG. 4B is a flowchart showing the operative steps of another exemplary method for detecting a gas emission event.

Referring now to FIG. 4B, therein illustrated is a flow chart showing the operative steps of an exemplary method 200b for monitoring emissions at an industrial site. Method 200b is a variant of method 200a in which three types of gases are considered.

In addition to steps 204 to 216, the method 200b further includes measuring concentration of a third type of gas at step 236.

At step 240, a background concentration value is determined for the third type of gas.

At step 228, if the detection ratio does not meet the threshold, the method proceeds to step 242 to calculate a second detection ratio from the measured concentration of the second type of gas, the measured concentration of the third type of gas, the second background concentration value for the second type of gas, and a third background concentration value for the third type of gas. For example, the second detection ratio is also calculated according to the differential calculation described herein.

At step 244, the second detection ratio is compared to a second threshold value. For example, the detection ratio can be compared to a plurality of threshold values, which may correspond to characterizing ratios of different gas emission sources.

At step 248, if the detection ratio does not meet a second threshold, the method returns to step 204 to begin another iteration of the method.

At step 248, if the detection ratio meets the second threshold, the method proceeds to step 252 and it is detected that a gas emission event from the second source is occurring. For example, an alert notifying an operation of the gas emission event from the second source may be issued. The method then returns to step 204 to begin another iteration of the method.

It will be appreciated that according to method 200b, concentration values of three types of gases are measured and two detection ratios are calculated. The two detection ratios can be compared against two or more threshold values to distinguish between two gas emission sources. For example, the first type of gas may be $CO_2$, the second type of gas may be $CH_4$, and the third type of gas may be $H_2S$. In other examples, one of the type of gases, or an additional type of gas may be the isotope $^{d13}CH_4$.

Figure 4C:
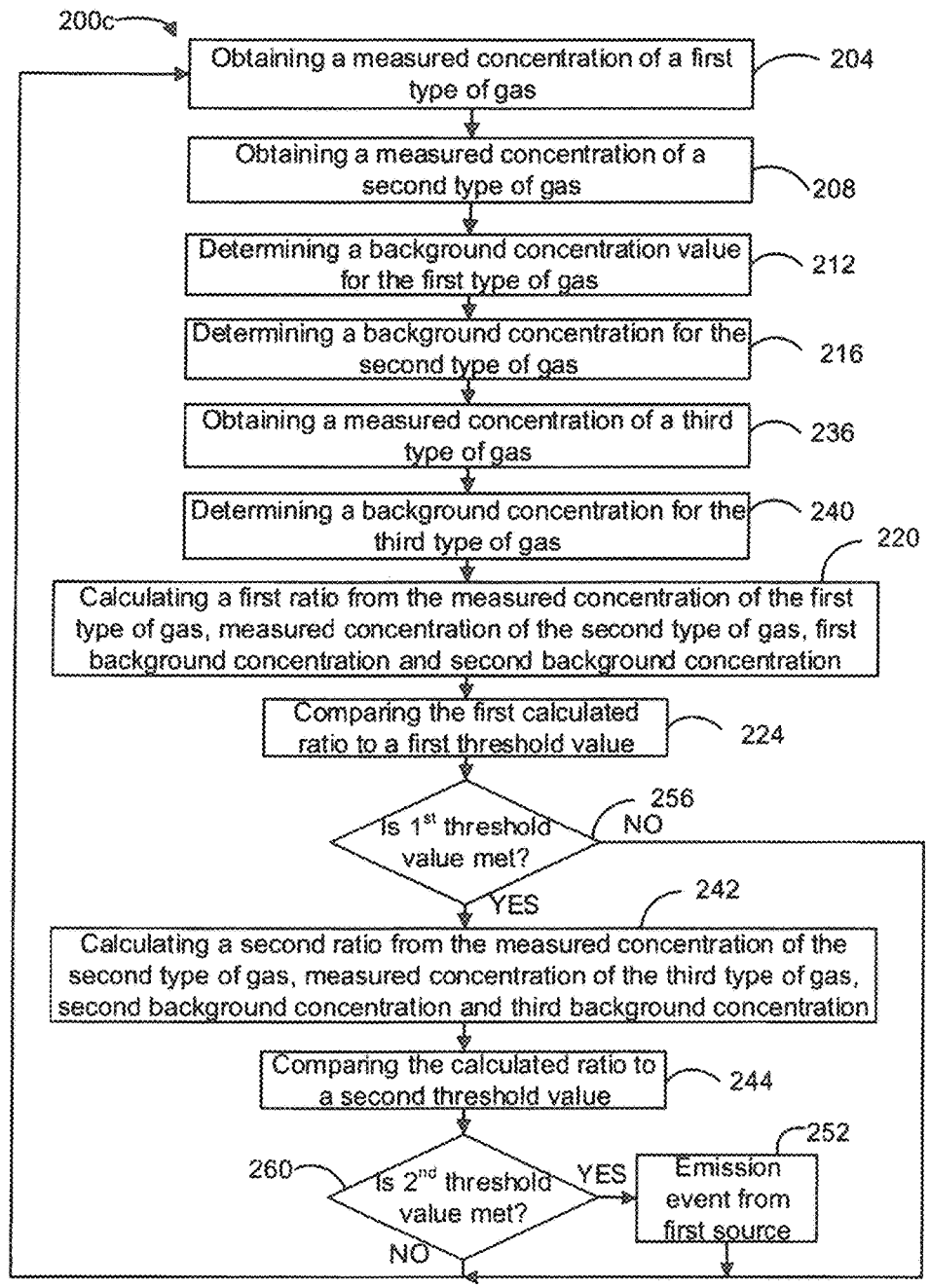
FIG. 4C is a flowchart showing the operative steps of yet another exemplary method for detecting a gas emission event.
Figure 5:
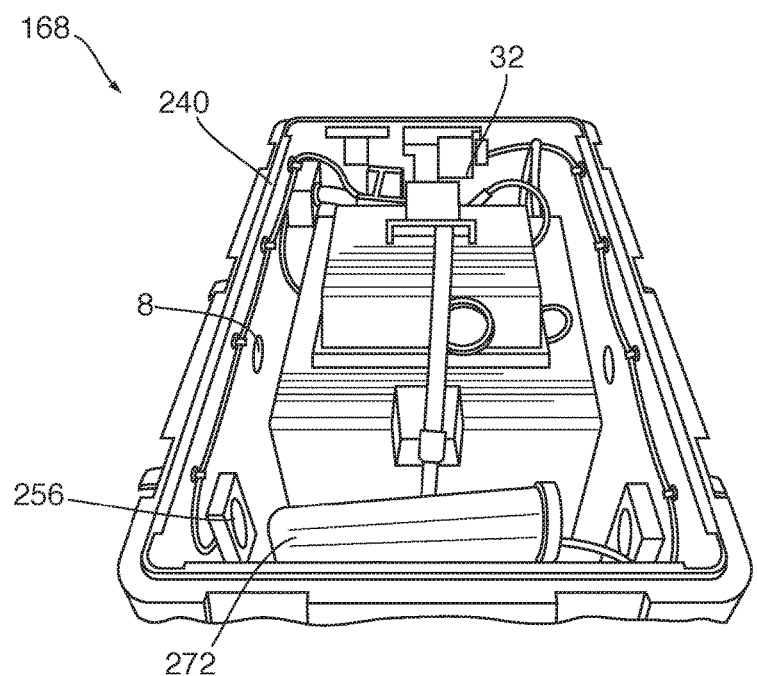
FIG. 5 is a perspective view of a mobile gas surveying device according to an exemplary embodiment in an open state.
Figure 6:
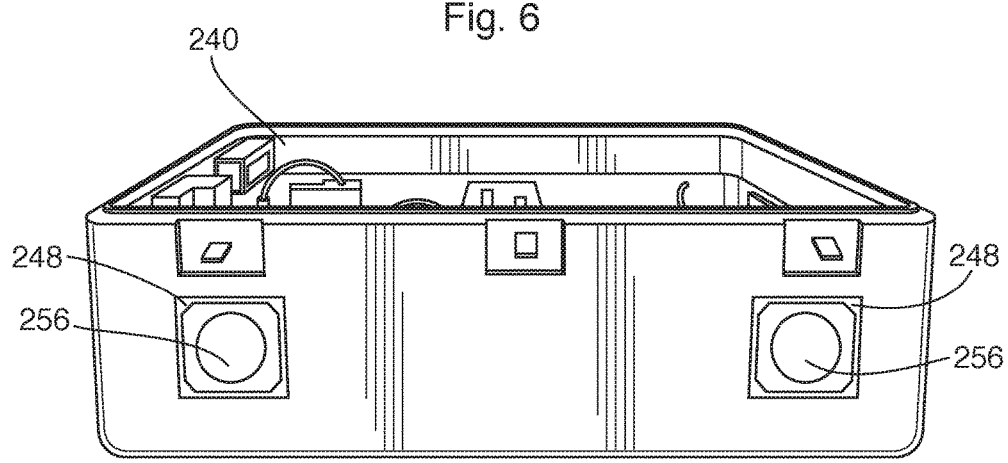
FIG. 6 is a side elevation view of such a mobile gas surveying device.
Figure 7:
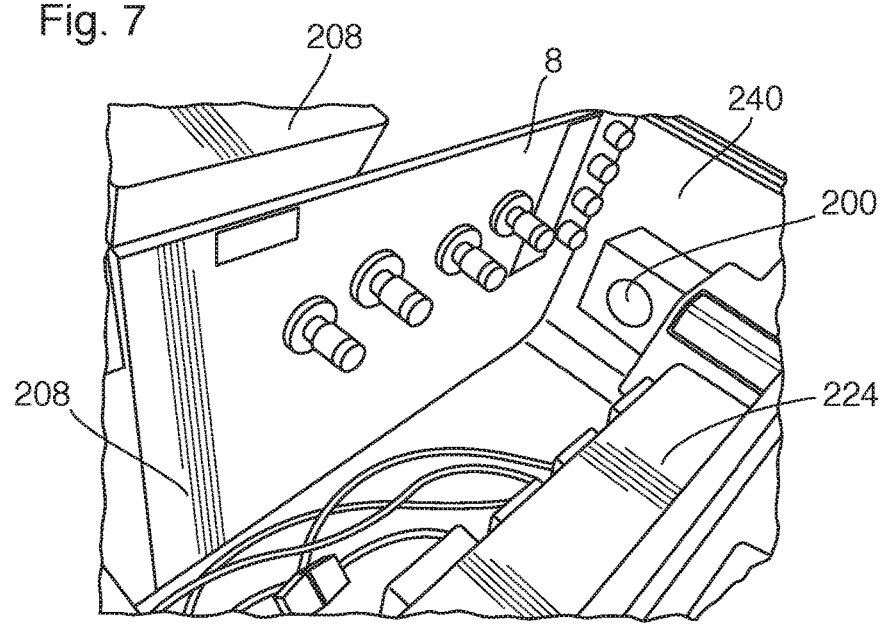
FIG. 7 is a close-up view of a front portion of such a mobile gas surveying device.
Figure 8:
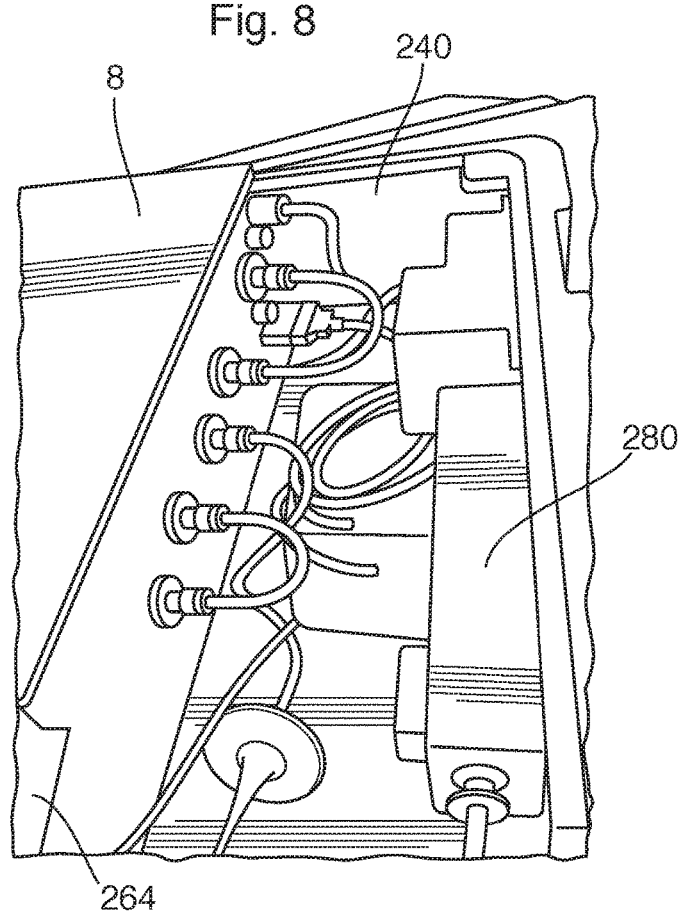
FIG. 8 is a close-up view of a front portion of such a mobile gas surveying device with interconnections of tubes and wires.

Referring now to FIG. 4C, therein illustrated is a flow chart showing the operative steps of an exemplary method 200c for monitoring emissions at an industrial site. Method 200c is a variant of methods 200a and 200b.

After steps 204 to 224 as described herein with respect to FIGS. 4B and 4C, the method proceeds to step 256 to determine if a first threshold value is met by the first calculated ratio. For example, the detection ratio can be compared to a plurality of threshold values, which may correspond to characterizing ratios of different gas emission sources.

At step 256, if the detection ratio does not meet threshold, the method returns to step 204 to begin another iteration of the method.

At step 256, if the detection ratio meets the threshold, the method proceeds to step 242 to calculate a second detection ratio from the measured concentration of the second type of gas, the measured concentration of the third type of gas, the second background concentration value for the second type of gas, and a third background concentration value for the third type of gas. For example, the second detection ratio is also calculated according to the differential calculation described herein.

The comparison at step 224 and 256 may provide a first indicator of an emission event from a gas emission source. It may also provide a first indicator that there is an emission event from a plurality of potential sources. A further comparison using at least one additional gas is used to validate the first indicator and/or to distinguish between the potential sources.

At step 244, the second detection ratio is compared to a second threshold value. For example, the detection ratio can be compared to a plurality of threshold values, which may correspond to characterizing ratios of different gas emission sources.

At step 260, if the second detection ratio does not meet a second threshold, the method returns to step 204 to begin another iteration of the method.

At step 260, if the second detection ratio meets a second threshold, the source of the gas emission event is validated or distinguished. For example, there is validation in that two gas characterizing ratios for a gas emission source have been identified. For example, there is distinction in that where two or more gases have the same characterizing ratio for a pair of type of gases, another characterizing ratio of a different pair of types of gases is used to distinguish between the gases.

It will be understood that according to the exemplary methods 200a, 200b, or 200c, more than two gases may be measured and background concentration values for each of the more than two gases may be determined. From the more than two gases, two or more detection ratios may be determined, for example, using the differential calculation described herein. The two or more detection ratios can then be used to identify the gas emission source from two or more potential gas emission sources. The gas emission source may be identified using only one detection ratio. Additionally, or alternatively, at least two detection ratios may be used for identifying a gas emission source as the cause of the gas emission, whereby after identifying the source as a potential cause based on one or more detection ratios, at least one further detection ratio is used to validate that identification. Additionally or alternative, at least one detection ratio may be used for identifying at least two gas emission sources as potential causes of the gas emission, whereby at least one further detection ratio is used to distinguish between the potential causes so as to identify a unique source of the gas emission.

Referring now to FIGS. 5 to 8, therein illustrated is a perspective view of a mobile gas surveying device 168 according to an exemplary embodiment in an open configuration. The mobile gas surveying device 168 includes a temperature-controlled and moisture-controlled enclosure 240. The enclosure 240 has at least one inlet 248 for receiving ambient air surrounding the enclosure 240. The inlet 248 provides fluid communication between the outside of the enclosure 240 and the interior of the enclosure. The Inlet 248 may have fans 256 mounted onto the walls of the enclosure 240 for drawing air into the interior of the enclosure 240. The fans 256 may also assist in controlling temperature of the enclosure 240, such as by drawing cooler ambient air into the interior of the enclosure 240. The fans 256 may be controlled to turn on when the temperature within the enclosure 240 exceeds a predetermined threshold, such as 25 degrees Celsius.

The mobile gas surveying device 168 further includes at least one gas analyzer 8 disposed within the enclosure. The gas analyzer 8 is operable to measure the concentration of at least one type of gas.

The mobile gas surveying device 168 further includes a plurality of dampeners for reducing shock to the at least one gas analyzer 8. For example, the dampeners may be one or more foam members 264 disposed between an outer surface of the at least one gas analyzer 8 and an inner surface of the enclosure 240. In many cases, the at least one gas analyzer 8 may be a highly sensitive device that has reduced shock-resistance. The dampeners 264 are chosen to prevent damage to the at least one gas analyzer 8 while ensuring proper operation.

According to one exemplary embodiment, the dampeners include a cage member for securing the at least one gas analyzer and spring members providing coupling between the cage member and the inner surface of the enclosure 240.

The mobile gas surveying device 168 further includes a dehumidifier 272 for controlling the amount of moisture within the enclosure 240. The humidity within the enclosure 240 is regulated to a level that permits accurate measurements of concentration by the at least one gas analyzer 8.

The mobile gas surveying device 168 may further include a communication module 32 in signal communication with the at least one gas analyzer for receiving measurements of the concentration of the at least one gas. The communication module 32 is further operable to transmit the measurements of gas concentration to an external device, as described elsewhere herein.

The mobile gas surveying device 168 may further include a data storage unit in signal communication with the at least one gas analyzer for receiving measurements of the concentration of the at least one gas and storing the measurements thereon, as described elsewhere herein.

The mobile gas surveying device 168 further includes a power supply 280 for powering various electrical devices thereof, such as the at least one gas analyzer 8, the fans 256, the dehumidifier 272, the communication module 32 and/or the data storage unit 40.

Figure 9:
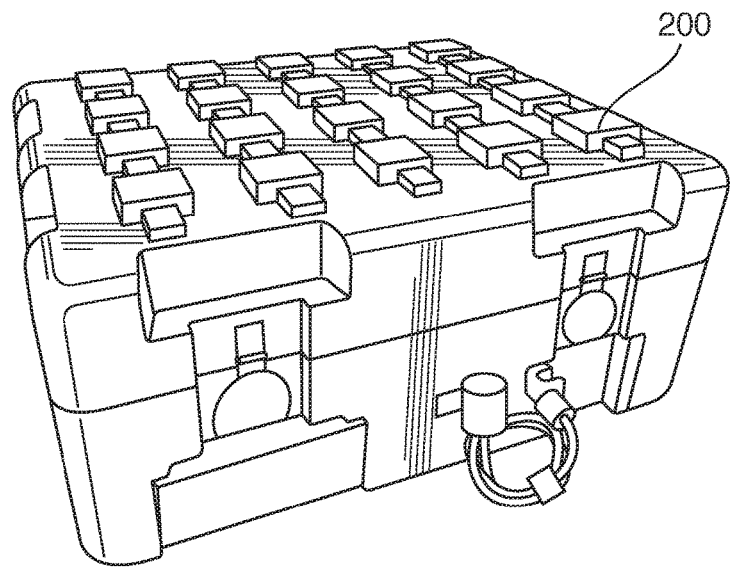
FIG. 9 is a perspective view of such a mobile gas surveying device in a closed state.

Referring now to FIG. 9, therein illustrated is a perspective view of the enclosure 240 in a closed configuration. For example, the enclosure 240 may be a stacking plastic case, such as a stacking military plastic case. When closed, the enclosure 240 defines a substantially closed chamber in which the at least one gas analyzer 8 is disposed.

Figure 10:
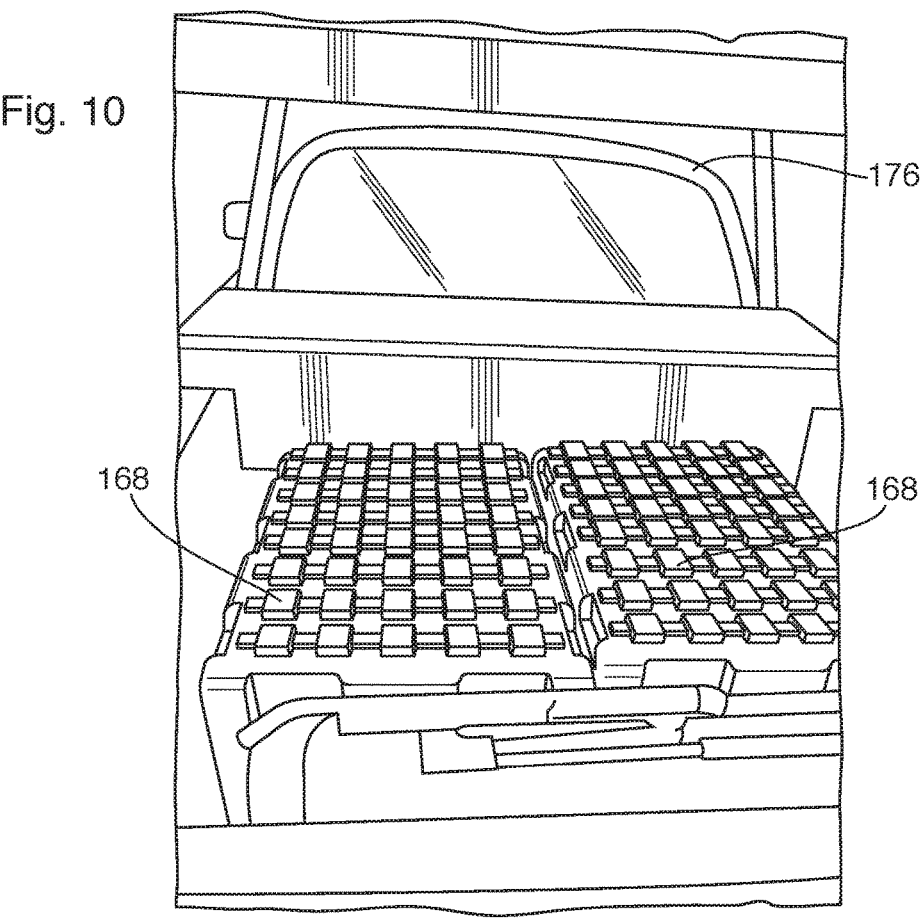
FIG. 10 is a perspective view of two such mobile gas surveying devices mounted onto a bed of a pickup truck.

Referring now to FIG. 10, therein illustrated is a perspective view of two mobile gas survey devices 168 having been placed on the bed of a pickup truck 176. The two mobile gas survey devices may have gas analyzers that are operable to measure concentration of different gases, such as the first gas type and the second gas type.

According to one exemplary embodiment, the mobile gas survey device may include a mounting coupled to the enclosure for mounting the enclosure to a road vehicle, an all-terrain vehicle, a snowmobile, or other mobile carrier. Accordingly, surveying of an industrial site is not restricted to a road network, but may also be carried out in off-terrain areas.

When not deployed in a mobile manner, the mobile gas survey device 168 can be deployed in a stationary manner at the industrial site, such as the stationary device 160.

EXAMPLE 1

A first trial was conducted at a test site in the Canadian prairies. It was observed that excess ratio (eCO2:eCH4; the notation e meaning excess amount over the selected background concentration value) at the test site for leak detection is less than 150, while excess ratio for combustion is above 1000, which allowed for differentiation of these sources.

It was further observed that the background concentration value used for each gas affected correct detection of leaks.

In some environments, the natural background concentrations will vary between topographic positions where air is well mixed or pooled, or where the vegetation is different.

A first test was carried out using a global minimum concentration value. In this example, the minimum concentration value for each gas ($CO_2$ and $CH_4$) from a mobile survey was subtracted from each individual measured. It was observed that use of the global minimum value did not consistently accommodate for changes in the background value of one or more of the gases. When covering large spatial domains, the natural background concentrations varied significantly (e.g. from wetland to a crop land to a residential area).

Figure 12:
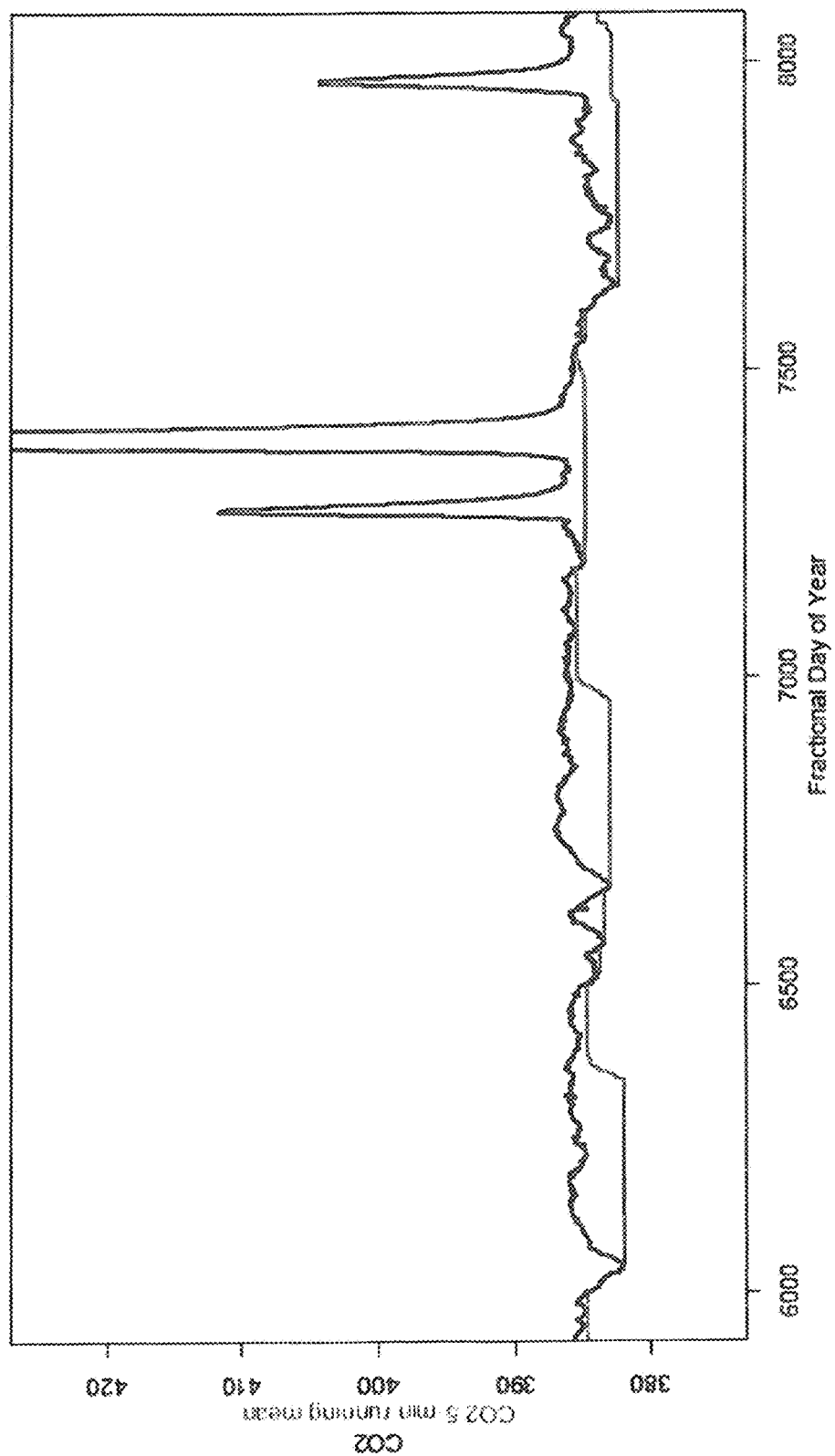
FIG. 12 illustrates a plot of measured concentration values and the running minimum concentration value calculated therefrom according to one example.

A second test was carried out using a running minimum concentration value. It was observed that a desired concentration value corresponded to the temporal frequency of variability characteristics of the landscape. FIG. 12 shows the measured concentration values of $CO_2$ and the running minimum concentration value using a length of time interval of 5 minutes for determining the running minimum value.

It was observed that as currently measured concentration values are falling, the running minimum concentration value is the same as the currently measured concentration value. This can be observed, for example, shortly after time 7500. Accordingly, the calculated difference between the measured concentration value and the background concentration value becomes 0, which results to unstable detection values (i.e. ratios of gases equal 0 or infinity).

Figure 13:
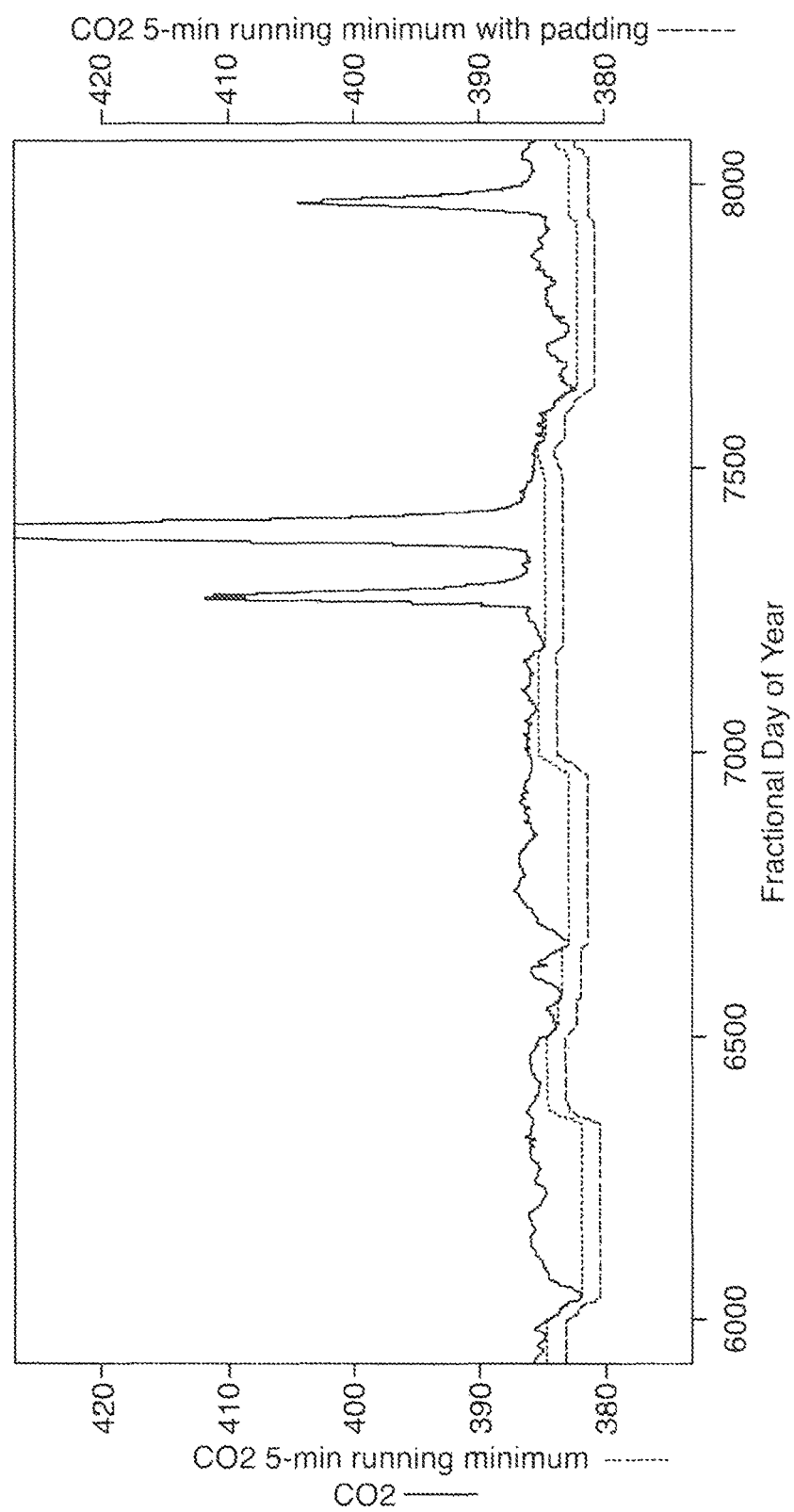
FIG. 13 illustrates a plot of running minimum concentration values being padded according to one example.

In a third test, the running minimum concentration value was "padded", i.e. decreased slightly from the running minimum concentration value. This "padded" running minimum concentration value is then used as the background concentration value. It was observed that the amount of padding should be similar to the natural atmospheric ratio of that gas. FIG. 13 further shows the running minimum concentration value being padded.

It was observed that the number of gas emission events detected varied with both changes in the length of interval time for the running minimum (seconds) and the amount of padding (concentration). According to one exemplary test, the running time interval values were varied from 60 s to 1800 s, in 60 s increments. Padding values were varied from 0.1 to 1.5 ppm $CO_2$ in 0.1 increments, with $CH_4$ padding calculated as $1/215$ $CO_2$ (because $CO_2$:$CH_4$ natural ratio is approximately 215). All combinations of running minimum intervals and paddings were tested, for a total of 450 runs, each one being compared to the global minimum.

It was observed that the running minimum interval affected peak amplitude, and was the main determinant in the number of peaks that exceeded geochemical thresholds. The padding acted differently, to affect the sensitivity in detection (low padding detected earlier), and consequently controlled the width of the peaks.

Figure 14:
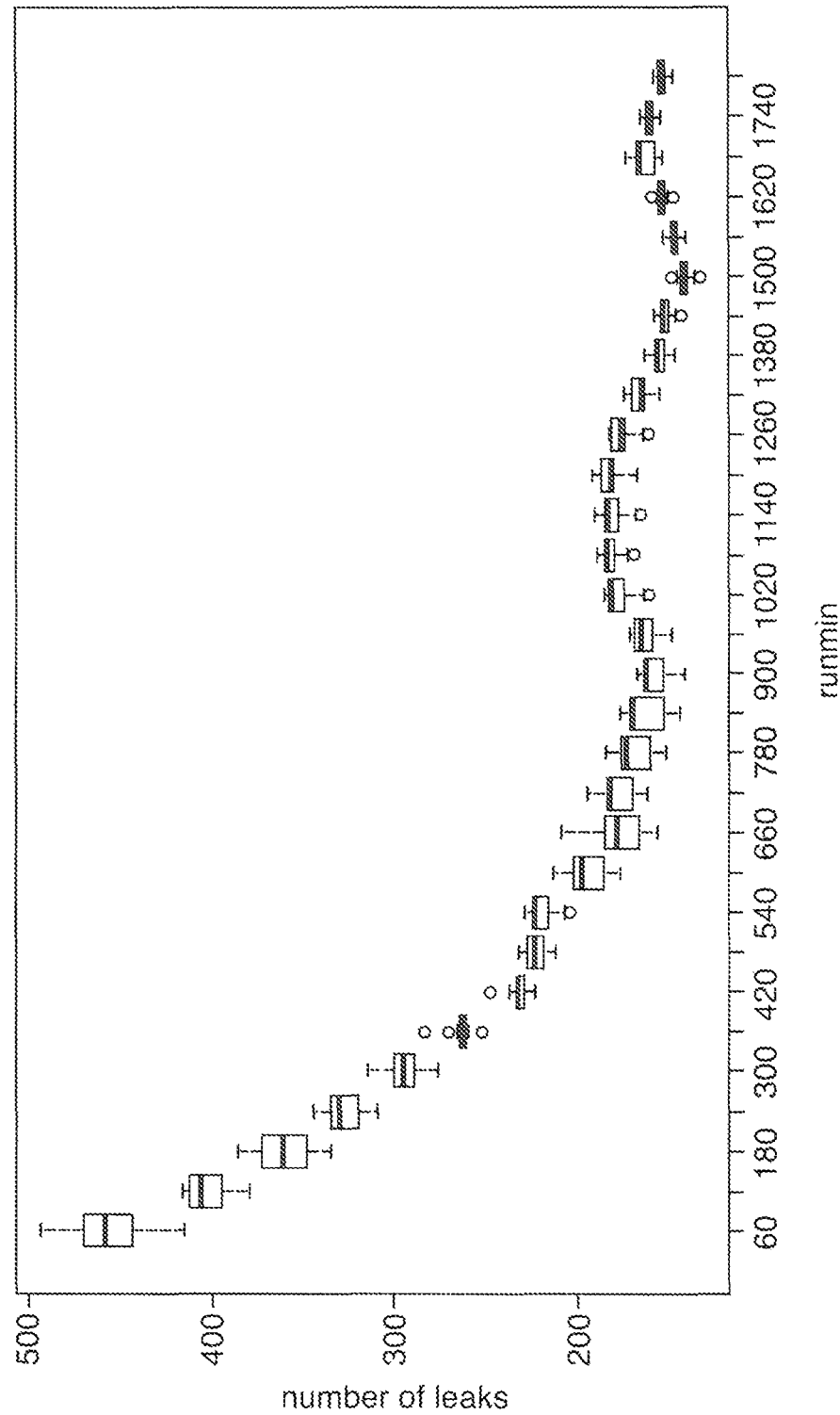
FIG. 14 illustrates a plot showing the number of detected events for various running minimum time intervals according to one example.
Figure 15:
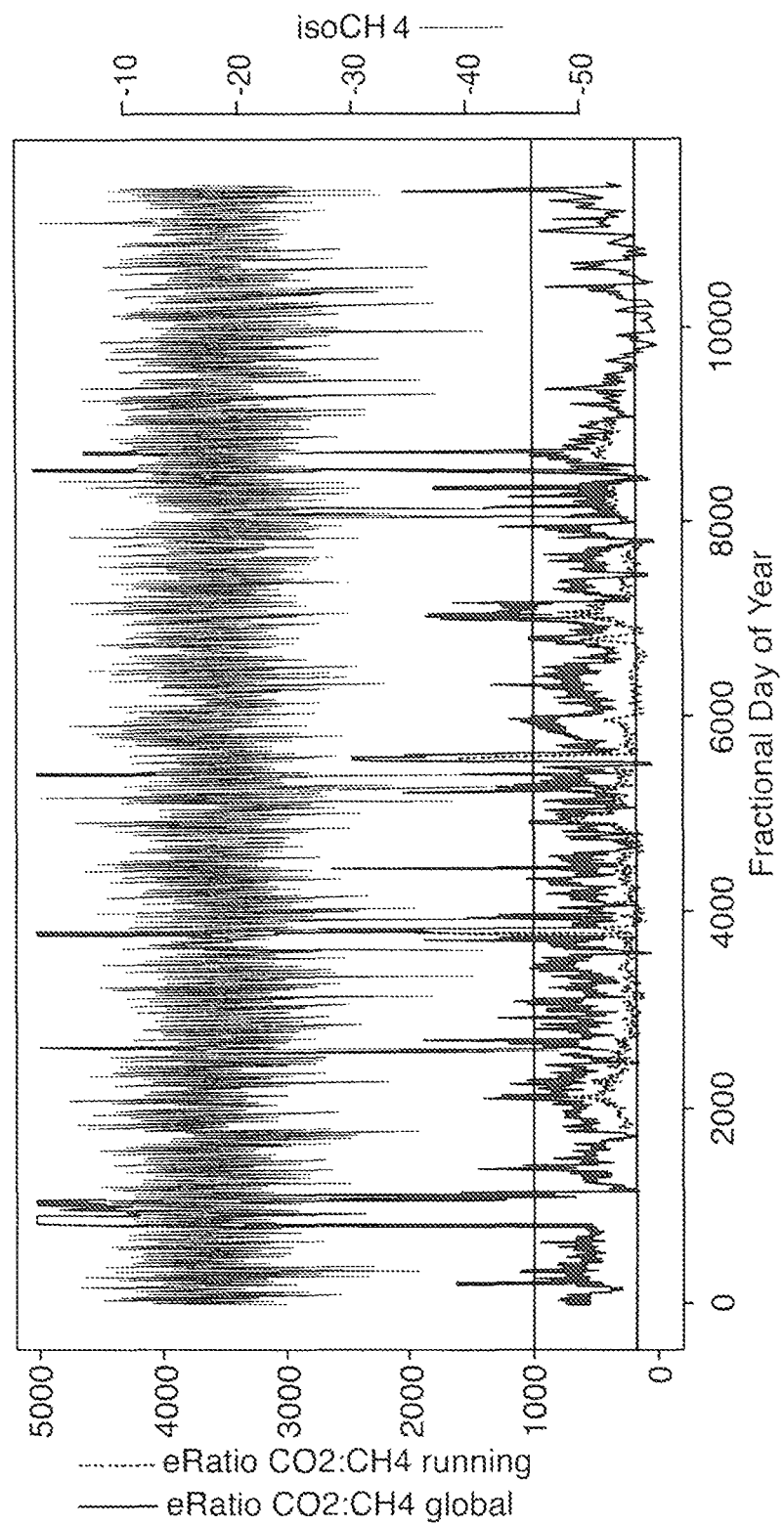
FIG. 15 illustrates a plot of detected events over time for a first location according to one example.
Figure 16:
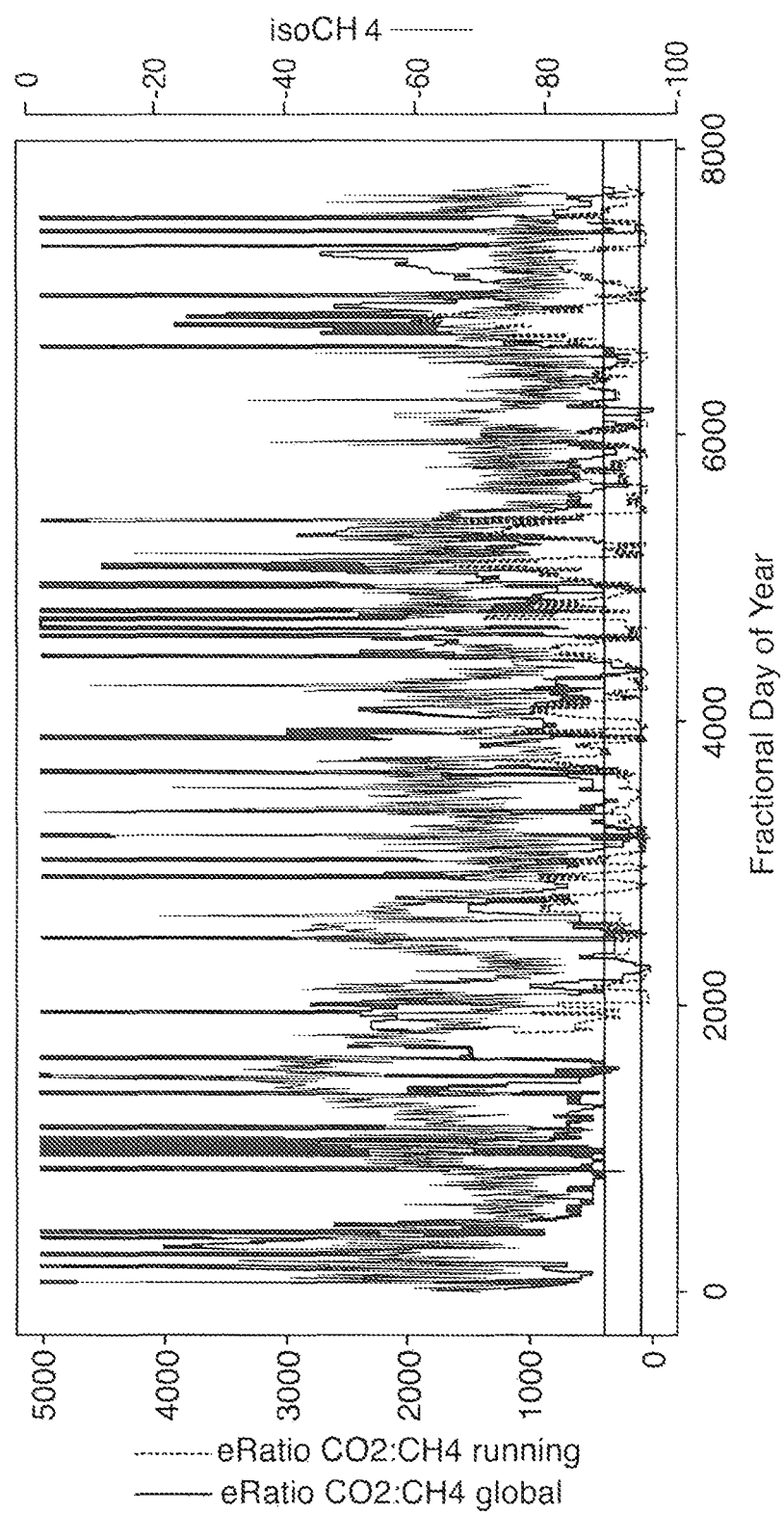
FIG. 16 illustrates a plot of detected events over time for a second location according to one example.

FIGS. 14-16 show the results of some sensitivity tests for several sites. FIG. 14 shows the number of leaks detected for various running minimum intervals. Each dataset showed a progressive increase in the number of peaks/leaks detected as the running minimum Interval was decreased, with a rapid increase at a particular running minimum interval. The boxplots show the effect of all padding values across the range. At low running minimum intervals, the padding took on an important role in determining the number of leaks that were detected. The rapid increase in leaks with decreased running minimum intervals, along with the growing importance of the padding, seemed to indicate instability—where the parameter choices had a disproportionate effect on the leak detection outcome.

Figure 17:
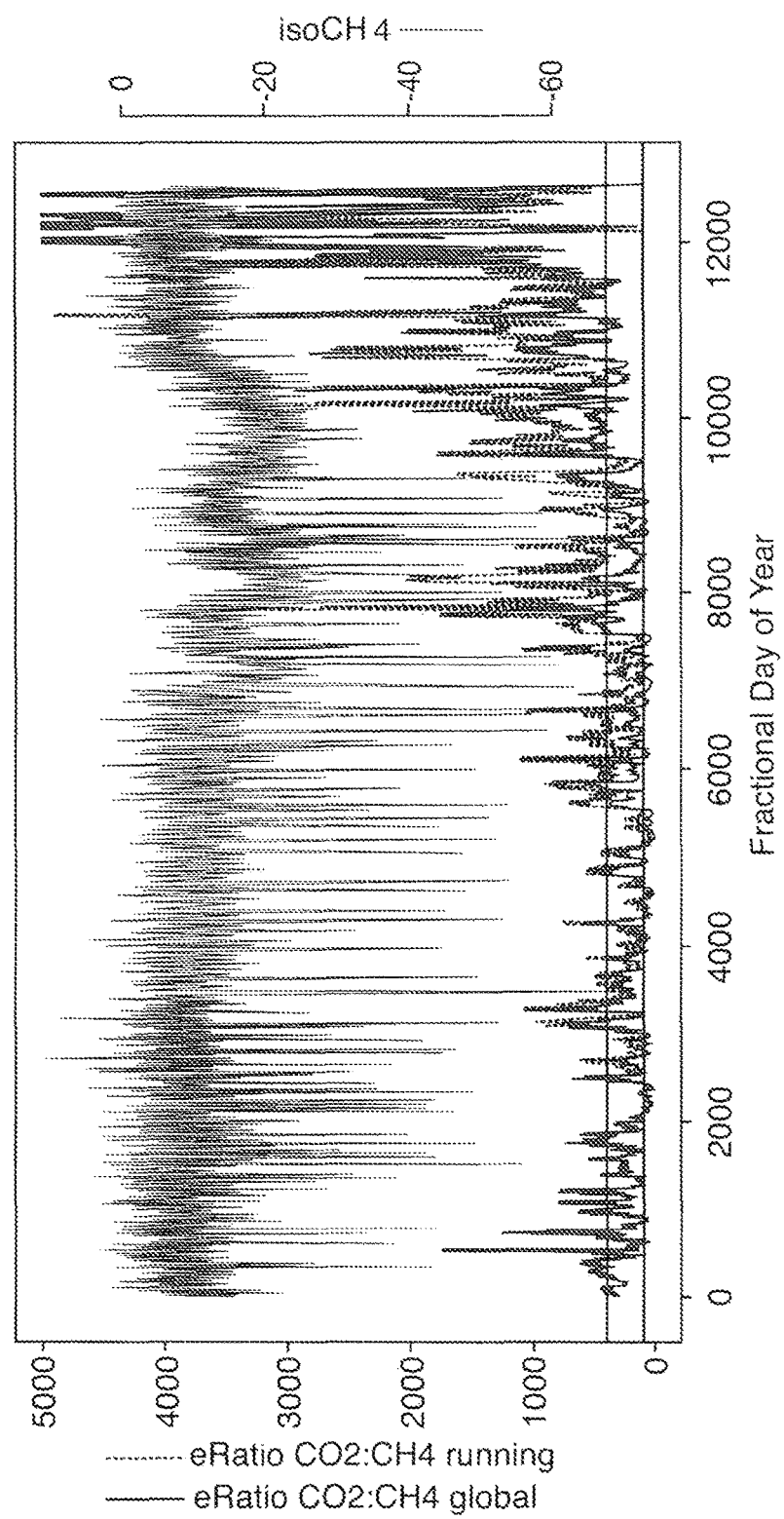
FIG. 17 illustrates a plot of detected events over time for a third location according to one example.

FIGS. 15 to 17 show a comparison of leaks detected at two different sites, using the running minimum and global minimum techniques. The horizontal lines indicate thresholds of geochemical interest in the eCO$_2$:eCH$_4$ ratio, with the upper horizontal line indicating a combustion anomaly, and the lower line indicating some sort of methane-rich anomaly.

In FIG. 15, there is not a great difference between the number of methane anomalies detected, but there are fewer combustion-type anomalies. Both the global minimum eratio (black) and the running minimum eratio (red) both have a steady mean. For this site, the two techniques do not show much of a difference, and the global minimum could be a reasonable choice for simplicity. "eratio" herein refers to ratio calculated from the concentration amount exceeding the selected background value.

FIG. 16, is however, characteristic of a second site where the global minimum eratio drifts over time because of changes in microenvironments over a geographic region. The running minimum eratio in FIG. 16 closely matches isotopic methane data, which is expected the isotopic signature is an independent (from eratio) indicator of leaks.

FIG. 17 shows the comparison for yet another site. Here, there is drift particularly in the global minimum eratio, though the adaptive eratio also drifts somewhat. At any rate, the adaptive running minimum technique is effective at avoiding drift in the eratio.

As the running minimums were mostly affecting the interpretation of leaks within the survey time series, the sensitivity test was used to identify an improved time interval for determining the running minimum time interval. Kurtosis of the resultant distribution was considered, as gases in the near-surface environment tend to take on a Laplace distribution (e.g. double-exponential) with an excess kurtosis of 4. However at some very well mixed sites, particularly in the Canadian prairies, the distributions were far more peaked, and a target kurtosis value representative of natural systems was not sensible.

Figure 18:
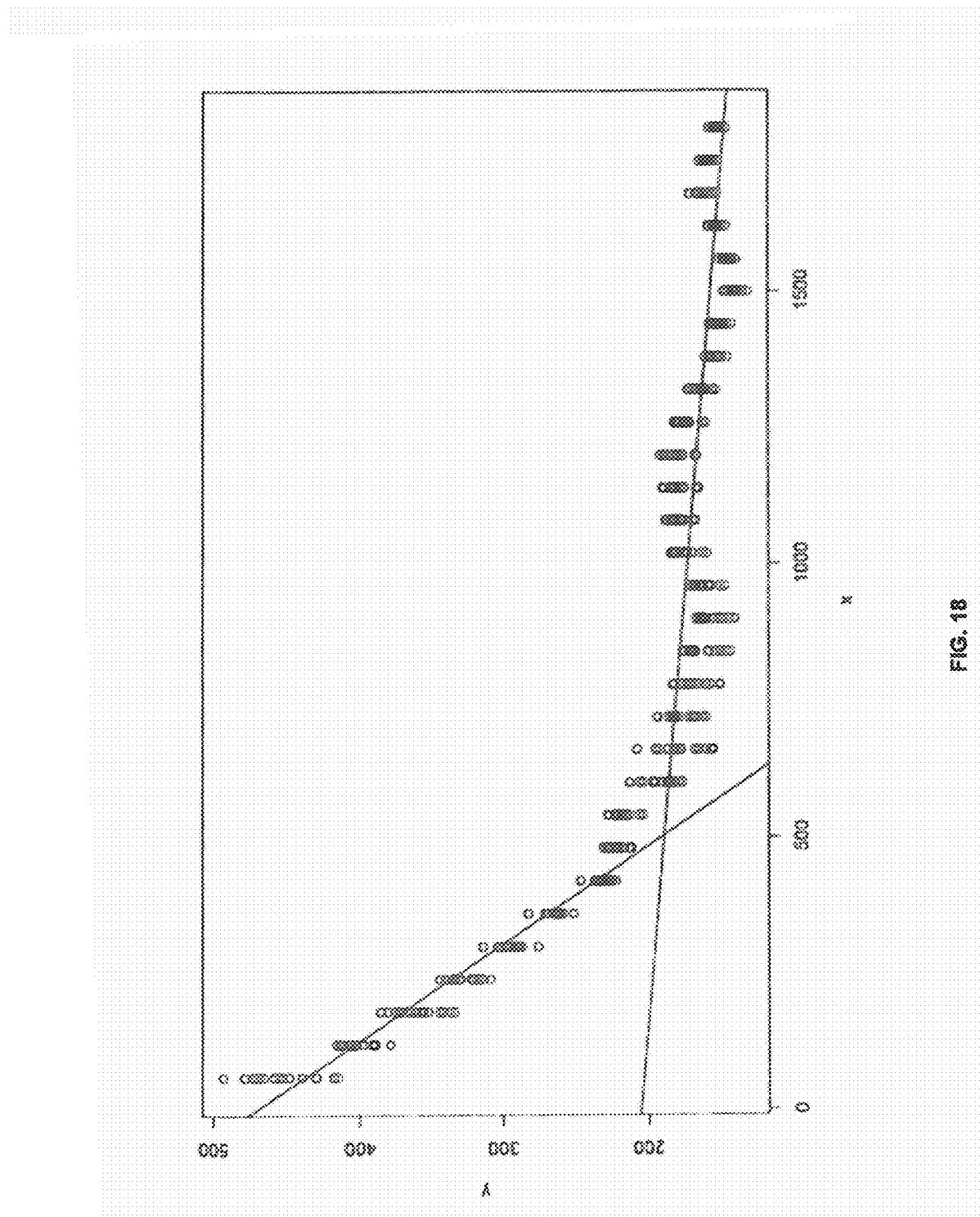
FIG. 18 illustrates a plot showing the number of detected events for various running minimum time intervals with regression lines according to one example.

As the running minimum time interval is generally the main determinant of leak occurrence, an improved running time was sought that would increase number of peaks (or valleys) that would reliably cross the eratio threshold. Reliable herein refers to a particular running minimum time interval where added sensitivity from padding values would not be needed. This approach was taken because it was observed that at the extreme short running minimum time intervals, far more leaks could be identified, but that there was instability in the interaction of the padding and running minimum interval. So, it was desired to aim to increase the number of detected peaks whilst avoiding instability. In order to increase the number of detected peaks while avoiding instability, the break point in the curve between the number of leaks and running minimum iteration was determined (FIG. 18). This is part of a larger attempt to increase the utility of these data. Additionally, steps were taken to properly smooth the data, and to interpolate between skipped measurements. For smoothing, Fourier Fast Transforms suggested that the Picarro instruments provide averaged outputs for some gases, and not for others. In a Picarro 2201, CH$_4$ concentration is actually the longest in averaging time at 1-minute, whereas the CO$_2$ and $\delta^{13}$CH$_4$ are not averaged significantly. If these averaging times are not harmonized, this will have very important effects on leak detection, as the concentrations are moving at different rates—which will create false positives simply due to averaging period. So, all averages are moved to 1 minute. To make this easier, and to fill the irregular 6-7 second gaps in Picarro output, the raw time series were interpolated to provide a temporal interval of 1 s. However, it will be understood that other averaging periods may be used All this work is done before adjustment of the running minimum interval and padding.

The data conditioning and running time adjustment procedure was observed to have significant effects on interpretation of leak sources across the landscape.

Figure 19:
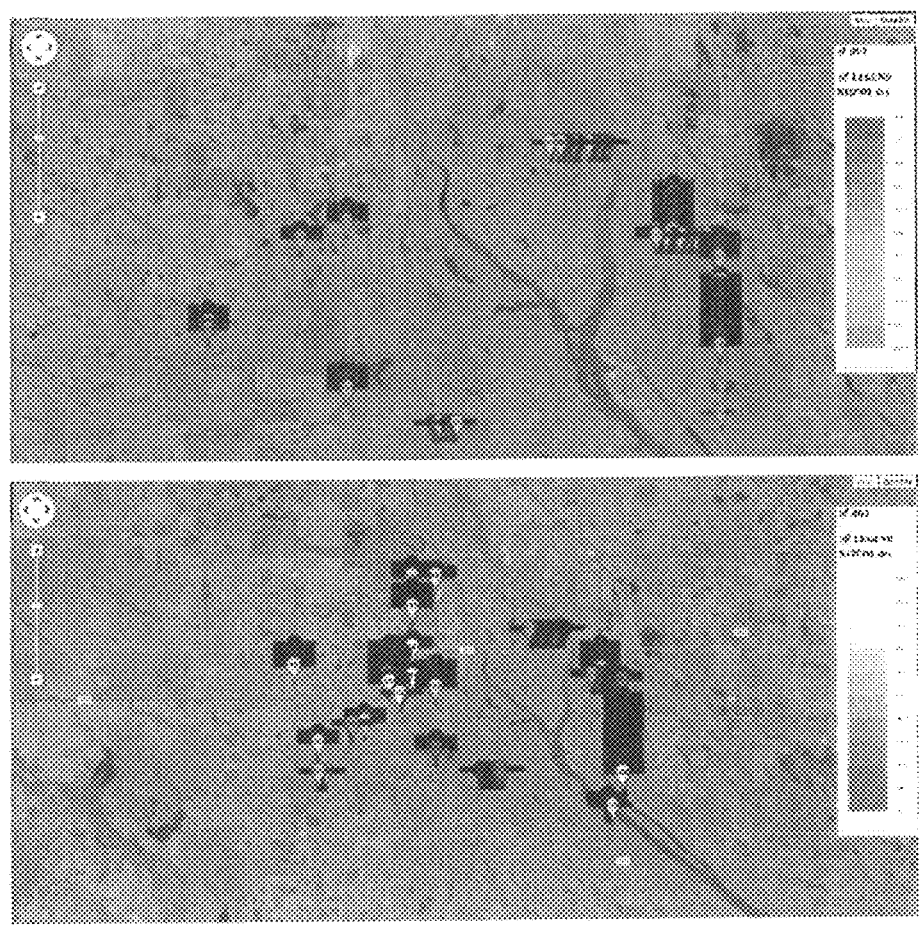
FIG. 19 illustrates maps showing locations of detected events for the first location according to one example.
Figure 20:
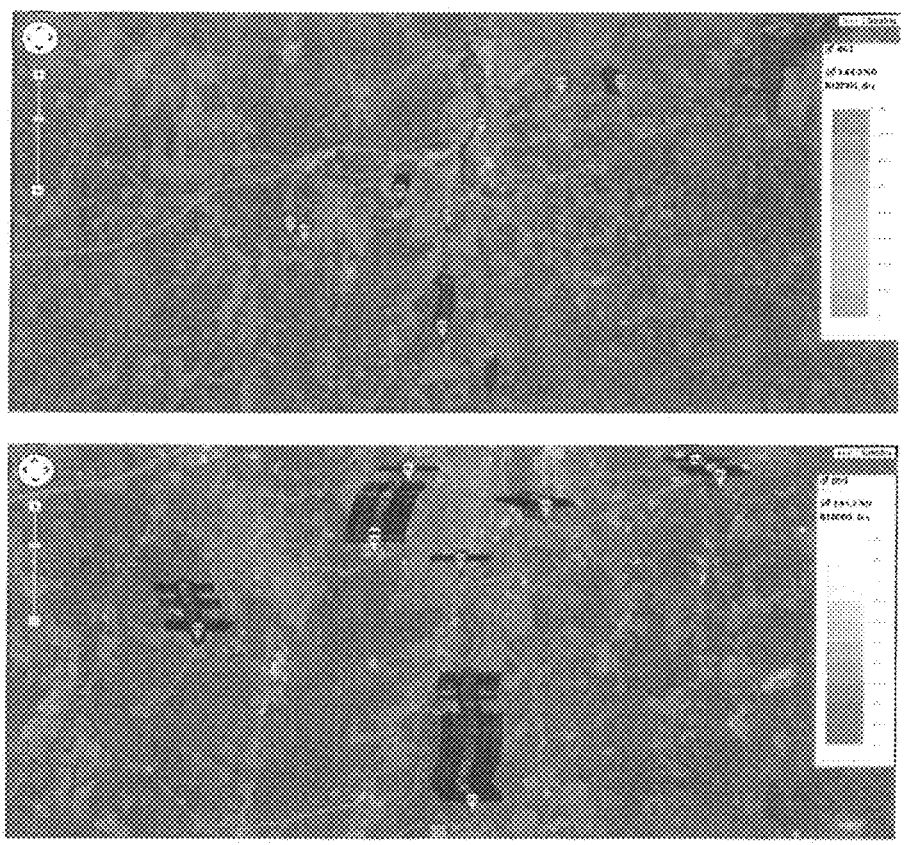
FIG. 20 illustrates maps showing locations of detected events for a second location according to one example.
Figure 21:
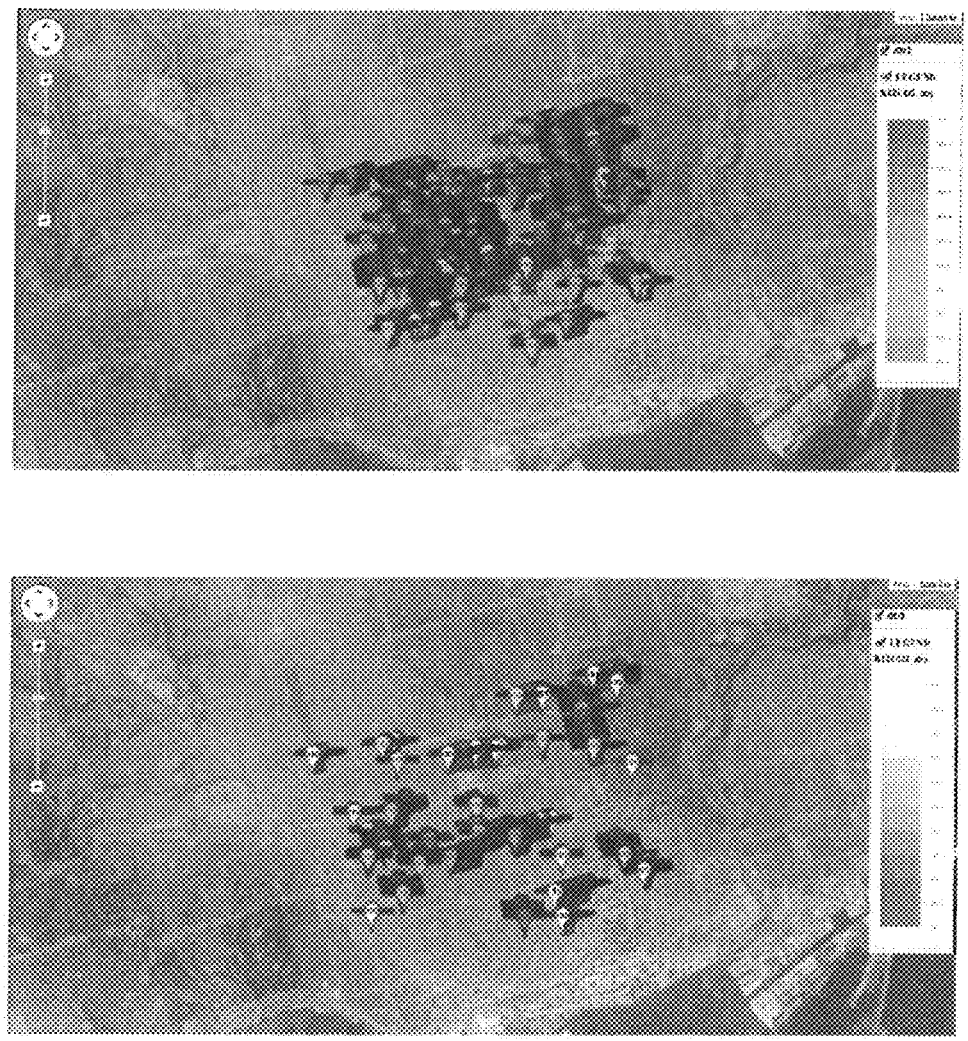
FIG. 21 illustrates maps showing locations of detected events for a third location according to one example.

FIGS. 19 to 21 and Table 1 show results obtained from tests carried out at the first test site in the Canadian prairies, a second test in a large urban city and a third test in the Atlantic Maritimes.

It was observed that resolution of leaks has increased significantly as a result of the above described process. Most of the new leaks observed were small ones. This is not a surprise as the global minimum concentration can fall far below the currently observed value, which erodes sensitivity and drops out most small anomalies. From work with many datasets in different environments, the technique is sensitive without being overly sensitive. The adjustment algorithm allows controlling of resolution, while avoiding instability.

The advantage of this process is that the minimums come from the dataset. This may be preferred because it allows for immediate deployment, though it is important that some of the survey cover relatively un-impacted areas for good reference. Large volumes of baseline data, or atmospheric concentration norms, are not required. This procedure both adds resolution and flexibility to the mobile eratio technique, without adding undue computational bulk. The 450 point adjustment process only takes 1-2 minutes to find the ideal running minimum interval and padding concentrations for 3 hours of survey data, and thus all data to date can be reprocessed easily. The procedure may require a bit of tweaking depending on the ratios and types of leaks expected.

TABLE 1

| Mobile surveys | Leaks with global minimum | Leaks with running minimum |
|---|---|---|
| Test site 1 | 30 | 190 |
| Test site 2 | 94 | 163 |
| Test site 3 | 7 | 48 |

EXAMPLE 2

An exemplary test sensing system consists primarily of two CRDS instruments to measure low-level atmospheric anomalies in the large domain of the first test site. They are used in alternating mobile and stationary deployments, along with a web-based computing infrastructure for visualizing and communicating results to project stakeholders. Remotely sensed and operator data are harvested that aid in the process of differentiating natural and industrial signals. Testing was carried out during mid and late growing season 2013 at the first test site. Although tested on an EOR site in this study, the system also has applicability to shale gas or other industrial sites.

There are several gases that are associated with infrastructural leakage at EOR sites, including CO$_2$, CH$_4$, H$_2$S, and $\delta^{13}$CH$_4$. Carbon dioxide is a logical detection target because high volumes are injected into this EOR reservoir, though CO$_2$ also happens to be highly variable naturally and is generally not an adequate metric for leak detection on its own (Risk et al., 2013). Methane is ubiquitous in oil and gas developments, and is associated with leaks of many types. Its isotopic ratios are useful in leak detection, for distinguishing $CH_4$ of surface biologic origin, from fossil fuel sources of thermogenic origin (Quay et al., 1999). Hydrogen sulfide (also known as "sour gas") is a common constituent of oil and gas bearing rocks that can be associated with leaks, but advantageously has a comparatively small atmospheric abundance and weak natural sources in terrestrial settings. On their own, these pure gases do not constitute reliable targets for identification of leaks, because natural sources near the earth's surface may compete with or damp the observed concentration anomalies. However, as EOR leaks emit all of them simultaneously, the ratio of gases can provide a rather more reliable indicator of leakage, similar to Romanak et al. (2012). Rather than Individual targets, gas ratio "fingerprints" were used to identify leaks.

Table 2 lists the approximate $CO_2$, $CH_4$, and $H_2S$ gas mixture fingerprints of the possible leakage sources in the field. The source gas for the EOR operation at the first test site is from a few kilometers to the south. This coal gasification plant emits a relatively pure stream of $CO_2$, but containing small amounts of $CH_4$ and $H_2S$ (Trium, 2011). Gas is not injected directly into the formation, but is mixed beforehand with gases separated from the oil/groundwater stream at producing wellheads. Gases in these produced fluids are typically composed of $CO_2$, with some $CH_4$, and non-trace quantities of $H_2S$ owing to the sour nature of the formation. This mixing happens in any one of dozens of mixing huts within the field and the resultant Recycle Gas (REC) is pressurized, and sent underground toward the formation. Over the long timeframe of injections (upward of 12 years), the REC have come into relative equilibrium and now have relatively similar fingerprints as $CO_2$ has built up in the reservoir. Many studies have been concerned with the long-term fate of injected $CO_2$ (Mayer et al., 2013; Shevalier et al., 2013) and it has been shown that wells (and probably Injection wells) are the most likely source of $CO_2$ leakage (Bowden et al., 2013). Since these wells carry REC gas, the REC-type composition is the main focus in leak detection. Additionally, REC and formation-type gases of similar composition are also released during specific drilling and maintenance events, and REC is therefore a tracer of subsurface leakage but also the overall degree to which the operation contains these gases.

Non-industrial emissions come from the natural environment. Soils are a continuous source of $CO_2$, which originates from decomposition of organic residues left from the last growing season. Some root respiration also contributes to soil $CO_2$ production. These emissions are climatically dependent, and are also offset by leaf uptake of $CO_2$ during the growing season, making for complex annual patterns of $CO_2$ variability at the surface. Aerobic soils are generally thought to be a sink for $CH_4$. Reducing wetland soils are a source of $CH_4$ and possibly some $H_2S$. Overall, these terrestrial ecosystem signals pose a problem for leak detection efforts, because they contribute to significant spatiotemporal variability in these gases.

Nickerson and Risk (2013) suggest a simple process for determining the signal to noise ratio (SNR) of gases for leak detection, to help choose targets that augment the likelihood of detection. The technique weighs the natural sources and variability (noise) against the industrial emission of interest (signal). Generally, gases like $H_2S$ will make good targets owing to their relative rarity in the natural atmosphere (<1 ppb), but reasonably high concentration in leak plumes. Nickerson and Risk (2013) have showed that naturally abundant surface gases like $CO_2$ make comparatively poor detection targets (Nickerson and Risk, 2013), though other authors argue that resolution can be improved significantly when a ratio is made with another gas (Romanak et al., 2012). Including atmospherically rare detection targets, along with more abundant gases, may improve specificity of leak detection.

In order to isolate the diluted anomalies, a method of background subtraction to isolate the "excess" ($eCO_2$, $eCH_4$ in notation) concentration that is attributable to a parcel of air released from an industrial process. The background contribution needs not be identified through the collection of long-term atmospheric data, but can be identified from within the dataset itself. As the probability of detecting a leak is low, particularly on the upwind side of the field, and because the domain is large and leaks cannot spread themselves uniformly across the whole domain, a substantial portion of the air measured during a vehicle-based survey will reflect only the contribution of large scale background, plus localized natural sources (vegetation and soils), and will be free of contributions from the oilfield environment. Thus the domain can be surveyed and one can identify, from within the survey dataset, a background minimum value for each gas. One can also determine the ratios of background gases in this manner. As the natural sources fluctuate in time, one can assume that this background minimum value will be valid for a short time interval, but should be reasonably stable for the entirety of a 2-h survey. For simplicity, one can also assume that the background is constant over the domain during the interval, and this assumption is reasonable in a well-mixed environment, which has flat topography, moderate winds, and a small number of land use types. In more complex and varied terrain, background estimation is more complex, and can be computed as a variable quantity throughout the survey, for example as the minimum of the last five minutes. As most plumes are traversed quickly by the vehicle and only register for some tens of seconds, and because it is improbable to be continually reading a single plume (especially if surveying cross-wind), a variable background approach is reasonable. One major advantage of this technique is that background normal and long-term continuous monitoring are not required in order to isolate small leaks. The background values are very specific to the day and time of data collection.

The gas analyzers employed within the context of this study monitor the mixing ratios of atmospheric trace gases based on the cavity ring-down spectroscopy (CRDS) technique. The test CRDS configuration consisted of two Picarro trace gas analyzers (Picarro Inc, Santa Clara, Calif. USA), a G-2201i and G-2204 CRDS analyzers for monitoring $CO_2$, $CH_4$, $H_2S$, as well as $\delta^{13}CH_4$ (the stable carbon isotopic signature of $CH_4$), respectively. According to manufacturer specifications, the mixing ratios of these species can be measured with an accuracy of several ppb depending on species. Instruments were calibrated for concentration against internal standards regularly, typically at the start of every vehicle survey. Internal standards were benchmarked by gas chromatograph (Varian with TCD and FID) against NIST-traceable reference standards (Matheson Gas). The data acquisition frequency of the CRDS instruments was 1 Hz.

In stationary mode, the CRDS instruments were deployed at the industrial site within the injection field, located just 10 km west of an industrial plant. The Instruments were housed inside thermally-regulated water resistant boxes which have allowed the instruments to measure in conditions ranging from −30° C. to +35° C. over the deployment period. The test stationary survey device monitored multiple trace gas species at a 2 m above ground height (m.a.g.h), which would be very low for ecological monitoring purposes but suits current environmental monitoring application.

The function of the stationary survey devices was to continuously monitor temporal variability of trace gas ratios in a central position of the facility. The variability of captured signals within the EOR field was a function of the field of view of the gas analyzers, the so-called footprint function, which depended on the wind direction and atmospheric turbulence conditions, as well as the changing composition of sources and sinks for the target gases within this field of view, and their temporal variability. Since the spatial extent of mixing ratio footprints can cover large areas, it is likely that multiple emission sources for each particular target gas were influencing the observations at each particular time, each with individual spatial distribution and flux densities. Due to this fact, it was expected a certain amount of basal variability within the observations of the stationary system may not be attributable to any one source. When significant sources did exist, they rose above this variation, and this basal "noise" was registered in gas $eCO_2$:$eCH_4$ ratios, and was particularly evident if the leak was nearby.

For these mobile surveys to measure spatial variability of multiple gas species at the regional scale, the CRDS instruments described herein was transferred to a vehicle, for sampling air in real-time as the vehicle was driven along a prescribed route. Air was drawn to the analyzers from a filtered intake mounted at the windshield (mean height ~1.5 m) at a rate of 5 lpm to reduce the in-tube lag time. Before and after each mobile survey, standard tanks were used to establish instrument drift.

The routes were chosen to cover as much landscape and as much infrastructure as possible within a 10 km×10 km field. Road access in this field is excellent, with a grid-like structure of highway and agricultural roads. Global Positioning System (GPS) information was logged during each survey using Garmin Forerunner devices logging at 1 Hz. The average survey travel velocity was ~70 km h-1, which, combined with sample frequency of 1 Hz, results in a sampling resolution of ~20 m. Each mobile survey took just over 2 h to drive within and around the industrial site (~140 km). During a typical drive, roughly 8000-9000 geolocated concentration measurements for each of $CO_2$, $CH_4$, $H_2S$, and $\delta^{13}CH_4$ were logged.

Various campaigns were carried out. Each campaign included as much as 1000 km of mobile survey data. Nighttime surveys generally started at 9 pm, while daytime sampling was done opportunistically during the day around other work.

FIG. 22 shows concentration and variability recorded at the stationary survey device. The following procedures were used to analyze the stationary data. All techniques are highly automated and supported by computing scripts due to the volume of data, and need to integrate different streams including GPS, CRDS (2 in some cases), and meteorology. In 2013 and 2014, tens of millions of concentration values cumulatively recorded from the stationary and mobile units at the first test site. Stationary trace gas observations were initially screened for leak anomalies by analyzing both variance from the background, and by $eCO_2$:$eCH_4$ ratios or similar, in three steps using the 1 Hz CRDS trace gas data. A script computed 3-min means and variability for trace gas species, followed by flagging of 3-min intervals exhibiting excessive variability, as the movement of plumes across the stationary site were usually short lived (seconds to minutes) owing to normal shifts in wind direction. Lastly, plots of the dominant wind directions and speed were attached for comparison. These criteria helped indicate the presence of leak anomalies passing the survey device, though the anomalies could have also in some cases originated from poorly mixed air or natural emissions. The next step was to examine ratios of gas excess concentrations to determine if their proportions matched the known proportion of the industrial gas sources. Using these data, reasonable records of natural background concentrations could be provided by filtering out all industrial anomalies tagged either by variance, or by excess ratio. These background stationary data may provide a useful foundation for future atmospheric studies at this site.

For mobile spatial distributions and visualization were prioritized over time series statistical properties. Each mobile survey device data point was tagged with geographical coordinates and other ancillary data were used to produce visualizations. These visualizations allowed for consideration of the spatial context of measurements, including infrastructural and environmental influences.

Figure 23:
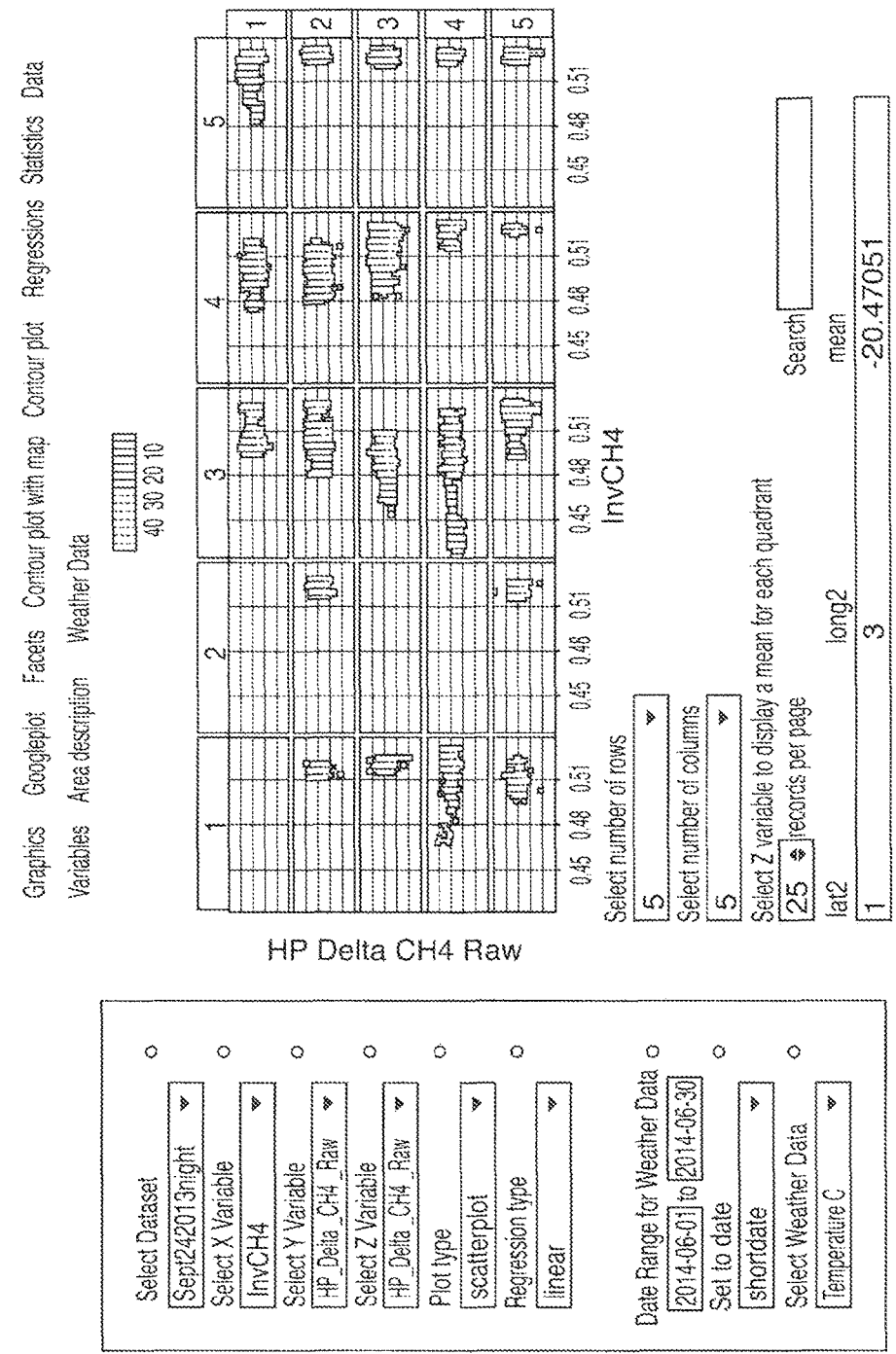
FIG. 23 illustrates an interface for the test survey having a Keeling plot.

Referring to FIG. 23, both mobile and stationary data were organized through an analysis visualization interface. For the mobile data, this also involved several dynamic maps with overlays of gas species concentrations ($CO_2$, $CH_4$, $H_2S$, $\delta^{13}CH_4$). Other interfaces and mapping applications may also be used. Based on the mobile high frequency raw datasets, excess gas ratio fingerprints on a coarse spatial grid (e.g. 2×2 km resolution) were aggregated, where results were displayed through a grid of scatter plots, each representing typical gas proportions sampled within a longitude-latitude sub-domain. This allowed for identifying sub-domains exhibiting unusual concentrations and ratios of gases.

To merge the datasets and launch the visualization interface took roughly 1-2 h, as much of the process was automated. The visualization interface allowed for discriminating potential leaks on the basis of ratio, and map emission events captured during mobile surveys. Often, this rapid analysis permitted a same-day return to the location for further screening, working upwind to locate the source of any anomalies.

Figure 24:
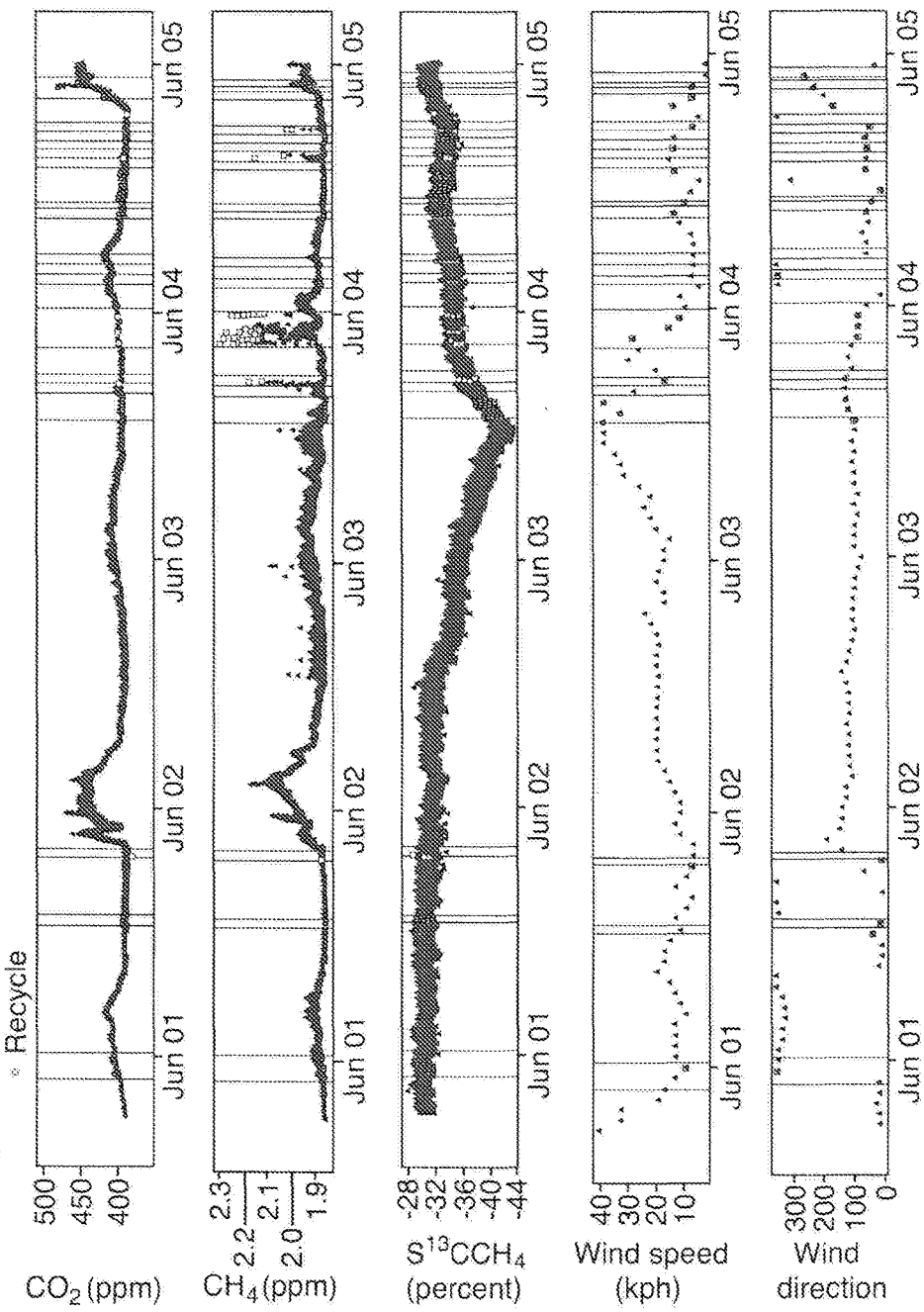
FIG. 24 illustrates plots of stationary time series data for the test survey.

An example of a stationary time series data is presented in FIG. 24, which shows the variability of $CO_2$, $CH_4$, and $\delta^{13}CH_4$, winds, and $eCO_2$:$eCH_4$ over a 1-week period during the summer of 2013. The majority of the data for this time period occur within a range of 400 to 480 ppm $CO_2$, and 1.8 to 2.3 ppm $CH_4$. There are several features of interest in these figures.

The first important feature is nocturnal and daytime differentiation. The raw time series of $CO_2$ mixing ratios from the stationary survey device were clearly dominated by the strong nocturnal buildup of near-surface trace gas concentrations at night-time. These night-time peaks typically exceeded the daytime concentrations by 50 or more ppm, and were caused by low horizontal wind speeds and stable atmospheric stratification that prevented vertical mixing of surface emissions with air masses higher up in the atmosphere. In some cases, nocturnal buildup above 200 ppm $CO_2$ (not shown) were observed. The same patterns can be clearly seen in the $CH_4$ time series, and they generally increased and decreased proportionate to $CO_2$ under the nocturnal boundary layers. A strong covariance (r2>0.7, data not shown) between hourly emissions of $CO_2$ and $CH_4$ were observed, emphasizing that this atmospheric transport mechanism affected all monitored gas species alike, and regularly led to the higher nocturnal trace gas concentrations. Based on these data, one can predict that concentrations of all surface-emitted gases will be more intense during the still nights owing to nocturnal buildup, and therefore one would also expect oilfield $H_2S$-related odour complaints, for example, to increase significantly during early portions of the night when people are undertaking evening activities outdoors during the early buildup phase.

The shaded areas in FIG. 24 show the $eCO_2$:$eCH_4$ anomalies. Focus was put on 3-way partitioning, to discriminate between natural background, combustion ($eCO_2$:$eCH_4$>1000) and reservoir or recycle gas ($eCO_2$:$eCH_4$<50). Combustion anomalies were frequently detected, from every wind direction, and these occurred normally during the workday, all of which were expected. The main exception was the first combustion anomaly on June 1 late in the evening and until roughly midnight, which followed a slackening of winds and a shift of the wind to a northerly direction. Despite similar wind speeds and directions after midnight, which anomaly disappeared, likely the result of stopping some upwind process or drilling activity. At times, oilfield activities extend beyond the regular workday. Correlation of all stationary detections with company activities, particularly combustion-related was not attempted, because these sources are not of primary interest. They could even originate from a generator or vehicle idling near the stationary equipment. The main interest is in reservoir-type gases associated with the Recycle gas stream, which is a mix of gas $CO_2$ and reservoir gas. In FIG. 24, these anomalies are shown in red. It is clear that anomalies of REC type occur when winds are from the east to southeast (10°-90°), which is consistent with the test location about 500 m to the west-northwest of the oilfield's large primary recycling and pumping station. Here, one would expect some small occasional emissions of REC-type gas. Some of the combustion-related emissions come from this direction also, which is consistent with the flaring activities. From this stationary location, REC-type anomalies associated with drilling and other activities in other directions were also identified, in some cases over 2 km away. Normally REC-type anomalies were not associated with extremely high $CH_4$ levels, which suggests that this operation is quite well sealed and does not contribute to atmospheric emissions with the same magnitude of other energy developments (e.g. Pétron et al. (2012)).

$H_2S$ data were also collected and gas analysis on these trends was performed, which reinforced those shown in FIG. 24. Overall, the stationary data helped to confirm that $eCO_2$:$eCH_4$ partitioning was effective and led to logical and predictable patterns of detection. Even at low concentrations of $CO_2$ or $CH_4$ that would not seem particularly anomalous for either an oilfield or natural environment, it was possible to clearly resolve plumes of different types (REC- and Combustion-Sourced in this case) based on the ratios of their small additive concentrations to the background. This provided a technique that detected and attributed plumes at surprisingly low-levels of concentration.

These stationary data also helped demonstrated that operator complaints are likely to be highest at night under still atmospheres and nocturnal buildup, and that operational changes might be considered for known venting events, so that these coincide as often as possible with a well-mixed low-concentration atmosphere for rapid dilution. There are, however, several additional implications of this nocturnal phenomenon.

Firstly, since daytime and night-time baseline concentrations are different, it is difficult to establish concentration-based alert thresholds. A particularly strong inversion could make it appear as though a leak was present at the stationary location, and certainly the possible weak signals from a distant leak might be much smaller than the concentration buildup from natural emissions in the nighttime boundary layer. Accordingly, the nighttime SNR would be significantly degraded. This would less likely pose an issue for the vehicle-based monitoring, because it would be observed that these higher concentrations were present at all points, including outside the field, and including upwind.

The nocturnal buildup of gases might in the future offer some utility to coarsely estimate fluxes of trace gases. The nocturnal buildup of surface gases underneath an inversion layer of some height is not unlike that of a static soil $CO_2$ flux chamber (Pumpanen et al., 2004). Within a confined chamber of a given surface area, surface-emitted gas concentrations increase at a rate defined by the ground-to-atmosphere flux rate, and the height of the chamber. Assuming that the chamber effective height is a constant and the same for each gas, one can expect the concentrations of each gas to increase proportionately to one another. By extension, this proportionality can be applied to the fluxes, so that if one flux is known, the relative flux of the other gas can be known on the basis of its relative concentration increase. This method is purely geochemical, and independent of nocturnal boundary layer height, and made possible by measuring several gases simultaneously. This would be easiest to accomplish with $CO_2$ flux measurements for determining $CH_4$ or $H_2S$ fluxes, as $CO_2$ flux measurements are the easiest from a technical perspective. In the winter when vegetation is inactive, soil $CO_2$ ground flux measurements could be made by Forced Diffusion chamber, which have been used at successfully in the past (Risk et al., 2013). In the summers, an eddy covariance ecosystem flux measurement would be needed to define the night $CO_2$ respiration from the soil and vegetation, which is more complicated because eddy covariance measurements during the night are frequently of low quality. While the footprint of the trace gas flux estimate would not be well defined, the measurement could be done on many still winter nights, by taking the steepest slope of concentration increase the target gases during nocturnal buildup. Furthermore, anomalies corresponding to combustion or REC gas anomalies can be excluded from the analysis. Presumably, the average computed trace gas estimates over all these night times would provide some representation of total field emissions, though research would be needed to define how differing fields of view would introduce error into the analysis. The field of view of the soil or eddy covariance flux measurements and atmospheric mixing ratio measurements will differ, even in the case where they occupy exactly the same location and height. Under no circumstances will fluxes represent exactly the same composition of sources and sinks that cause the gradients in mixing ratios in the lower atmosphere, but in a horizontally uniform (atmosphere and landscape) there may still be some potential to extract a useful signal that would not be possible in other locations.

Figure 25:
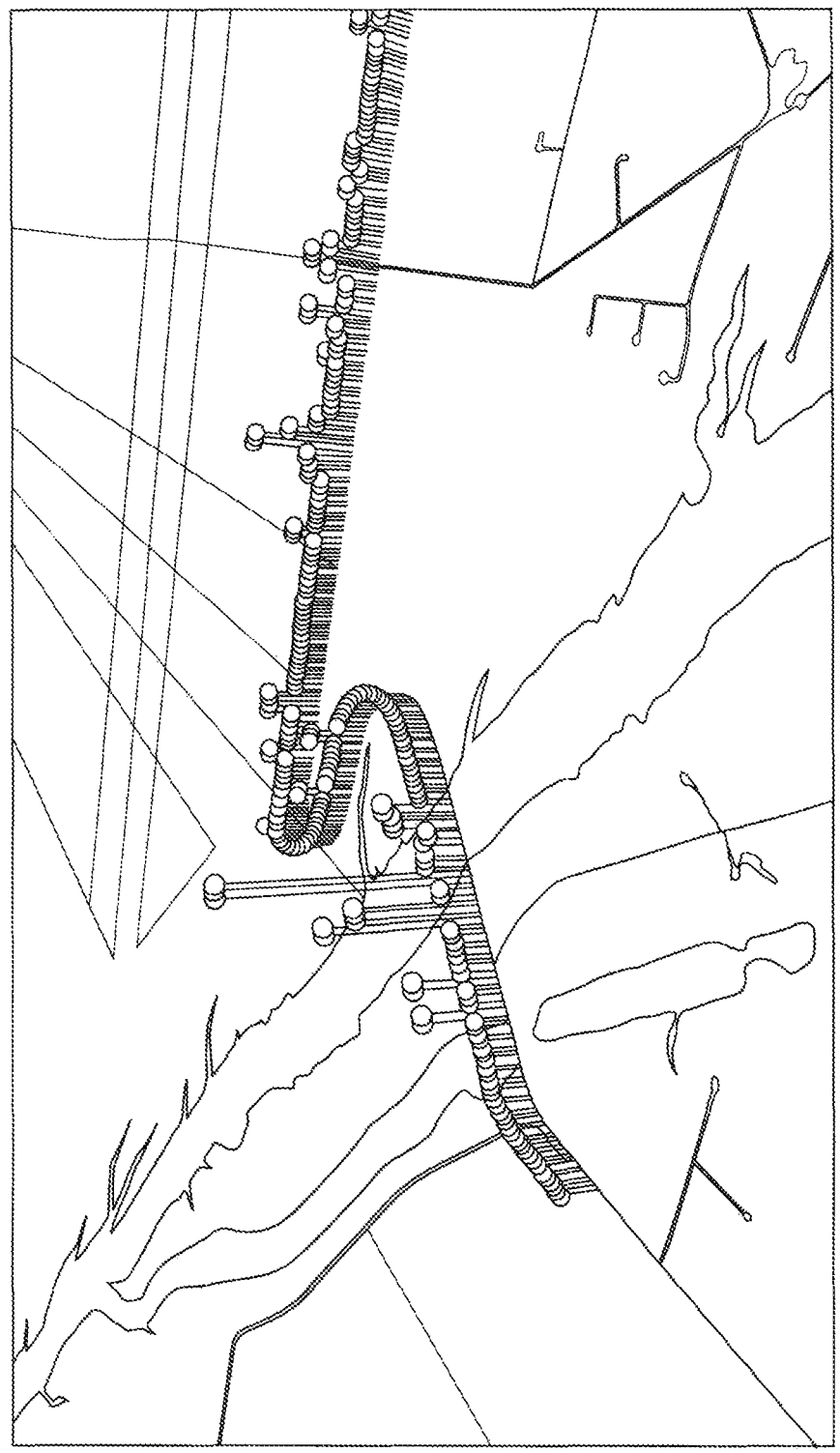
FIG. 25 illustrates results of the test survey as plotted.

FIG. 25 illustrates the data output for a small portion of a mobile survey, where data values from the CRDS instruments and GPS points were included together to produce plots, with anomalously high values plotted in red, which are in this case interpreted $H_2S$ anomalies from reducing soils on the margins of a river. If seen in a different location, such as within a dense cluster of well pads, these data might have been interpreted differently. The geolocated data are useful in helping interpret the presence of natural anomalies.

Figure 26:
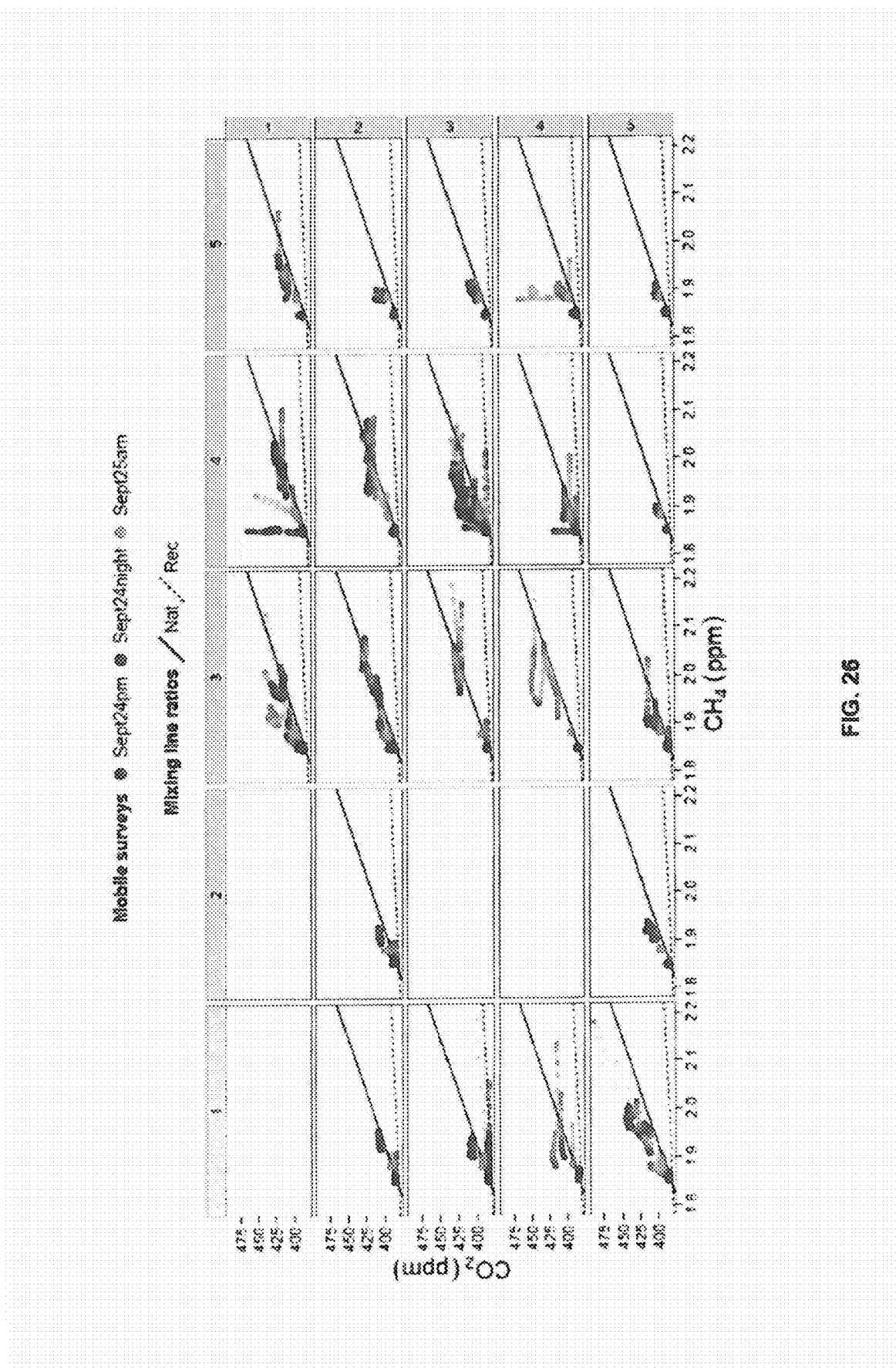
FIG. 26 illustrates mobile survey data from various test surveys.

FIG. 26 presents mobile survey device data from three surveys in late September for a 100 $km^2$ domain. FIG. 26 shows how likely source areas can be constrained by partitioning the multi-gas data into smaller quadrants for small domain visualization. Each quadrant in FIG. 26 represents the atmospheric gas data collected within that 2×2 km² area and revealed the spatial heterogeneity of the larger domain. The majority of the ~80 ppm CO2 excursions during the September 24 PM survey were captured in quadrant (4,1) in the northeast corner of the domain. Similar anomalies occurred again on September 25 AM in the same quadrant but also to the south in quadrant (5,4). These particular excursions showed little to no increase in $CH_4$, suggesting that transient $CO_2$ emissions from a tailpipe or some source with $CO_2$:$CH_4$ ratios that differed strongly from the natural and industrial sources of interest here were being observed. No areas in this survey revealed $eCO_2$:$eCH_4$ ratios that caused them to depart from natural mixing lines to tracked along industrial gas isolines. Similar experiments were performed for all collected data, and also other ratios including $eCH_4$:$H_2S$.

The observed variability in measured gases in the atmosphere can be caused by a combination of natural and human contributions. To identify and quantify the role of different potential emission sources, vehicle-based surveys are a very convenient and fast tool, and could ideally be done by someone with minimal training if the data management process were well automated. A user with a high degree of expertise would also be able to very closely isolate individual sources that might be too small to detect from the stationary location if they were to occur at margins of the field. Indeed, in the first driving campaigns, abnormalities due to industrial activities, combustion sources, and water bodies, both during daytime and nighttime could be detected.

Figure 27:
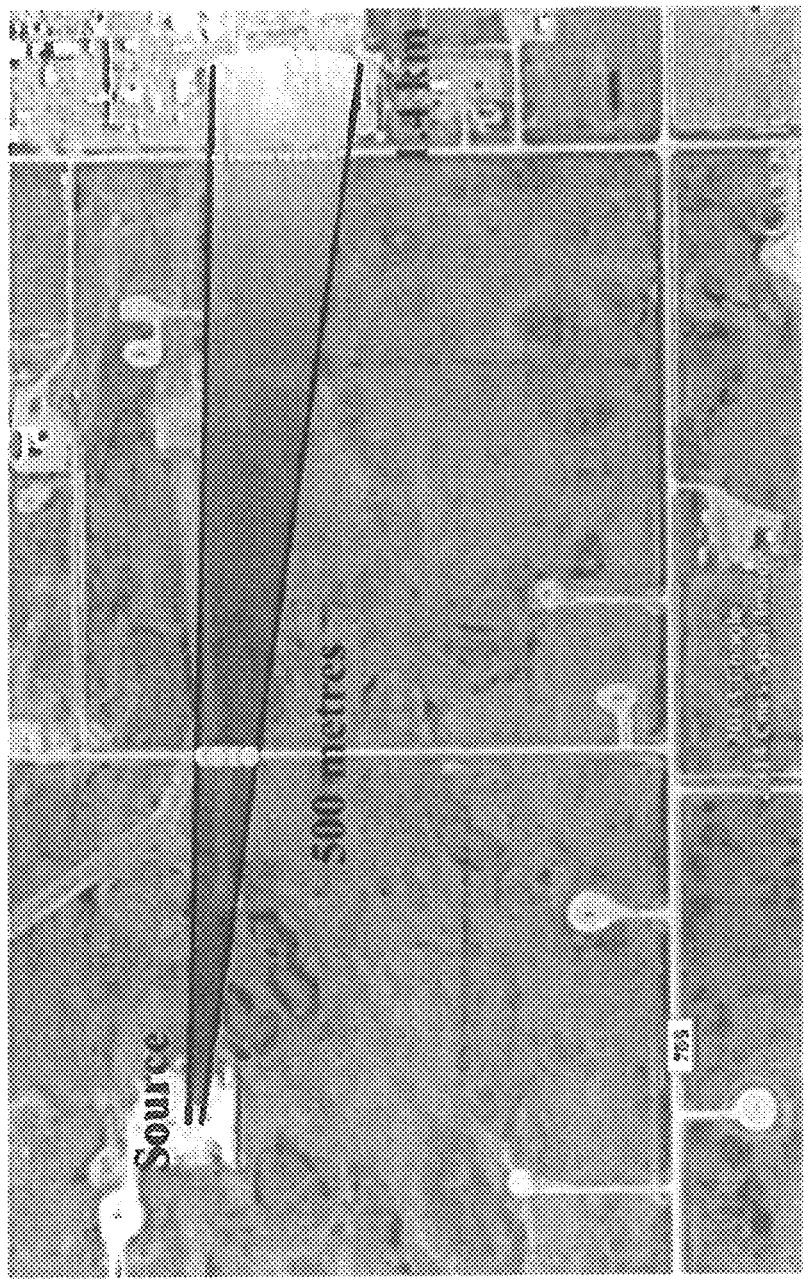
FIG. 27 illustrates a plume detected during the test survey.

FIG. 27 shows the typical form of a plume detected during a mobile survey, in this case from a combustion anomaly originating from several large trucks servicing a well site, as detected on September 24. The observed data during drive-around survey showed a large $CO_2$ emission as well as high $CO_2$/$CH_4$ ratio, consistent with combustion sources as listed in Table 2. There was no REC-type anomaly originating from this particular operation. The plume was observed along two roads. At 500 m east of the source, the dispersion plume was narrow and only several data points were logged. At 1.4 km, the plume was wider and more dilute. Peak $CO_2$ and $CH_4$ magnitudes were ~460 ppm and 1.85 ppm at 500 meters from source and ~401 ppm and 1.86 ppm at a distance of 1.4 km from source. Mapping showed that this plume was over 1 km in length, and its shape was consistent with that of a plume generated by dispersion models. This particular anomaly was detected in data post processing after the survey, and by comparing with operator records it is clear that the anomaly was due to one of several well service rigs in the field that day, performing well site maintenance. This plume corresponds to data presented in FIG. 26, as the light blue anomaly recorded in quadrant 4:1. FIG. 26 also shows that the anomaly persisted during the subsequent night survey (black points, quadrant 4:1, FIG. 26), but was more even crisply detected at night with a markedly higher $CO_2$/$CH_4$ ratio in the nocturnal boundary layer. Several dozen combustion were detected, and more importantly, REC or reservoir-type gas plumes anomalies over the course of the mobile surveys. Most of them are of modest magnitude and not exceeding regulatory guidelines, and work the operator is being carried out to analyze these data and tag observed anomalies to known service events logged in their records in order to gain operational information about the emission footprint of service events and infrastructure. These operational emission have been equivalent to limited release test experiments (e.g. Jones et al. (2014)) because all releases were unknown at the time of survey, but are recorded in company records.

The stationary survey devices (CRDS analyzers) quantify the long-term temporal variability of multiple gas emissions ($CH_4$, $CO_2$, $H_2S$, $SO_2$, $\delta^{13}CH_4$) in an industrial site (the most pressing site to monitor) within the injection field. In addition to the stationary survey devices, mobile surveys to monitor the spatial variability of multiple gas species ($CH_4$, $CO_2$, $H_2S$, $SO_2$, $\delta^{13}CH_4$) were also used, in order to cover as much landscape and as much infrastructure as possible. These are linked using a diagnostic package, with associated web viewing. These form tools for the success of the test system, as it will make automatic and efficient detection of any gas emission abnormalities.

The approach in development of this test system was to integrate the advantages of stationary and mobile sampling. Instead of having two unique arrays of instrumentation, the required instruments were communized. In effect, the stationary system was driven through the field as required, as both are not generally needed simultaneously. This approach improves the ability to isolate sources, and to detect small leaks that might be very far from the stationary location, because the stationary system can be brought to the location. It could be further improved with the addition of transport modeling for both stationary and mobile data, to better define source areas.

Overall, the test system allowed detecting modest levels of EOR-sourced reservoir gas in the atmosphere, and leakage plumes are present, but relatively infrequent and tied to activities such as drilling which are known episodic emitters. From the test surveys, there is no one area of the field that is worse than another in terms of emission, but one can recognize some spatial variance in the natural data, with some areas dominating the biogenic $CH_4$ signal. Isotopic data suggest that at some time of year, the local biosphere certainly produces more $CH_4$ than the EOR project. For $CO_2$ which is injected in large volumes into the reservoir, atmospheric variance in concentration is relatively high owing to the patchiness of natural sources over the 100 km² domain. Anomalies in $CO_2$ could be attributed entirely to local combustion sources such as well pad vehicles, flaring, local farming and processing plants. Hydrogen sulphide and other gases were present in the air occasionally, but at extremely low (less than 10 ppb) concentrations near the threshold of detection for the analyzers, which made $H_2S$-based excess ratios useful less often as an indicator of leakage. The unitized, all-pipeline nature of the project seems to minimize leaks, and emissions to the air of greenhouse and toxic gases initially appears to be modest or small as compared to reports from other projects in the literature where $CH_4$ concentrations of 2 to 3 times the surface value have been detected at high altitude (Pétron et al., 2012). Other than just containment of reservoir and EOR gases, there is much information to be gleaned on the operational side from such surveys. Companies can learn about the spatiotemporal nature of their own emission sources and identify classes of events that expose them to air quality complaints (a minority of events likely generate the majority of emissions). They can also potentially even identify service contractors who generate very fewer emissions relative to others when doing similar work. All of these could result in progressive reductions in emissions. At the same time, the contractors who are undertaking these surveys will learn a lot about the variance in natural signals, and confounding natural sources and signals in the region.

The test system exhibits three potential advantages. Firstly, it uses instruments efficiently, altering continuously between mobile and stationary deployments. While the instrument package is initially expensive, only one package is needed and the same instruments are used for every part of the program. Secondly, an effective way of quickly and effectively combining and visualizing temporally and spatially dense concentration datasets was developed. The excess-ratio detection is potentially more reliable than concentration threshold-based techniques typical of many fugitive gas and leak studies. In this test study, one can document important changes in near-surface gas concentration even on diel cycles, and to detect anomalies of either $CH_4$ or $CO_2$ individually, the alarm concentration threshold would have to be set above the highest probably 24-h value in or-der to eliminate false positives. But, this value is sometimes very high and would provide very little sensitivity in detection. The use of excess ratios is comparatively insensitive to nocturnal buildup of gases, as ground-emitted gases tend to increase and decrease proportionally with one another. It is a very flexible and reliable approach that accommodates intermittently well and poorly mixed air. Thirdly, the technique allows for detection with little use background data, so long as some a priori knowledge is available such as source signatures (basically, Table 1). In addition, the background values can come from within the datasets themselves. In effect, every survey and stationary deployment allows one to observe both natural biogenic signals and leak signals, with the former outnumbering the latter by orders of magnitude. As such, it works well to reset background concentration value at regular intervals to accommodate changes in vegetation and soil across the field. But, in topographically diverse or highly heterogeneous regions, one could reset the background every 5 or 10 minutes, as described elsewhere herein, or use a moving average at the same temporal scale, which is still a long interval relative to the interval across which a plume is profiled at mobile survey speed (10-45 seconds of detection is normal). Lastly, the computational tools not only improve the speed and reliability of the test method, but they significantly reduce needed manpower, and allow for more responsive.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

REFERENCES

Beaubien, S. E., Jones, D. G., Gal, F., Barkwith, A. K. A. P., Braibant, G., Baubron, J. C., Ciotoli, G., Graziani, S., Lister, T. R., lombardi, S., Michel, K., Quattrocchi, F., Strutt, M. H., 2013. Monitoring of near-surface gas geochemistry at the Weyburn, Canada, $CO_2$-EOR site, 2001-2011. Int. J. Greenh. Gas Control 16, S236-S262.

Bellante, G. J., Powell, S. L., Lawrence, R. L., Repasky, K. S., Dougher, T. A. O., 2013. Aerial detection of a simulated $CO_2$ leak from a geologic sequestration site using hyperspectral imagery. Int. J. Greenh. Gas Con-trol 13, 124-137.

Bowden, A. R., Pershke, D. F., Chalatumyk. R., 2013. Geosphere risk assessment conducted for the IEAGHG Weyburn-Midale $CO_2$ Monitoring and Storage Project. Int. J. Greenh. Gas Control 16, S276-S290.

Busch, K. W., Busch, M. A. 1997. Cavity ring-down spectroscopy: an ultratrace-absorption measurement technique. ACS Symposium Series 720, Oxford, UK, 199; 269 pp.

US EPA, 2014. Emission Factors for Greenhouse Gas Inventories. U.S. En-vironmental Protection Agency Washington, last Modified: 4 Apr. 2014. http://www.epa.gov/cdimateleadership/documentslemission-factors.pdf US EPA, 2013. Inventory of U.S. Greenhouse Gas Emissions and Sinks: 1990D2011. U.S. Environmental Protection Agency Washington. http://www.epa.gov/climatechange/ghgemissions/

Farrell, P., Culling, D., Leifer, I., 2013. Transcontinental methane measurements: Part 1. A mobile surface platform for source investigations. Atm. Environ. 74, 422-431.

Forster, P., Ramaswamy, V., Artaxo, P., Bemtsen, T., Betts, R., Fahey, D. W., Haywood, J., Lean, J., Lowe, D. C., Myhre, G., Nganga, J., Prinn, R., Raga, G., Schulz, M., Van Dorland, R., 2007. Changes in Atmospheric Constituents and in Radiative Forcing. In: Climate Change 2007: The Physical Science Basis. Contribution of Working Group I to the Fourth Assessment Report of the Intergovernmental Panel on Climate Change [Solomon, S., D. Qin, M. Manning, Z. Chen, M. Marquis, K. B. Averyt, M. Tignor and H. L. Miller (eds.)]. Cambridge University Press, Cambridge, United Kingdom and New York, N.Y., USA, 2007.

Hitchon, B. 2012. Best practices for validating $CO_2$ geological storage: observations and guidance from the IEAGHG Weyburn-Midale $CO_2$ storage project. Geoscience Publishing Sherwood Park, Canada, 353 pp.

Jones, D. G., Beaubien. S. E., Barkwith, A. K. A. P., Barlow, T. S., Bellomo, T., Braimant, G., Gal, F., Graziani, S., Joublin, F., Lister, T. R., Lombardi, S., 2011. Near surface gas monitoring at the Weyburn unit in 2011. British Geological Survey Commissioned Report, CR/12/014, 91 pp.

Jones, D. G., Barkwith, A. K. A. P., Hannis, S. Lister, T. R. Gal, F., Graziani, S., Beaubien, S. E., Widory, D., 2014. Monitoring of near surface gas seep-age from a shallow injection experiment at the $CO_2$ Field Lab, Norway. Int. J. Greenh. Gas Control 28, 300-317.

Karion, A., Sweeney, C., Pétron, G., Frost, G., Hardesty, M., Kofler, J., Miller, B. R., Newberger, T., Wolter, S., Banta, R., Brewer, A., Dlugo-kencky, E., Lang, P., Montzka, S. A., Schnell, R., Tans, P., Trainer, M., Zamora, R., Conley, S., 2013. Methane emissions estimate from airbone measurements over a western United States natural gas field. Geophy. Res. Lett. 40, 4393-4397.

Govindan, R., Korre, A., Durucan, S., Imrie, C. E., 2011. Comparative assessment of the performance of airbone and spaceborn spectral data for monitoring surface $CO_2$ leakages. Energy Procedia 4, 3421-3427.

Leifer, I., Culling, D., Schneising, O., Farrell, P., Buchwitz, M., Burrows, J. P., 2013. Transcontinental methane measurements: Part 2. Mobile surface investigation of fossil fuel industrial fugitive emissions. Atm. Environ. 74, 432-441.

Mayer, B., Shevalier, M., Nightingale, M., Kwon, J.-S., Johnson, G., Raistrick, M., Hutcheon, I., Perkins, E., 2013. Tracing the movement and the fate of injected $CO_2$ at the IEA GHG Weyburn-Midale $CO_2$ monitoring and storage project (Saskatchewan, Canada) using carbon isotope ratios. Int. J. Greenh. Gas Control 16S, S177-S184.

Monteil, G., Houweling, S., Dlugockenky, E. J., Maenhout, G., Vaughn, B. H., White, J. W. C., Rockmann, T., 2011. Interpreting methane variations in the past two decades using measurements of $CH_4$ mixing ratio and isotopic composition. Atm. Chem. Phys. 11, 9141-9153.

Neumann, P. P., Asadi, S., Bennetts, V. H., Lilienthal, A. J., Bartholmai, M., 2013. Monitoring of CCS areas using micro unmanned aerial vehicles (MUAVs). Energy Procedia 37, 4182-4190.

Nickerson, N., Risk, D., 2013. Using subsurface $CO_2$ concentrations and isotopologues to identify $CO_2$ seepage from $CCS/CO_2$-EOR sites: A signal-to-noise based analysis. Int. J. Greenh. Gas Control 14, 239-246

Pétron, G., Frost, G., Miller, B. R., et al., 2012. Hydrocarbon emissions characterization in the Colorado Front Range. J. Geophy. Res-Atm. 117, DOI:10.1029/2011JD016360.

Phillips, N. G., Ackley, R., Crosson, E. R., Down, A., Hutyra, L. R., Brondfield, M., Karr, J. D., Zhao, K., Jackson, R. B., 2013. Mapping urban pipeline leaks: Methane leaks across Boston. Environ. Pollut. 173, 1-4.

Pumpanen, J., Kolari, P., Ilvesniemi, H., Minkkinen, K., Vesala, T., Niinisto, S., Lohila, A., Larmola, T., Morero, M., Pihlatie, M., Janssens, I., Yuste, J. C., Grunzweig, J. M., Reth, S., Subke, J. A., Savage, K., Kutsch, W., Ostreng, G., Ziegler, W., Anthoni, P., Lindroth, A., Hari, P., 2004. Comparison of different chamber techniques for measuring soil $CO_2$ efflux. Agri. For. Met. 123, 159-176.

Quay, P., Stutsman, J., Wilbur, D., Snover, A., Dlugokencky, E., Brown, T., 1999. The isotopic composition of atmospheric methane. Global Bio-geochem. Cy. 13: doi: 10.1029/1998GB900006.

Riding, J. B., Rochette, C. A., 2005. The IEA Weyburn $CO_2$ monitoring and storage project. Final report of the European research team. British Geo-logical Survey Research Report. RR/05/03. 54 pp.

Risk, D., McArthur, G., Nickerson, N., Phillips, C., Hart, C., Egan, J., Lavoie, M., 2013. Bulk and isotopic characterization of biogenic $CO_2$ sources and variability in the Weyburn injection area. Int. J. Greenh. Gas Control 16, S263-S275.

Risk, D., Lavoie, M., Nickerson, N., under review. Carbon, capture and storage: Picking the definitive surface gas monitoring tool to detect $CO_2$ leakage. Int. J. Greenh. Gas Control.

Romanak, K. D., Bennett, P. C., Yang, C., Hovorka, S., 2012. Process-based approach to $CO_2$ seepage detection by vadose zone gas monitoring at geologic $CO_2$ storage sites. Geophys. Res. Lett. doi:10.1029/2012GL052426.

Sherk, G. W., et al. 2010. The Kerr investigation: findings of the investigation into the impact of $CO_2$ on the Kerr property; IPAC Research Inc., final report prepared for property owners Cameron and Jean Kerr, 2011. Formerly available from the International Performance Assessment Centre for $CO_2$ Storage, now in files residing with the Saskatchewan Ministry of Energy and Resources.

Shevalier, M., Nightingale, M., Mayer, B., Hutcheon, I., Durocher, K., Perkins, E., 2013. Brine geochemistry changes induced by $CO_2$ injection observed over a 10 year period in the Weyburn oil field. Int. J. Greenh. Gas Control 16S, S160-S176.

Trium, 2011. Site Assessment (SW-30-05-13-W2 M), Near Weyburn, Saskatchewan; Trium Environmental Inc. and Chemistry Matters.

Umezawa, T., Machida, T., Aoki, S., Nakazawa, T., 2012. Contributions of natural and anthropogenic sources to atmospheric methane variations over western Siberia estimated from its carbon and hydrogen isotopes. Global Biogeochem. Cy. 26, DOI: 10.1029/2011GB004232.

The invention claimed is:

1. An emission monitoring device comprising:
   a temperature-controlled and moisture-controlled enclosure comprising at least one inlet for receiving ambient air surrounding the enclosure;
   a memory unit;
   a processor coupled to the memory unit;
   at least one gas analyzer, disposed within the enclosure, the at least one gas analyzer is configured to measure a concentration of a first gas and a concentration of a second gas, the first gas and second gas being in the received ambient air contained in the enclosure;
   a positioning unit coupled to the processor and configured for determining the location at which the measurement of the concentration of the first gas was made by the at least one gas analyzer;
   an event detection unit coupled to the processor and configured for detecting the presence of a gas emission event based on a first detection ratio calculated from the measured concentration of the first gas, the measured concentration of the second gas, a background concentration of the first gas and a background concentration of the second gas, wherein the processor is configured for identifying a gas emission source causing the gas emission event based on the determined location; and
   a communication module coupled to the processor and operable to transmit to an external device first data pertaining to measurements of concentrations of the first gas, second data pertaining to measurements concentrations of the second gas, and third data pertaining to determined locations.

2. The emission monitoring device of claim 1, wherein the processor is further configured for identifying a first gas emission source as a cause of the gas emission event based on at least one characteristic of the first source.

3. The emission monitoring device of claim 2, wherein the at least one characteristic of the first source comprises at least a first gas signature of the first source, the first gas signature comprising a characterizing ratio of the amount of the first gas to the amount of the second gas emitted from the first source; and
   wherein identifying the first source as a cause of the gas emission event based on the at least one characteristic of the given source comprises comparing the first calculated ratio to the characterizing ratio of the first source.

4. The emission monitoring device of claim 3, wherein the at least one characteristic of the first source further comprises the location of the first source.

5. The emission monitoring device of claim 3, wherein identifying the first source as the cause of the gas emission event is further based on the topology of the geographic area surrounding the location of the at least one gas analyzer when the concentration of the first gas is measured.

6. The emission monitoring device of claim 3, wherein the at least one analyzer is operable for measuring a concentration of a third gas; and wherein the processor of the computer-implemented event detection system is further configured for:
   determining a third difference between the measured concentration of the third gas and a background concentration of the third gas;
   calculating a second detection ratio by computing the ratio of the second difference to the third difference; and identifying a second gas emission source as the cause of the gas emission event based on comparison of the second detection ratio to a second gas-signature of the second source, the second gas-signature comprising a characterizing ratio of an amount of the second gas to an amount of the third gas emitted from the second source.

7. The emission monitoring device of claim 3, wherein the at least one analyzer is operable for measuring a concentration of a third gas; and wherein the processor of the computer-implemented event detection system is further configured for:
   determining a third difference between the measured concentration of the third gas and a background concentration of the third gas;
   calculating a second detection ratio by computing the ratio of the second difference to the third difference; and
   validating a first gas emission source as the cause of the gas emission event based on comparison of the second detection ratio to a second gas-signature of the first source, the second gas-signature comprising a characterizing ratio of an amount of the second gas to an amount of the third gas.

8. The emission monitoring device of claim 1, wherein detecting the presence of the gas emission event comprises:
   determining a first difference between the measured concentration of the first gas and the background concentration of the first gas;
   determining a second difference between the measured concentration of the second gas and the background concentration of the second gas; and
   calculating the first detection ratio by computing the ratio of the first difference to the second difference.

9. The emission monitoring device of claim 8, wherein detecting the presence of the gas emission event based on the first ratio comprises comparing the first detection ratio with at least one predetermined threshold ratio value.

10. The emission monitoring device of claim 1, further comprising a wind measurement device for measuring the wind direction in proximity of the location of the at least one gas analyzer when the concentration of the first gas is measured, and wherein the processor is further configured for determining the location of the gas emission event based on the measured wind direction.

11. The emission monitoring device of claim 10, wherein the wind measurement device is further configured for measuring the wind velocity in proximity of the location of the at least one gas analyzer when the concentration of the first gas is measured, and wherein determining the location of the gas emission event is further based on the measured wind velocity.

12. The emission monitoring device of claim 1, wherein the background concentration of the first gas and the background concentration of the second gas are selected based on at least one of: time of day; time of year; location of the first gas analyzer when the concentration of the first gas is measured; and meteorological conditions.

13. The emission monitoring device of claim 1, wherein the background concentration of the first gas and the background concentration of the second gas are selected based on at least one of: minimum value during sampling period, moving average, padded moving average, running minimum and padded running minimum.

14. A gas emission event detection system comprising:
   a memory unit for storing a plurality of instructions;
   a processor coupled to the memory unit, the processor configured for:
      receiving a measurement of a concentration of a first gas from a gas analyzer within a temperature-controlled and moisture-controlled enclosure with at least one inlet for receiving ambient air surrounding the enclosure;
      determining with a positioning system the location at which the measurement of the concentration of the first gas was made by the gas analyzer;
      receiving a measurement of a concentration of a second gas at substantially the same location;
      determining a background concentration value for the first gas;
      determining a background concentration value for the second gas;
      detecting the presence of a gas emission event based on a first detection ratio calculated from the measured concentration of the first gas, the measured concentration of the second gas, the background concentration of the first gas, and the background concentration of the second gas;
      identifying a gas emission source causing the gas emission event based on the determined location; and
      transmitting to an external device first data pertaining to measurements of concentrations of the first gas, second data pertaining to measurements of concentrations of the second gas, and third data pertaining to determined locations.

15. The gas emission event detection system of claim 14, wherein the processor is further configured for identifying a first source as a cause of the gas emission event based on at least one characteristic of the first source.

16. The gas emission event detection system of claim 15, wherein the at least one characteristic of the first source comprises at least a first gas signature of the first source, the first gas signature comprising a characterizing ratio of an amount of the first gas to an amount of the second gas emitted from the first source; and
   wherein identifying the first source as a cause of the gas emission event based on at least one characteristic of the given source comprises comparing the first detection ratio to the characterizing ratio of the first source.

17. The gas emission event detection system of claim 16, wherein the at least one characteristic of the first source further comprises the location of the first source.

18. The gas emission event detection system of claim 16, wherein identifying the first source as the cause of the gas emission event is further based on the topology of the geographic area surrounding the location of the gas analyzer when the concentration of the first gas is measured.

19. The gas emission event detection system of claim 16, wherein the processor is further configured for:
   receiving a measurement of a concentration of a third gas;
   determining a third difference between the measured concentration of the third gas and a background concentration of the third gas;
   calculating a second detection ratio by computing the ratio of the second difference to the third difference; and
   identifying a second gas emission source as the cause of the gas emission event based on comparison of the second detection ratio to a second gas-signature of the second source, the second gas-signature comprising a characterizing ratio of an amount of the second gas to an amount of the third gas emitted from the second source.

20. The gas emission event detection system of claim 16, wherein the processor is further configured for:
receiving a measurement of a concentration of a third gas;
determining a third difference between the measured concentration of the third gas and a background concentration of the third gas;
calculating a second detection ratio by computing the ratio of the second difference to the third difference; and
validating a first gas emission source as the cause of the gas emission event based on comparison of the second detection ratio to a second gas-signature of the first source, the second gas-signature comprising a characterizing ratio of an amount of the second gas to an amount of the third gas.

21. The gas emission event detection system of claim 14, wherein detecting the presence of the gas emission event comprises:
determining a first difference between the measured concentration of the first gas and the background concentration of the first gas;
determining a second difference between the measured concentration of the second gas and the background concentration of the second gas;
calculating the first detection ratio by computing a ratio of the first difference to the second difference.

22. The gas emission event detection system of claim 21, wherein detecting the presence of the gas emission event comprises comparing the first detection ratio with a predetermined ratio threshold.

23. The gas emission event detection system of claim 14, wherein the processor is further configured for receiving a measurement of a wind direction, and wherein the processor is further configured for determining a location of the gas emission event based on the measured wind direction.

24. The gas emission event detection system of claim 23, wherein the processor is further configured for receiving a measurement of a wind velocity, and wherein determining the location of the gas emission event is further based on the measured wind velocity.

25. The gas emission event detection system of claim 14, wherein the background concentration of the first gas and the background concentration of the second gas are determined based on at least one of: time of day; time of year; location of the gas analyzer when the concentration of the first gas is measured; and meteorological conditions.

26. The emission monitoring system of claim 14, wherein the background concentration of the first gas and the background concentration of the second gas are selected based on at least one of: minimum value during sampling period, moving average, padded moving average, running minimum and padded running minimum.

* * * * *